United States Patent
Wands et al.

(10) Patent No.: US 10,442,868 B2
(45) Date of Patent: Oct. 15, 2019

(54) TREATING HEPATITIS B VIRUS INFECTIONS BY ADMINISTERING RECEPTOR ASSOCIATED PROTEIN (RAP)

(71) Applicant: Rhode Island Hospital, A Lifespan-Partner, Providence, RI (US)

(72) Inventors: Jack R. Wands, Providence, RI (US); Jisu Li, Barrington, RI (US); Shuping Tong, Barrington, RI (US)

(73) Assignee: Rhode Island Hospital, A Lifespan-Partner, Providence, RI (US)

( * ) Notice: Subject to any disclaimer, the term of this patent is extended or adjusted under 35 U.S.C. 154(b) by 43 days.

(21) Appl. No.: 14/775,459

(22) PCT Filed: Mar. 13, 2014

(86) PCT No.: PCT/US2014/025788
§ 371 (c)(1),
(2) Date: Sep. 11, 2015

(87) PCT Pub. No.: WO2014/160088
PCT Pub. Date: Oct. 2, 2014

(65) Prior Publication Data
US 2016/0024223 A1 Jan. 28, 2016

Related U.S. Application Data

(60) Provisional application No. 61/783,327, filed on Mar. 14, 2013.

(51) Int. Cl.
| | |
|---|---|
| *A61P 1/16* | (2006.01) |
| *A61P 31/20* | (2006.01) |
| *A61K 38/17* | (2006.01) |
| *A61K 39/29* | (2006.01) |
| *C07K 16/40* | (2006.01) |
| *A61K 45/06* | (2006.01) |
| *C07K 16/28* | (2006.01) |
| *C12N 15/113* | (2010.01) |
| *C07K 14/47* | (2006.01) |
| *C07K 14/705* | (2006.01) |
| *C07K 14/02* | (2006.01) |

(52) U.S. Cl.
CPC ............ *C07K 16/40* (2013.01); *A61K 38/177* (2013.01); *A61K 38/1709* (2013.01); *A61K 39/292* (2013.01); *A61K 45/06* (2013.01); *A61P 1/16* (2018.01); *A61P 31/20* (2018.01); *C07K 16/28* (2013.01); *C12N 15/1131* (2013.01); *C07K 14/02* (2013.01); *C07K 14/4703* (2013.01); *C07K 14/705* (2013.01); *C07K 2317/24* (2013.01); *C07K 2317/54* (2013.01); *C07K 2317/55* (2013.01); *C07K 2317/622* (2013.01); *C07K 2317/76* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,650,391 A | 7/1997 | Schwartz et al. |
| 2007/0224198 A1 | 9/2007 | Blackburn et al. |
| 2009/0104209 A1 | 4/2009 | Seidah et al. |
| 2010/0279928 A1 | 11/2010 | Rubinstein |
| 2011/0033465 A1 | 2/2011 | Hedrick et al. |
| 2011/0189084 A1* | 8/2011 | Zankel ............... A61K 38/177 424/1.11 |
| 2011/0212105 A1 | 9/2011 | Huerta-Galindo et al. |
| 2012/0207709 A1 | 8/2012 | Hamatake |
| 2012/0251444 A1 | 10/2012 | Starr et al. |

FOREIGN PATENT DOCUMENTS

| | | | |
|---|---|---|---|
| WO | WO-2008036682 A2 * | 3/2008 | ......... A61K 38/168 |
| WO | 2011/103516 | 8/2011 | |
| WO | 2011/159769 | 12/2011 | |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Lee et al (2006. Molecular Cell. 22: 423-430).*
Ray et al, 2004, Biochemical Pharmacology. 68: 1825-1832 (Year: 2004).*
International Search Report and Written Opinion issued in PCT/US2014/25788 dated Dec. 3, 2014 (14 pages).
Guttman et al., "Structure of the minimal interface between ApoE and LRP," Journal of molecular biology, 398.2: 306-319 (2010).
Jeon et al., "Structure and physiologic function of the low-density lipoprotein receptor," Annu. Rev. Biochem., 74: 535-562 (2005).
Lillis et al., "The low density lipoprotein receptor-related protein 1: unique tissue-specific functions revealed by selective gene knockout studies," Physiological reviews, 88.3: 887-918 (2008).
Simonovic et al. "Calcium coordination and pH dependence of the calcium affinity of ligand-binding repeat CR7 from the LRP. Comparison with related domains from the LRP and the LDL receptor," Biochemistry, 40.50: 15127-15134 (2001).

* cited by examiner

*Primary Examiner* — Zachary C Howard
(74) *Attorney, Agent, or Firm* — Fish & Richardson P.C.

(57) ABSTRACT

The specification provides compositions and methods of reducing a risk of a HBV infection in a subject and of treating a subject infected with HBV.

22 Claims, 10 Drawing Sheets
Specification includes a Sequence Listing.

FIG. 3

TREATING HEPATITIS B VIRUS INFECTIONS BY ADMINISTERING RECEPTOR ASSOCIATED PROTEIN (RAP)

CROSS REFERENCE TO RELATED APPLICATIONS

This application is a U.S. National Phase Application under 35 U.S.C. § 371 of International Patent Application No. PCT/US2014/025788, filed on Mar. 13, 2014, which claims priority to U.S. Patent Application Ser. No. 61/783,327, filed Mar. 14, 2013, the disclosure of which is incorporated herein by reference in its entirety.

TECHNICAL FIELD

The claimed methods relate to reducing a risk of a hepatitis B virus (HBV) infection in a subject and to treating a subject infected with HBV.

BACKGROUND

Hepatitis B is an infectious inflammatory illness of the liver caused by HBV. The disease has caused epidemics in parts of Asia and Africa, and hepatitis B is highly endemic in China. About a third of the world population has been infected with HBV at one point in their lives, and approximately 300 million people worldwide are chronically infected with HBV. Hepatitis B is a major global health problem and the most serious type of viral hepatitis as it puts people at high risk of death from cirrhosis of the liver and hepatocellular carcinoma.

A vaccine against hepatitis B has been available since 1982. The hepatitis B vaccine, which is made from inactivated HBV, is about 95% effective in preventing infection and its chronic consequences. Once infected with HBV, however, there are only two types of agents approved to treat a chronic HBV infection. Pegylated interferons are effective in only a small fraction of patients, have serious side effects, and are expensive. Nucleoside or nucleotide analogues are potent inhibitors of HBV DNA replication, but they fail to clear the covalently closed circular (ccc) DNA, the template of viral DNA replication and protein expression. They also fail to block the expression of viral proteins. For example, hepatitis B surface antigen (HBsAg) is believed to promote viral persistent infection by inducing immune tolerance. Nucleoside analogue therapy rarely promotes the loss of HBsAg followed by the rise of corresponding antibody (called HBsAg seroconversion), a marker of sustained virological response. In this regard, targeting host factors for HBV entry may block the viral lifecycle at the first step. Targeting HBsAg secretion may also promote HBsAg seroconversion.

Chronic infection with HBV greatly increases the risk to develop liver cancer. Current therapies with interferons and nucleoside or nucleotide analogues suffer from low response rate or induction of drug resistance. Maintenance of a persistent infection in the liver requires continuous release of infectious virions from infected hepatocytes for de novo infection of regenerated cells.

Despite decades of extensive search, host factors required for HBV entry into hepatocytes remain ill defined. At present, heparan sulfate proteoglycan (HSPG) has been identified as a low-affinity HBV receptor. A high-affinity, proteineous HBV receptor remains obscure, although a sodium-dependent, co-transporting polypeptide (NTCP) has recently been proposed as a HBV receptor (Yang H et al., eLife 1: e00049). HBV expresses three envelope proteins: large (L), middle (M), and small (S). These three proteins are translated from the same gene through alternative, in-frame start codons, with the M protein comprising extra N-terminal sequence (preS2 domain) over the S protein, and the L protein comprising extra N-terminal sequence (preS1 domain) over the M protein. The envelope proteins, especially the L protein, are believed to mediate HBV attachment to the high-affinity HBV receptor. Many proteins have been identified that bind to a HBV envelope protein, but none of them are receptors for HBV on hepatocytes.

SUMMARY

The present disclosure is based, in part, on the discovery that low density lipoprotein receptor (LDLR), low density lipoprotein receptor related protein (LRP), and Factor Xa (FXa), interact with HBV, e.g., as components of a HBV receptor complex, on hepatocytes. Accordingly, the present specification provides methods of treating a subject against a HBV infection, e.g., reducing a risk of a HBV infection in a subject and treating a subject infected with HBV.

In some aspects, the present disclosure provides methods of treating a subject infected with HBV, the method comprising administering to a subject infected with HBV a therapeutically effective amount of LDLR, LRP, receptor associated protein (RAP), LDLR inhibitor, LRP inhibitor, FXa inhibitor, or any combination thereof, to thereby treat the subject infected with HBV. The LDLR, LRP, and/or RAP can be, e.g., in a purified form, e.g., as a component of a pharmaceutical composition. In one embodiment, the methods include administering to the subject a pegylated interferon or a nucleoside or nucleotide analogue.

The present disclosure also features methods of reducing a risk of a HBV infection in a subject, the method comprising administering to a subject at risk of a HBV infection a therapeutically effective amount of LDLR, LRP, RAP, LDLR inhibitor, LRP inhibitor, FXa inhibitor, or any combination thereof, to thereby reduce the risk of a HBV infection in the subject. The LDLR, LRP, and/or RAP can be, e.g., in a purified form, e.g., as a component of a pharmaceutical composition. In some embodiments, the method includes administering to the subject a HBV vaccine.

In some aspects, the present disclosure provides uses of LDLR, LRP, RAP, LDLR inhibitor, LRP inhibitor, FXa inhibitor, or any combination thereof, to treat a subject against a HBV infection, e.g., reduce a risk of a HBV infection in a subject and treat a subject infected with HBV, the use comprising administering to the subject a therapeutically effective amount of LDLR, LRP, RAP, LDLR inhibitor, LRP inhibitor, FXa inhibitor, or any combination thereof. The LDLR, LRP, and/or RAP can be, e.g., in a purified form, e.g., as a component of a pharmaceutical composition.

In some embodiments, the LDLR comprises an amino acid sequence that has at least 90% identity, e.g., at least 92%, 95%, 96%, 97%, 98%, or 99% identity, to SEQ ID NO:2. In one embodiment, the LRP comprises an amino acid sequence that has at least 90% identity, e.g., at least 92%, 95%, 96%, 97%, 98%, or 99% identity, to SEQ ID NO:4. In some embodiments, the RAP comprises an amino acid sequence that has at least 90% identity, e.g., at least 92%, 95%, 96%, 97%, 98%, or 99% identity, to SEQ ID NO:6.

In one embodiment, the LDLR inhibitor comprises an anti-LDLR antibody or antigen-binding fragment thereof, e.g., a monoclonal antibody, polyclonal antibody, chimeric antibody, humanized antibody, single chain antibody, Fab fragment, or F(ab')$_2$ fragment. In some embodiments, the LDLR inhibitor comprises an inhibitory nucleic acid effective to specifically reduce expression of LDLR, e.g., a LDLR expression reducing small interfering RNA molecule or antisense nucleic acid.

In one embodiment, the LRP inhibitor comprises an anti-LRP antibody or antigen-binding fragment thereof, e.g., a monoclonal antibody, polyclonal antibody, chimeric antibody, humanized antibody, single chain antibody, Fab fragment, or F(ab')$_2$ fragment. In some embodiments, the LRP inhibitor comprises an inhibitory nucleic acid effective to specifically reduce expression of LRP, e.g., a LRP expression reducing small interfering RNA molecule or antisense nucleic acid.

In some embodiments, the FXa inhibitor comprises an anti-FXa antibody or antigen binding fragment thereof, e.g., a monoclonal antibody, polyclonal antibody, chimeric antibody, humanized antibody, single chain antibody, Fab fragment, or F(ab')$_2$ fragment. In one embodiment, the FXa inhibitor is selected from the group consisting of antistasin, antistasin-related peptides, tick anticoagulant peptide (TAP), fondaparinux, draparinux, rivaroxaban, apixaban, betrixaban, edoxaban, and otamixaban.

In one embodiment, two or more of LDLR, LRP, RAP, LDLR inhibitor, LRP inhibitor, and FXa inhibitor are administered, e.g., orally, intravenously, or by injection, to the subject, e.g., a mammal, a human. The LDLR, LRP, and/or RAP can be, e.g., in a purified form, e.g., as a component of a pharmaceutical composition.

The present disclosure also features methods of identifying a candidate anti-HBV agent, the method comprising providing a cell expressing a polypeptide comprising an amino acid sequence that has at least 90% identity, e.g., at least 92%, 95%, 96%, 97%, 98%, or 99% identity, to SEQ ID NO:2 and/or 4; providing a HBV; contacting the cell with the HBV in the presence of a test compound; determining a level of HBsAg secretion; and comparing the level of HBsAg secretion in the presence of the test compound with the level of HBsAg secretion in the absence of the test compound, wherein a reduced level of HBsAg secretion in the presence of the test compound than in its absence indicates that the test compound is a candidate anti-HBV agent.

In some embodiments, the cell expresses a polypeptide comprising an amino acid sequence that has at least 90% identity, e.g., at least 92%, 95%, 96%, 97%, 98%, or 99% identity, to SEQ ID NO:2. In one embodiment, the cell expresses a polypeptide comprising an amino acid sequence that has at least 90% identity, e.g., at least 92%, 95%, 96%, 97%, 98%, or 99% identity, to SEQ ID NO:4. In some embodiments, the test compound is selected from the group consisting of deoxyribonucleic acids, ribonucleic acids, polypeptides, and small molecules.

In one aspect of the disclosure, pharmaceutical compositions are provided that comprise a compound that inhibits or reduces interaction between HBV and HBV receptor complex, wherein HBV receptor complex comprises LDLR, LRP, and FXa; and a pharmaceutically acceptable carrier. In some embodiments, the compound is selected from the group consisting of deoxyribonucleic acids, ribonucleic acids, polypeptides, and small molecules.

In yet a further aspect of the disclosure, compositions comprising a therapeutically effective amount of LDLR, LRP, RAP (e.g., in purified form), or any combination thereof; and a pharmaceutically acceptable carrier, are provided. In some embodiments, the LDLR comprises an amino acid sequence that has at least 90% identity, e.g., at least 92%, 95%, 96%, 97%, 98%, or 99% identity, to SEQ ID NO:2. In one embodiment, the LRP comprises an amino acid sequence that has at least 90% identity, e.g., at least 92%, 95%, 96%, 97%, 98%, or 99% identity, to SEQ ID NO:4. In some embodiments, the RAP comprises an amino acid sequence that has at least 90% identity, e.g., at least 92%, 95%, 96%, 97%, 98%, or 99% identity, to SEQ ID NO:6. In some embodiments, the composition comprises a combination of two or more of LDLR, LRP, and RAP. In some embodiments, the composition comprises a FXa inhibitor, a pegylated interferon, a nucleoside or nucleotide analogue, a HBV vaccine, or any combination thereof.

As used herein, the term "hepatitis B" refers to an infectious inflammatory illness of the liver caused by the HBV. This disease and its symptoms are well-known in the art and are described herein.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing, reducing risk, or delaying the spread (e.g., reinfection) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of HBV infection. The methods of the invention contemplate any one or more of these aspects of treatment.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DESCRIPTION OF DRAWINGS

FIG. 3 is a panel of two photomicrographs showing selective killing of hepatocytes in differentiated HepaRG cells by a toxin utilizing LRP as its receptor. Hepatocyte islands are circled.

DETAILED DESCRIPTION

Figure 1:
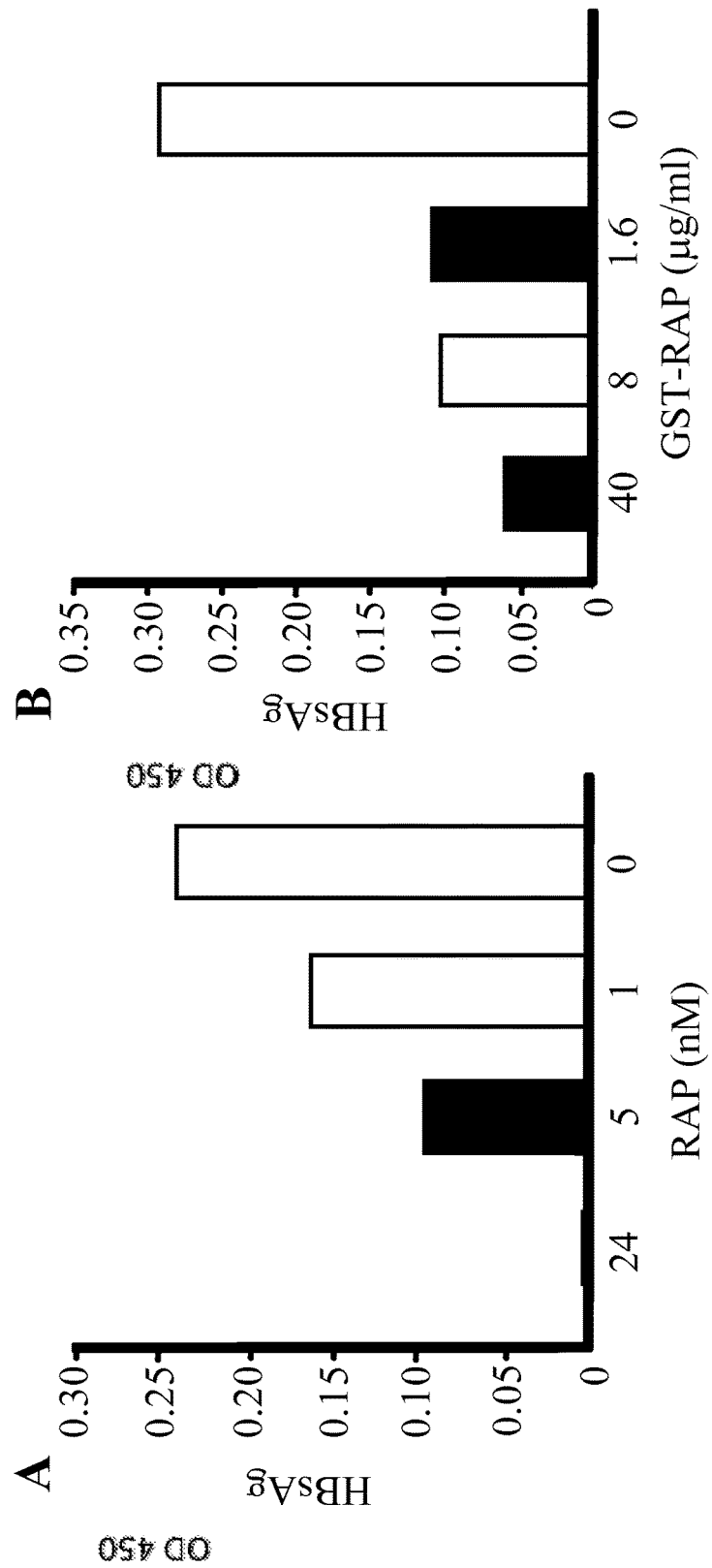
FIG. 1 is a panel of two bar graphs showing that RAP (A) and GST-RAP (B) inhibit HBV infection of HepaRG cells. Shown are OD values for HBsAg after subtracting value from non-infected cells.

The methods and uses described herein are based, at least in part, on the discovery that LDLR, LRP, and FXa interact with HBV, e.g., as components of a HBV receptor complex, on hepatocytes and that HBV infection of liver cells can be suppressed by a LDLR inhibitor, a LRP inhibitor, RAP, a FXa inhibitor, antistasin and/or antistasin-related peptides (Tuszynski et al., J Biol Chem 262:9718-23, 1987; Nutt et al., J Biol Chem 263:10162-7, 1988), as well as by silencing the expression of LRP or LDLR by small interfering RNA (siRNA) or short hairpin RNA (shRNA). Accordingly, a therapeutic strategy provided herein involves inhibiting interaction between LDLR and LRP on hepatocytes and HBV, thereby inhibiting HBV infection. Inhibiting this interaction can be performed in a number of ways, e.g., by administering RAP to sequester both LDLR and LRP, or antistasin or antistasin-related peptides to inhibit L protein cleavage. Alternatively, or in combination, soluble LDLR and/or LRP proteins, or fragments thereof, could compete with cognate proteins on the surface of a hepatocyte to bind HBV particles in circulation. Another option is to silence the expression of LRP and/or LDLR on hepatocytes by RNA interference.

Accordingly, provided herein are compositions and methods for treating a subject infected with HBV by administering a therapeutically effective amount of a LDLR inhibitor, LRP inhibitor, RAP, LDLR, LRP, and/or a FXa inhibitor such as antistasin or an antistasin-related peptide (Tuszynski et al., J Biol Chem 262:9718-23, 1987; Nutt et al., J Biol Chem 263:10162-7, 1988). Also provided herein are compositions and methods of reducing a risk of a HBV infection, which include administering to a subject at risk of a HBV infection a therapeutically effective amount of LDLR inhibitor, LRP inhibitor, RAP, LDLR, LRP, and/or a FXa inhibitor such as antistasin or an antistasin-related peptide. In some embodiments, the methods described herein include administering a combination of two or more, e.g., three or more, four or more, five or more, or all six, of a LDLR inhibitor, LRP inhibitor, RAP, LDLR, LRP, and/or FXa inhibitor such as antistasin or an antistasin-related peptide. The methods described herein can further include administering to the subject a HBV vaccine, a pegylated interferon, or a nucleoside or nucleotide analogue. Such an approach is highly recommended for infants born to HBV infected mothers, especially if the mother is HBeAg positive.

Treatable Subjects

A subject can be selected on the basis that they are infected with HBV, are suspected to be infected with HBV, and/or are at risk of a HBV infection. It is well within the skills of an ordinary practitioner to recognize a subject that is infected with HBV, suspected to be infected with HBV, or at risk of a HBV infection. A subject that is infected with HBV, suspected to be infected with HBV, or at risk of a HBV infection is, for example, one having one or more symptoms of the condition or one or more risk factors for developing the condition. Symptoms of HBV infection are known to those of skill in the art and include, without limitation, general ill-health, extreme fatigue, loss of appetite, nausea, vomiting, body aches, mild fever, dark urine, jaundice, serum-sickness-like syndrome, acute necrotizing vasculitis (polyarteritis nodosa), membranous glomerulonephritis, papular acrodermatitis of childhood (Gianotti-Crosti syndrome), inflammation of the liver, cirrhosis, and hepatocellular carcinoma. A subject that has or is at risk of a HBV infection is one with known risk factors such as infants born to infected mothers, people with high-risk sexual behavior (e.g., people who have sexual contact with an infected person, have multiple sex partners, have a sexually transmitted disease, and men who have sexual encounters with other men), partners and household contacts of infected people, injecting drug users, people who frequently require blood or blood products, recipients of solid organ transplantation, people at occupational risk of HBV infection, including health-care workers, and travellers to countries with high rates of hepatitis B. The methods are effective for a variety of subjects including mammals, e.g., humans. The subject can be an adult or child.

LDLR

The LDLR is well known in the art and is a mosaic protein that mediates the endocytosis of cholesterol-rich LDL. LDLR is a cell-surface receptor that recognizes apoprotein B100, which is embedded in the phospholipid outer layer of LDL particles. The LDLR also recognizes the apoE protein found in chylomicron remnants and VLDL remnants (IDL). In humans, the LDLR protein is encoded by the LDLR gene. It is the prototype of the LDLR gene family, which also includes LRP, LRP-1b, megalin, very low density lipoprotein receptor (VLDLR), apoE receptor 2 (or LRP8), and multiple epidermal growth factor repeat containing protein (MEGF7). Several examples of LDLR are highlighted below in Table 1.

TABLE 1

The LDLR orthologs from three different species along with their GenBank RefSeq Accession Numbers.

| Species | Nucleic Acid | Amino Acid | GeneID |
|---|---|---|---|
| *Homo sapiens* | NM_000527.4 | NP_000518.1 | 3949 |
| *Mus musculus* | NM_001252658.1 | NP_001239587.1 | 16835 |
| *Rattus norvegicus* | NM_175762.2 | NP_786938.1 | 300438 |

In one example, LDLR can be encoded by a 2583 base pair sequence found on chromosome 19 of the human genome (SEQ ID NO:1). The protein, as shown below, is 860 residues long (SEQ ID NO:2).

LDLR Nucleic Acid Sequence

```
                                            (SEQ ID NO: 1)
ATGGGGCCCTGGGGCTGGAAATTGCGCTGGACCGTCGCCTTGCTCCTCGC

CGCGGCGGGGACTGCAGTGGGCGACAGATGCGAAAGAAACGAGTTCCAGT

GCCAAGACGGGAAATGCATCTCCTACAAGTGGGTCTGCGATGGCAGCGCT

GAGTGCCAGGATGGCTCTGATGAGTCCCAGGAGACGTGCTTGTCTGTCAC

CTGCAAATCCGGGGACTTCAGCTGTGGGGCCGTGTCAACCGCTGCATTC

CTCAGTTCTGGAGGTGCGATGGCCAAGTGGACTGCGACAACGGCTCAGAC

GAGCAAGGCTGTCCCCCCAAGACGTGCTCCCAGGACGAGTTTCGCTGCCA

CGATGGGAAGTGCATCTCTCGGCAGTTCGTCTGTGACTCAGACCGGGACT

GCTTGGACGGCTCAGACGAGGCCTCCTGCCCGGTGCTCACCTGTGGTCCC

GCCAGCTTCCAGTGCAACAGCTCCACCTGCATCCCCCAGCTGTGGGCCTG

CGACAACGACCCCGACTGCGAAGATGGCTCGGATGAGTGGCCGCAGCGCT

GTAGGGGTCTTTACGTGTTCCAAGGGGACAGTAGCCCCTGCTCGGCCTTC

GAGTTCCACTGCCTAAGTGGCGAGTGCATCCACTCCAGCTGGCGCTGTGA

TGGTGGCCCCGACTGCAAGGACAAATCTGACGAGGAAAACTGCGCTGTGG

CCACCTGTCGCCCTGACGAATTCCAGTGCTCTGATGGAAACTGCATCCAT

GGCAGCCGGCAGTGTGACCGGGAATATGACTGCAAGGACATGAGCGATGA

AGTTGGCTGCGTTAATGTGACACTCTGCGAGGGACCCAACAAGTTCAAGT

GTCACAGCGGCGAATGCATCACCCTGGACAAAGTCTGCAACATGGCTAGA

GACTGCCGGGACTGGTCAGATGAACCCATCAAAGAGTGCGGGACCAACGA

ATGCTTGGACAACAACGGCGGCTGTTCCCACGTCTGCAATGACCTTAAGA

TCGGCTACGAGTGCCTGTGCCCCGACGGCTTCCAGCTGGTGGCCCAGCGA

AGATGCGAAGATATCGATGAGTGTCAGGATCCCGACACCTGCAGCCAGCT

CTGCGTGAACCTGGAGGGTGGCTACAAGTGCCAGTGTGAGGAAGGCTTCC

AGCTGGACCCCCACACGAAGGCCTGCAAGGCTGTGGGCTCCATCGCCTAC

CTCTTCTTCACCAACCGGCACGAGGTCAGGAAGATGACGCTGGACCGGAG

CGAGTACACCAGCCTCATCCCCAACCTGAGGAACGTGGTCGCTCTGGACA

CGGAGGTGGCCAGCAATAGAATCTACTGGTCTGACCTGTCCCAGAGAATG

ATCTGCAGCACCCAGCTTGACAGAGCCCACGGCGTCTCTTCCTATGACAC

CGTCATCAGCAGAGACATCCAGGCCCCCGACGGGCTGGCTGTGGACTGGA

TCCACAGCAACATCTACTGGACCGACTCTGTCCTGGGCACTGTCTCTGTT
```

-continued
```
GCGGATACCAAGGGCGTGAAGAGGAAAACGTTATTCAGGGAGAACGGCTC

CAAGCCAAGGGCCATCGTGGTGGATCCTGTTCATGGCTTCATGTACTGGA

CTGACTGGGGAACTCCCGCCAAGATCAAGAAAGGGGGCCTGAATGGTGTG

GACATCTACTCGCTGGTGACTGAAAACATTCAGTGGCCCAATGGCATCAC

CCTAGATCTCCTCAGTGGCCGCCTCTACTGGGTTGACTCCAAACTTCACT

CCATCTCAAGCATCGATGTCAACGGGGGCAACCGGAAGACCATCTTGGAG

GATGAAAGAGGCTGGCCCACCCCTTCTCCTTGGCCGTCTTTGAGGACAA

AGTATTTTGGACAGATATCATCAACGAAGCCATTTTCAGTGCCAACCGCC

TCACAGGTTCCGATGTCAACTTGTTGGCTGAAAACCTACTGTCCCCAGAG

GATATGGTTCTCTTCCACAACCTCACCCAGCCAAGAGGAGTGAACTGGTG

TGAGAGGACCACCCTGAGCAATGGCGGCTGCCAGTATCTGTGCCTCCCTG

CCCCGCAGATCAACCCCCACTCGCCCAAGTTTACCTGCGCCTGCCCGGAC

GGCATGCTGCTGGCCAGGGACATGAGGAGCTGCCTCACAGAGGCTGAGGC

TGCAGTGGCCACCCAGGAGACATCCACCGTCAGGCTAAAGGTCAGCTCCA

CAGCCGTAAGGACACAGCACACAACCACCCGACCTGTTCCCGACACCTCC

CGGCTGCCTGGGGCCACCCCTGGGCTCACCACGGTGGAGATAGTGACAAT

GTCTCACCAAGCTCTGGGCGACGTTGCTGGCAGAGGAAATGAGAAGAAGC

CCAGTAGCGTGAGGGCTCTGTCCATTGTCCTCCCCATCGTGCTCCTCGTC

TTCCTTTGCCTGGGGGTCTTCCTTCTATGGAAGAACTGGCGGCTTAAGAA

CATCAACAGCATCAACTTTGACAACCCCGTCTATCAGAAGACCACAGAGG

ATGAGGTCCACATTTGCCACAACCAGGACGGCTACAGCTACCCCTCGAGA

CAGATGGTCAGTCTGGAGGATGACGTGGCGTGA
```

LDLR Protein Sequence

```
                                            (SEQ ID NO: 2)
MGPWGWKLRWTVALLLAAAGTAVGDRCERNEFQCQDGKCISYKWVCDGSA

ECQDGSDESQETCLSVTCKSGDFSCGGRVNRCIPQFWRCDGQVDCDNGSD

EQGCPPKTCSQDEFRCHDGKCISRQFVCDSDRDCLDGSDEASCPVLTCGP

ASFQCNSSTCIPQLWACDNDPDCEDGSDEWPQRCRGLYVFQGDSSPCSAF

EFHCLSGECIHSSWRCDGGPDCKDKSDEENCAVATCRPDEFQCSDGNCIH

GSRQCDREYDCKDMSDEVGCVNVTLCEGPNKFKCHSGECITLDKVCNMAR

DCRDWSDEPIKECGTNECLDNNGGCSHVCNDLKIGYECLCPDGFQLVAQR

RCEDIDECQDPDTCSQLCVNLEGGYKCQCEEGFQLDPHTKACKAVGSIAY

LFFTNRHEVRKMTLDRSEYTSLIPNLRNVVALDTEVASNRIYWSDLSQRM

ICSTQLDRAHGVSSYDTVISRDIQAPDGLAVDWIHSNIYWTDSVLGTVSV

ADTKGVKRKTLFRENGSKPRAIVVDPVHGFMYWTDWGTPAKIKKGGLNGV

DIYSLVTENIQWPNGITLDLLSGRLYWVDSKLHSISSIDVNGGNRKTILE

DEKRLAHPFSLAVFEDKVFWTDIINEAIFSANRLTGSDVNLLAENLLSPE

DMVLFHNLTQPRGVNWCERTTLSNGGCQYLCLPAPQINPHSPKFTCACPD

GMLLARDMRSCLTEAEAAVATQETSTVRLKVSSTAVRTQHTTTRPVPDTS

RLPGATPGLTTVEIVTMSHQALGDVAGRGNEKKPSSVRALSIVLPIVLLV
```

-continued
FLCLGVFLLWKNWRLKNINSINFDNPVYQKTTEDEVHICHNQDGYSYPSR

QMVSLEDDVA

LRP

LRP, also known as LRP1, alpha-2-macroglobulin receptor (A2MR), apolipoprotein E receptor (APOER), and cluster of differentiation 91 (CD91), is a protein forming a receptor found in the plasma membrane of cells involved in receptor-mediated endocytosis. In humans, the LRP protein is encoded by the LRP1 gene. LRP is highly expressed in the liver, the target of HBV infection. Moreover, LRP shows polarized distribution on basolateral membrane of hepatocytes (facing blood). Several examples of LRP are highlighted below in Table 2.

TABLE 2

The LRP orthologs from three different species along with their GenBank RefSeq Accession Numbers.

| Species | Nucleic Acid | Amino Acid | GeneID |
|---|---|---|---|
| Homo sapiens | NM_002332.2 | NP_002323.2 | 4035 |
| Mus musculus | NM_008512.2 | NP_032538.2 | 16971 |
| Rattus norvegicus | NM_001130490.1 | NP_001123962.1 | 299858 |

In one example, LRP can be encoded by a 13635 base pair sequence found on chromosome 12 of the human genome (SEQ ID NO:3). The protein, as shown below, is 4544 residues long (SEQ ID NO:4).

LRP Nucleic Acid Sequence (SEQ ID NO: 3)
ATGCTGACCCCGCCGTTGCTCCTGCTGCTGCCCCTGCTCTCAGCTCTGGT

CGCGGCGGCTATCGACGCCCCTAAGACTTGCAGCCCCAAGCAGTTTGCCT

GCAGAGATCAAATAACCTGTATCTCAAAGGGCTGGCGGTGCGACGGTGAG

AGGGACTGCCCAGACGGATCTGACGAGGCCCCTGAGATTTGTCCACAGAG

TAAGGCCCAGCGATGCCAGCCAAACGAGCATAACTGCCTGGGTACTGAGC

TGTGTGTTCCCATGTCCCGCCTCTGCAATGGGGTCCAGGACTGCATGGAC

GGCTCAGATGAGGGGCCCCACTGCCGAGAGCTCCAAGGCAACTGCTCTCG

CCTGGGCTGCCAGCACCATTGTGTCCCCACACTCGATGGGCCCACCTGCT

ACTGCAACAGCAGCTTTCAGCTTCAGGCAGATGGCAAGACCTGCAAAGAT

TTTGATGAGTGCTCAGTGTACGGCACCTGCAGCCAGCTATGCACCAACAC

AGACGGCTCCTTCATATGTGGCTGTGTTGAAGGATACCTCCTGCAGCCGG

ATAACCGCTCCTGCAAGGCCAAGAACGAGCCAGTAGACCGGCCCCCTGTG

CTGTTGATAGCCAACTCCCAGAACATCTTGGCCACGTACCTGAGTGGGGC

CCAGGTGTCTACCATCACACCTACGAGCACGCGGCAGACCACAGCCATGG

ACTTCAGCTATGCCAACGAGACCGTATGCTGGGTGCATGTTGGGGACAGT

GCTGCTCAGACGCAGCTCAAGTGTGCCCGCATGCCTGGCCTAAAGGGCTT

CGTGGATGAGCACACCATCAACATCTCCCTCAGTCTGCACCACGTGGAAC

AGATGGCCATCGACTGGCTGACAGGCAACTTCTACTTTGTGGATGACATC

GATGATAGGATCTTTGTCTGCAACAGAAATGGGGACACATGTGTCACATT

GCTAGACCTGGAACTCTACAACCCCAAGGGCATTGCCCTGGACCCTGCCA

TGGGGAAGGTGTTTTTCACTGACTATGGGCAGATCCCAAAGGTGGAACGC

TGTGACATGGATGGGCAGAACCGCACCAAGCTCGTCGACAGCAAGATTGT

GTTTCCTCATGGCATCACGCTGGACCTGGTCAGCCGCCTTGTCTACTGGG

CAGATGCCTATCTGGACTATATTGAAGTGGTGGACTATGAGGGCAAGGGC

CGCCAGACCATCATCCAGGGCATCCTGATTGAGCACCTGTACGGCCTGAC

TGTGTTTGAGAATTATCTCTATGCCACCAACTCGGACAATGCCAATGCCC

AGCAGAAGACGAGTGTGATCCGTGTGAACCGCTTTAACAGCACCGAGTAC

CAGGTTGTCACCCGGGTGGACAAGGGTGGTGCCCTCCACATCTACCACCA

GAGGCGTCAGCCCCGAGTGAGGAGCCATGCCTGTGAAAACGACCAGTATG

GGAAGCCGGGTGGCTGCTCTGACATCTGCCTGCTGGCCAACAGCCACAAG

GCGCGGACCTGCCGCTGCCGTTCCGGCTTCAGCCTGGGCAGTGACGGGAA

GTCATGCAAGAAGCCGGAGCATGAGCTGTTCCTCGTGTATGGCAAGGGCC

GGCCAGGCATCATCCGGGGCATGGATATGGGGGCCAAGGTCCCGGATGAG

CACATGATCCCCATTGAAAACCTCATGAACCCCCGAGCCCTGGACTTCCA

CGCTGAGACCGGCTTCATCTACTTTGCCGACACCACCAGCTACCTCATTG

GCCGCCAGAAGATTGATGGCACTGAGCGGGAGACCATCCTGAAGGACGGC

ATCCACAATGTGGAGGGTGTGGCCGTGGACTGGATGGGAGACAATCTGTA

CTGGACGGACGATGGGCCCAAAAAGACAATCAGCGTGGCCAGGCTGGAGA

AAGCTGCTCAGACCCGCAAGACTTTAATCGAGGGCAAAATGACACACCCC

AGGGCTATTGTGGTGGATCCACTCAATGGGTGGATGTACTGGACAGACTG

GGAGGAGGACCCCAAGGACAGTCGGCGTGGGCGGCTGGAGAGGGCGTGGA

TGGATGGCTCACACCGAGACATCTTTGTCACCTCCAAGACAGTGCTTTGG

CCCAATGGGCTAAGCCTGGACATCCCGGCTGGGCGCCTCTACTGGGTGGA

TGCCTTCTACGACCGCATCGAGACGATACTGCTCAATGGCACAGACCGGA

AGATTGTGTATGAAGGTCCTGAGCTGAACCACGCCTTTGGCCTGTGTCAC

CATGGCAACTACCTCTTCTGGACTGAGTATCGGAGTGGCAGTGTCTACCG

CTTGGAACGGGGTGTAGGAGGCGCACCCCCCACTGTGACCCTTCTGCGCA

GTGAGCGGCCCCCCATCTTTGAGATCCGAATGTATGATGCCCAGCAGCAG

CAAGTTGGCACCAACAAATGCCGGGTGAACAATGGCGGCTGCAGCAGCCT

GTGCTTGGCCACCCCTGGGAGCCGCCAGTGCGCCTGTGCTGAGGACCAGG

TGTTGGACGCAGACGGCGTCACTTGCTTGGCGAACCCATCCTACGTGCCT

CCACCCCAGTGCCAGCCAGGCGAGTTTGCCTGTGCCAACAGCCGCTGCAT

CCAGGAGCGCTGGAAGTGTGACGGAGACAACGATTGCCTGGACAACAGTG

ATGAGGCCCCAGCCCTCTGCCATCAGCACACCTGCCCCTCGGACCGATTC

AAGTGCGAGAACAACCGGTGCATCCCCAACCGCTGGCTCTGCGACGGGGA

CAATGACTGTGGGAACAGTGAAGATGAGTCCAATGCCACTTGTTCAGCCC

GCACCTGCCCCCCAACCAGTTCTCCTGTGCCAGTGGCCGCTGCATCCCC

ATCTCCTGGACGTGTGATCTGGATGACGACTGTGGGGACCGCTCTGATGA

GTCTGCTTCGTGTGCCTATCCCACCTGCTTCCCCCTGACTCAGTTTACCT

GCAACAATGGCAGATGTATCAACATCAACTGGAGATGCGACAATGACAAT

GACTGTGGGGACAACAGTGACGAAGCCGGCTGCAGCCACTCCTGTTCTAG

-continued

CACCCAGTTCAAGTGCAACAGCGGGCGTTGCATCCCCGAGCACTGGACCT
GCGATGGGGACAATGACTGCGGAGACTACAGTGATGAGACACACGCCAAC
TGCACCAACCAGGCCACGAGGCCCCCTGGTGGCTGCCACACTGATGAGTT
CCAGTGCCGGCTGGATGGACTATGCATCCCCCTGCGGTGGCGCTGCGATG
GGGACACTGACTGCATGGACTCCAGCGATGAGAAGAGCTGTGAGGGAGTG
ACCCACGTCTGCGATCCCAGTGTCAAGTTTGGCTGCAAGGACTCAGCTCG
GTGCATCAGCAAAGCGTGGGTGTGTGATGGCGACAATGACTGTGAGGATA
ACTCGGACGAGGAGAACTGCGAGTCCCTGGCCTGCAGGCCACCCTCGCAC
CCTTGTGCCAACAACACCTCAGTCTGCCTGCCCCTGACAAGCTGTGTGA
TGGCAACGACGACTGTGGCGACGGCTCAGATGAGGGCGAGCTCTGCGACC
AGTGCTCTCTGAATAACGGTGGCTGCAGCCACAACTGCTCAGTGGCACCT
GGCGAAGGCATTGTGTGTTCCTGCCCTCTGGGCATGGAGCTGGGGCCCGA
CAACCACACCTGCCAGATCCAGAGCTACTGTGCCAAGCATCTCAAATGCA
GCCAAAAGTGCGACCAGAACAAGTTCAGCGTGAAGTGCTCCTGCTACGAG
GGCTGGGTCCTGGAACCTGACGGCGAGAGCTGCCGCAGCCTGGACCCCTT
CAAGCCGTTCATCATTTTCTCCAACCGCCATGAAATCCGGCGCATCGATC
TTCACAAAGGAGACTACAGCGTCCTGGTGCCCGGCCTGCGCAACACCATC
GCCCTGGACTTCCACCTCAGCCAGAGCGCCCTCTACTGGACCGACGTGGT
GGAGGACAAGATCTACCGCGGGAAGCTGCTGGACAACGGAGCCCTGACTA
GTTTCGAGGTGGTGATTCAGTATGCCTGGCCACACCCGAGGGCCTGGCT
GTAGACTGGATTGCAGGCAACATCTACTGGGTGGAGAGTAACCTGGATCA
GATCGAGGTGGCCAAGCTGGATGGACCCTCCGGACCACCCTGCTGGCCG
GTGACATTGAGCACCCAAGGGCAATCGCACTGGATCCCCGGGATGGGATC
CTGTTTTGGACAGACTGGGATGCCAGCCTGCCCCGCATTGAGGCAGCCTC
CATGAGTGGGGCTGGGCGCCGCACCGTGCACCGGGAGACCGGCTCTGGGG
GCTGGCCCAACGGGCTCACCGTGGACTACCTGGAGAAGCGCATCCTTTGG
ATTGACGCCAGGTCAGATGCCATTTACTCAGCCCGTTACGACGGCTCTGG
CCACATGGAGGTGCTTCGGGGACACGAGTTCCTGTCGCACCCGTTTGCAG
TGACGCTGTACGGGGGGAGGTCTACTGGACTGACTGGCGAACAAACACA
CTGGCTAAGGCCAACAAGTGGACCGGCCACAATGTCACCGTGGTACAGAG
GACCAACACCCAGCCCTTTGACCTGCAGGTGTACCACCCCTCCCGCCAGC
CCATGGCTCCCAATCCCTGTGAGGCCAATGGGGGCCAGGGCCCCTGCTCC
CACCTGTGTCTCATCAACTACAACCGGACCGTGTCCTGCGCCTGCCCCCA
CCTCATGAAGCTCCACAAGGACAACACCACCTGCTATGAGTTTAAGAAGT
TCCTGCTGTACGCACGTCAGATGGAGATCCGAGGTGTGGACCTGGATGCT
CCCTACTACAACTACATCATCTCCTTCACGGTGCCCGACATCGACAACGT
CACAGTGCTAGACTACGATGCCCGCGAGCAGCGTGTGTACTGGTCTGACG
TGCGGACACAGGCCATCAAGCGGGCCTTCATCAACGGCACAGGCGTGGAG
ACAGTCGTCTCTGCAGACTTGCCAAATGCCCACGGGCTGGCTGTGGACTG
GGTCTCCCGAAACCTGTTCTGGACAAGCTATGACACCAATAAGAAGCAGA

-continued

TCAATGTGGCCCGGCTGGATGGCTCCTTCAAGAACGCAGTGGTGCAGGGC
CTGGAGCAGCCCCATGGCCTTGTCGTCCACCCTCTGCGTGGGAAGCTCTA
CTGGACCGATGGTGACAACATCAGCATGGCCAACATGGATGGCAGCAATC
GCACCCTGCTCTTCAGTGGCCAGAAGGGCCCCGTGGGCCTGGCTATTGAC
TTCCCTGAAAGCAAACTCTACTGGATCAGCTCCGGGAACCATACCATCAA
CCGCTGCAACCTGGATGGGAGTGGGCTGGAGGTCATCGATGCCATGCGGA
GCCAGCTGGGCAAGGCCACCGCCCTGGCCATCATGGGGGACAAGCTGTGG
TGGGCTGATCAGGTGTCGGAAAAGATGGGCACATGCAGCAAGGCTGACGG
CTCGGGCTCCGTGGTCCTTCGGAACAGCACCACCCTGGTGATGCACATGA
AGGTCTATGACGAGAGCATCCAGCTGGACCATAAGGGCACCAACCCCTGC
AGTGTCAACAACGGTGACTGCTCCCAGCTCTGCCTGCCCACGTCAGAGAC
GACCCGCTCCTGCATGTGCACAGCCGGCTATAGCCTCCGGAGTGGCCAGC
AGGCCTGCGAGGGCGTAGGTTCCTTTCTCCTGTACTCTGTGCATGAGGGA
ATCAGGGGAATTCCCCTGGATCCCAATGACAAGTCAGATGCCCTGGTCCC
AGTGTCCGGGACCTCGCTGGCTGTCGGCATCGACTTCCACGCTGAAAATG
ACACCATCTACTGGGTGGACATGGGCCTGAGCACGATCAGCCGGGCCAAG
CGGGACCAGACGTGGCGTGAAGACGTGGTGACCAATGGCATTGGCCGTGT
GGAGGGCATTGCAGTGGACTGGATCGCAGGCAACATCTACTGGACAGACC
AGGGCTTTGATGTCATCGAGGTCGCCCGGCTCAATGGCTCCTTCCGCTAC
GTGGTGATCTCCCAGGGTCTAGACAAGCCCCGGGCCATCACCGTCCACCC
GGAGAAAGGGTACTTGTTCTGGACTGAGTGGGGTCAGTATCCGCGTATTG
AGCGGTCTCGGCTAGATGGCACGGAGCGTGTGGTGCTGGTCAACGTCAGC
ATCAGCTGGCCCAACGGCATCTCAGTGGACTACCAGGATGGGAAGCTGTA
CTGGTGCGATGCACGGACAGACAAGATTGAACGGATCGACCTGGAGACAG
GTGAGAACCGCGAGGTGGTTCTGTCCAGCAACAACATGGACATGTTTTCA
GTGTCTGTGTTTGAGGATTTCATCTACTGGAGTGACAGGACTCATGCCAA
CGGCTCTATCAAGCGCGGGAGCAAAGACAATGCCACAGACTCCGTGCCCC
TGCGAACCGGCATCGGCGTCCAGCTTAAAGACATCAAAGTCTTCAACCGG
GACCGGCAGAAAGGCACCAACGTGTGCGCGGTGGCCAATGGCGGGTGCCA
GCAGCTGTGCCTGTACCGGGGCCGTGGGCAGCGGGCCTGCGCCTGTGCCC
ACGGGATGCTGGCTGAAGACGGAGCATCGTGCCGCGAGTATGCCGGCTAC
CTGCTCTACTCAGAGCGCACCATTCTCAAGAGTATCCACCTGTCGGATGA
GCGCAACCTCAATGCGCCCGTGCAGCCCTTCGAGGACCCTGAGCACATGA
AGAACGTCATCGCCCTGGCCTTTGACTACCGGGCAGGCACCTCTCCGGGC
ACCCCCAATCGCATCTTCTTCAGCGACATCCACTTTGGGAACATCCAACA
GATCAACGACGATGGCTCCAGGAGGATCACCATTGTGGAAAACGTGGGCT
CCGTGGAAGGCCTGGCCTATCACCGTGGCTGGGACACTCTCTATTGGACA
AGCTACACGACATCCACCATCACGCGCCACACAGTGGACCAGACCCGCCC
AGGGGCCTTCGAGCGTGAGACCGTCATCACTATGTCTGGAGATGACCACC
CACGGGCCTTCGTTTTGGACGAGTGCCAGAACCTCATGTTCTGGACCAAC
TGGAATGAGCAGCATCCCAGCATCATGCGGGCGGCGCTCTCGGGAGCCAA

-continued

TGTCCTGACCCTTATCGAGAAGGACATCCGTACCCCCAATGGCCTGGCCA
TCGACCACCGTGCCGAGAAGCTCTACTTCTCTGACGCCACCCTGGACAAG
ATCGAGCGGTGCGAGTATGACGGCTCCCACCGCTATGTGATCCTAAAGTC
AGAGCCTGTCCACCCCTTCGGGCTGGCCGTGTATGGGGAGCACATTTTCT
GGACTGACTGGGTGCGGCGGGCAGTGCAGCGGGCCAACAAGCACGTGGGC
AGCAACATGAAGCTGCTGCGCGTGGACATCCCCAGCAGCCCATGGGCAT
CATCGCCGTGGCCAACGACACCAACAGCTGTGAACTCTCTCCATGCCGAA
TCAACAACGGTGGCTGCCAGGACCTGTGTCTGCTCACTCACCAGGGCCAT
GTCAACTGCTCATGCCGAGGGGCCGAATCCTCCAGGATGACCTCACCTG
CCGAGCGGTGAATTCCTCTTGCCGAGCACAAGATGAGTTTGAGTGTGCCA
ATGGCGAGTGCATCAACTTCAGCCTGACCTGCGACGGCGTCCCCCACTGC
AAGGACAAGTCCGATGAGAAGCCATCCTACTGCAACTCCCGCCGCTGCAA
GAAGACTTTCCGGCAGTGCAGCAATGGGCGCTGTGTGTCCAACATGCTGT
GGTGCAACGGGGCCGACGACTGTGGGGATGGCTCTGACGAGATCCCTTGC
AACAAGACAGCCTGTGGTGTGGGCGAGTTCCGCTGCCGGGACGGGACCTG
CATCGGGAACTCCAGCCGCTGCAACCAGTTTGTGGATTGTGAGGACGCCT
CAGATGAGATGAACTGCAGTGCCACCGACTGCAGCAGCTACTTCCGCCTG
GGCGTGAAGGGCGTGCTCTTCCAGCCCTGCGAGCGGACCTCACTCTGCTA
CGCACCCAGCTGGGTGTGTGATGGCGCCAATGACTGTGGGGACTACAGTG
ATGAGCGCGACTGCCCAGGTGTGAAACGCCCCAGATGCCCTCTGAATTAC
TTCGCCTGCCCTAGTGGGCGCTGCATCCCCATGAGCTGGACGTGTGACAA
AGAGGATGACTGTGAACATGGCGAGGACGAGACCCACTGCAACAAGTTCT
GCTCAGAGGCCCAGTTTGAGTGCCAGAACCATCGCTGCATCTCCAAGCAG
TGGCTGTGTGACGGCAGCGATGACTGTGGGGATGGCTCAGACGAGGCTGC
TCACTGTGAAGGCAAGACGTGCGGCCCCTCCTCCTTCTCCTGCCCTGGCA
CCCACGTGTGCGTCCCGAGCGCTGGCTCTGTGACGGTGACAAAGACTGT
GCTGATGGTGCAGACGAGAGCATCGCAGCTGGTTGCTTGTACAACAGCAC
TTGTGACGACCGTGAGTTCATGTGCCAGAACCGCCAGTGCATCCCCAAGC
ACTTCGTGTGTGACCACGACCGTGACTGTGCAGATGGCTCTGATGAGTCC
CCCGAGTGTGAGTACCCGACCTGCGGCCCCAGTGAGTTCCGCTGTGCCAA
TGGGCGCTGTCTGAGCTCCCGCCAGTGGGAGTGTGATGGCGAGAATGACT
GCCACGACCAGAGTGACGAGGCTCCCAAGAACCCACACTGCACCAGCCAA
GAGCACAAGTGCAATGCCTCGTCACAGTTCCTGTGCAGCAGTGGGCGCTG
TGTGGCTGAGGCACTGCTCTGCAACGGCCAGGATGACTGTGGCGACAGCT
CGGACGAGCGTGGCTGCCACATCAATGAGTGTCTCAGCCGCAAGCTCAGT
GGCTGCAGCCAGGACTGTGAGGACCTCAAGATCGGCTTCAAGTGCCGCTG
TCGCCCTGGCTTCCGGCTGAAGGACGACGGCCGGACGTGTGCTGATGTGG
ACGAGTGCAGCACCACCTTCCCCTGCAGCCAGCGCTGCATCAACACTCAT
GGCAGCTATAAGTGTCTGTGTGTGGAGGGCTATGCACCCCGCGGCGGCGA
CCCCCACAGCTGCAAGGCTGTGACTGACGAGGAACCGTTTCTGATCTTCG

CCAACCGGTACTACCTGCGCAAGCTCAACCTGGACGGGTCCAACTACACG
TTACTTAAGCAGGGCCTGAACAACGCCGTTGCCTTGGATTTTGACTACCG
AGAGCAGATGATCTACTGGACAGATGTGACCACCCAGGGCAGCATGATCC
GAAGGATGCACCTTAACGGGAGCAATGTGCAGGTCCTACACCGTACAGGC
CTCAGCAACCCCGATGGGCTGGCTGTGGACTGGGTGGGTGGCAACCTGTA
CTGGTGCGACAAAGGCCGGGACACCATCGAGGTGTCCAAGCTCAATGGGG
CCTATCGGACGGTGCTGGTCAGCTCTGGCCTCCGTGAGCCCAGGGCTCTG
GTGGTGGATGTGCAGAATGGGTACCTGTACTGGACAGACTGGGGTGACCA
TTCACTGATCGGCCGCATCGGCATGGATGGGTCCAGCCGCAGCGTCATCG
TGGACACCAAGATCACATGGCCCAATGGCCTGACGCTGGACTATGTCACT
GAGCGCATCTACTGGGCCGACGCCCGCGAGGACTACATTGAATTTGCCAG
CCTGGATGGCTCCAATCGCCACGTTGTGCTGAGCCAGGACATCCCGCACA
TCTTTGCACTGACCCTGTTTGAGGACTACGTCTACTGGACCGACTGGGAA
ACAAAGTCCATTAACCGAGCCCACAAGACCACGGGCACCAACAAAACGCT
CCTCATCAGCACGCTGCACCGGCCCATGGACCTGCATGTCTTCCATGCCC
TGCGCCAGCCAGACGTGCCCAATCACCCCTGCAAGGTCAACAATGGTGGC
TGCAGCAACCTGTGCCTGCTGTCCCCGGGGAGGGCACAAATGTGCCTG
CCCCACCAACTTCTACCTGGGCAGCGATGGGCGCACCTGTGTGTCCAACT
GCACGGCTAGCCAGTTTGTATGCAAGAACGACAAGTGCATCCCCTTCTGG
TGGAAGTGTGACACCGAGGACGACTGCGGGGACCACTCAGACGAGCCCCC
GGACTGCCCTGAGTTCAAGTGCCGGCCCGGACAGTTCCAGTGCTCCACAG
GTATCTGCACAAACCCTGCCTTCATCTGCGATGGCGACAATGACTGCCAG
GACAACAGTGACGAGGCCAACTGTGACATCCACGTCTGCTTGCCCAGTCA
GTTCAAATGCACCAACACCAACCGCTGTATTCCCGGCATCTTCCGCTGCA
ATGGGCAGGACAACTGCGGGAGATGGGAGGATGAGAGGGACTGCCCCGAG
GTGACCTGCGCCCCAACCAGTTCCAGTGCTCCATTACCAAACGGTGCAT
CCCCCGGGTCTGGGTCTGCGACCGGGACAATGACTGTGTGGATGGCAGTG
ATGAGCCCGCCAACTGCACCCAGATGACCTGTGGTGTGGACGAGTTCCGC
TGCAAGGATTCGGGCCGCTGCATCCCAGCGCGTTGGAAGTGTGACGGAGA
GGATGACTGTGGGGATGGCTCGGATGAGCCCAAGGAAGAGTGTGATGAAC
GCACCTGTGAGCCATACCAGTTCCGCTGCAAGAACAACCGCTGCGTGCCC
GGCCGCTGGCAGTGCGACTACGACAACGATTGCGGTGACAACTCCGATGA
AGAGAGCTGCACCCCTCGGCCCTGCTCCGAGAGTGAGTTCTCCTGTGCCA
ACGGCCGCTGCATCGCGGGGCGCTGGAAATGCGATGGAGACCACGACTGC
GCGGACGGCTCGGACGAGAAAGACTGCACCCCCCGCTGTGACATGGACCA
GTTCCAGTGCAAGAGCGGCCACTGCATCCCCCTGCGCTGGCGCTGTGACG
CAGACGCCGACTGCATGGACGGCAGCGACGAGGAGGCCTGCGGCACTGGC
GTGCGGACCTGCCCCCTGGACGAGTTCCAGTGCAACAACACCTTGTGCAA
GCCGCTGGCCTGGAAGTGCGATGGCGAGGATGACTGTGGGGACAACTCAG
ATGAGAACCCCGAGGAGTGTGCCCGGTTCGTGTGCCCTCCCAACCGGCCC
TTCCGTTGCAAGAATGACCGCGTCTGTCTGTGGATCGGGCGCCAATGCGA

-continued

```
TGGCACGGACAACTGTGGGGATGGGACTGATGAAGAGGACTGTGAGCCCC
CCACAGCCCACACCACCCACTGCAAAGACAAGAAGGAGTTTCTGTGCCGG
AACCAGCGCTGCCTCTCCTCCTCCCTGCGCTGCAACATGTTCGATGACTG
CGGGGACGGCTCTGACGAGGAGGACTGCAGCATCGACCCCAAGCTGACCA
GCTGCGCCACCAATGCCAGCATCTGTGGGGACGAGGCACGCTGCGTGCGC
ACCGAGAAAGCGGCCTACTGTGCCTGCCGCTCGGGCTTCCACACCGTGCC
CGGCCAGCCCGGATGCCAAGACATCAACGAGTGCCTGCGCTTCGGCACCT
GCTCCCAGCTCTGCAACAACACCAAGGGCGGCCACCTCTGCAGCTGCGCT
CGGAACTTCATGAAGACGCACAACACCTGCAAGGCCGAAGGCTCTGAGTA
CCAGGTCCTGTACATCGCTGATGACAATGAGATCCGCAGCCTGTTCCCCG
GCCACCCCCATTCGGCTTACGAGCAGGCATTCCAGGGTGACGAGAGTGTC
CGCATTGATGCTATGGATGTCCATGTCAAGGCTGGCCGTGTCTATTGGAC
CAACTGGCACACGGGCACCATCTCCTACCGCAGCCTGCCACCTGCTGCGC
CTCCTACCACTTCCAACCGCCACCGGCGACAGATTGACCGGGGTGTCACC
CACCTCAACATTTCAGGGCTGAAGATGCCCAGAGGCATCGCCATCGACTG
GGTGGCCGGAAACGTGTACTGGACCGACTCGGGCCAGATGTGATTGAGG
TGGCGCAGATGAAGGGCGAGAACCGCAAGACGCTCATCTCGGGCATGATT
GACGAGCCCCACGCCATTGTGGTGGACCCACTGAGGGGGACCATGTACTG
GTCAGACTGGGGCAACCACCCCAAGATTGAGACGGCAGCGATGGATGGGA
CGCTTCGGGAGACACTGGTGCAGGACAACATTCAGTGGCCCACAGGCCTG
GCCGTGGATTATCACAATGAGCGGCTGTACTGGGCAGACGCCAAGCTTTC
AGTCATCGGCAGCATCCGGCTCAATGGCACGGACCCCATTGTGGCTGCTG
ACAGCAAACGAGGCCTAAGTCACCCCTTCAGCATCGACGTCTTTGAGGAT
TACATCTATGGTGTCACCTACATCAATAATCGTGTCTTCAAGATCCATAA
GTTTGGCCACAGCCCCTTGGTCAACCTGACAGGGGGCCTGAGCCACGCCT
CTGACGTGGTCCTTTACCATCAGCACAAGCAGCCCGAAGTGACCAACCCA
TGTGACCGCAAGAAATGCGAGTGGCTCTGCCTGCTGAGCCCCAGTGGGCC
TGTCTGCACCTGTCCCAATGGGAAGCGGCTGGACAACGGCACATGCGTGC
CTGTGCCCTCTCCAACGCCCCCCCCAGATGCTCCCCGGCCTGGAACCTGT
AACCTGCAGTGCTTCAACGGTGGCAGCTGTTTCCTCAATGCACGGAGGCA
GCCCAAGTGCCGCTGCCAACCCCGCTACACGGGTGACAAGTGTGAACTGG
ACCAGTGCTGGGAGCACTGTCGCAATGGGGCACCTGTGCTGCCTCCCCC
TCTGGCATGCCCACGTGCCGGTGCCCCACGGGCTTCACGGGCCCCAAATG
CACCCAGCAGGTGTGTGCGGGCTACTGTGCCAACAACAGCACCTGCACTG
TCAACCAGGGCAACCAGCCCCAGTGCCGATGCCTACCCGGCTTCCTGGGC
GACCGCTGCCAGTACCGGCAGTGCTCTGGCTACTGTGAGAACTTTGGCAC
ATGCCAGATGGCTGCTGATGGCTCCCGACAATGCCGCTGCACTGCCTACT
TTGAGGGATCGAGGTGTGAGGTGAACAAGTGCAGCCGCTGTCTCGAAGGG
GCCTGTGTGGTCAACAAGCAGAGTGGGGATGTCACCTGCAACTGCACGGA
TGGCCGGGTGGCCCCCAGCTGTCTGACCTGCGTCGGCCACTGCAGCAATG
GCGGCTCCTGTACCATGAACAGCAAAATGATGCCTGAGTGCCAGTGCCCA
CCCCACATGACAGGGCCCCGGTGTGAGGAGCACGTCTTCAGCCAGCAGCA
GCCAGGACATATAGCCTCCATCCTAATCCCTCTGCTGTTGCTGCTGCTGC
TGGTTCTGGTGGCCGGAGTGGTATTCTGGTATAAGCGGCGAGTCCAAGGG
GCTAAGGGCTTCCAGCACCAACGGATGACCAACGGGGCCATGAACGTGGA
GATTGGAAACCCCACCTACAAGATGTACGAAGGCGGAGAGCCTGATGATG
TGGGAGGCCTACTGGACGCTGACTTTGCCCTGGACCCTGACAAGCCCACC
AACTTCACCAACCCCGTGTATGCCACACTCTACATGGGGGGCCATGGCAG
TCGCCACTCCCTGGCCAGCACGGACGAGAAGCGAGAACTCCTGGGCCGGG
GCCCTGAGGACGAGATAGGGGACCCCTTGGCATAG
```

LRP Protein Sequence (SEQ ID NO: 4)

```
MLTPPLLLLLPLLSALVAAAIDAPKTCSPKQFACRDQITCISKGWRCDGE
RDCPDGSDEAPEICPQSKAQRCQPNEHNCLGTELCVPMSRLCNGVQDCMD
GSDEGPHCRELQGNCSRLGCQHHCVPTLDGPTCYCNSSFQLQADGKTCKD
FDECSVYGTCSQLCTNTDGSFICGCVEGYLLQPDNRSCKAKNEPVDRPPV
LLIANSQNILATYLSGAQVSTITPTSTRQTTAMDFSYANETVCWVHVGDS
AAQTQLKCARMPGLKGFVDEHTINISLSLHHVEQMAIDWLTGNFYFVDDI
DDRIFVCNRNGDTCVTLLDLELYNPKGIALDPAMGKVFFTDYGQIPKVER
CDMDGQNRTKLVDSKIVFPHGITLDLVSRLVYWADAYLDYIEVVDYEGKG
RQTIIQGILIEHLYGLTVFENYLYATNSDNANAQQKTSVIRVNRFNSTEY
QVVTRVDKGGALHIYHQRRQPRVRSHACENDQYGKPGGCSDICLLANSHK
ARTCRCRSGFSLGSDGKSCKKPEHELFLVYGKGRPGIIRGMDMGAKVPDE
HMIPIENLMNPRALDFHAETGFIYFADTTSYLIGRQKIDGTERETILKDG
IHNVEGVAVDWMGDNLYWTDDGPKKTISVARLEKAAQTRKTLIEGKMTHP
RAIVVDPLNGWMYWTDWEEDPKDSRRGRLERAWMDGSHRDIFVTSKTVLW
PNGLSLDIPAGRLYWVDAFYDRIETILLNGTDRKIVYEGPELNHAFGLCH
HGNYLFWTEYRSGSVYRLERGVGGAPPTVTLLRSERPPIFEIRMYDAQQQ
QVGTNKCRVNNGGCSSLCLATPGSRQCACAEDQVLDADGVTCLANPSYVP
PPQCQPGEFACANSRCIQERWKCDGDNDCLDNSDEAPALCHQHTCPSDRF
KCENNRCIPNRWLCDGDNDCGNSEDESNATCSARTCPPNQFSCASGRCIP
ISWTCDLDDDCGDRSDESASCAYPTCFPLTQFTCNNGRCININWRCDNDN
DCGDNSDEAGCSHSCSSTQFKCNSGRCIPEHWTCDGDNDCGDYSDETHAN
CTNQATRPPGGCHTDEFQCRLDGLCIPLRWRCDGDTDCMDSSDEKSCEGV
THVCDPSVKFGCKDSARCISKAWVCDGDNDCEDNSDEENCESLACRPPSH
PCANNTSVCLPPDKLCDGNDDCGDGSDEGELCDQCSLNNGGCSHNCSVAP
GEGIVCSCPLGMELGPDNHTCQIQSYCAKHLKCSQKCDQNKFSVKCSCYE
GWVLEPDGESCRSLDPFKPFIIFSNRHEIRRIDLHKGDYSVLVPGLRNTI
ALDPHLSQSALYWTDVVEDKIYRGKLLDNGALTSFEVVIQYGLATPEGLA
VDWIAGNIYWVESNLDQIEVAKLDGTLRTTLLAGDIEHPRAIALDPRDGI
```

LFWTDWDASLPRIEAASMSGAGRRTVHRETGSGGWPNGLTVDYLEKRILW

IDARSDAIYSARYDGSGHMEVLRGHEFLSHPFAVTLYGGEVYWTDWRTNT

LAKANKWTGHNVTVVQRTNTQPFDLQVYHPSRQPMAPNPCEANGGQGPCS

HLCLINYNRTVSCACPHLMKLHKDNTTCYEFKKFLLYARQMEIRGVDLDA

PYYNYIISFTVPDIDNVTVLDYDAREQRVYWSDVRTQAIKRAFINGTGVE

TVVSADLPNAHGLAVDWVSRNLFWTSYDTNKKQINVARLDGSFKNAVVQG

LEQPHGLVVHPLRGKLYWTDGDNISMANMDGSNRTLLFSGQKGPVGLAID

FPESKLYWISSGNHTINRCNLDGSGLEVIDAMRSQLGKATALAIMGDKLW

WADQVSEKMGTCSKADGSGSVVLRNSTTLVMHMKVYDESIQLDHKGTNPC

SVNNGDCSQLCLPTSETTRSCMCTAGYSLRSGQQACEGVGSFLLYSVHEG

IRGIPLDPNDKSDALVPVSGTSLAVGIDFHAENDTIYWVDMGLSTISRAK

RDQTWREDVVTNGIGRVEGIAVDWIAGNIYWTDQGFDVIEVARLNGSFRY

VVISQGLDKPRAITVHPEKGYLFWTEWGQYPRIERSRLDGTERVVLVNVS

ISWPNGISVDYQDGKLYWCDARTDKIERIDLETGENREVVLSSNNMDMFS

VSVFEDFIYWSDRTHANGSIKRGSKDNATDSVPLRTGIGVQLKDIKVFNR

DRQKGTNVCAVANGGCQQLCLYRGRGQRACACAHGMLAEDGASCREYAGY

LLYSERTILKSIHLSDERNLNAPVQPFEDPEHMKNVIALAFDYRAGTSPG

TPNRIFFSDIHFGNIQQINDDGSRRITIVENVGSVEGLAYHRGWDTLYWT

SYTTSTITRHTVDQTRPGAFERETVITMSGDDHPRAFVLDECQNLMFWTN

WNEQHPSIMRAALSGANVLTLIEKDIRTPNGLAIDHRAEKLYFSDATLDK

IERCEYDGSHRYVILKSEPVHPFGLAVYGEHIFWTDWVRRAVQRANKHVG

SNMKLLRVDIPQQPMGIIAVANDTNSCELSPCRINNGGCQDLCLLTHQGH

VNCSCRGGRILQDDLTCRAVNSSCRAQDEFECANGECINFSLTCDGVPHC

KDKSDEKPSYCNSRRCKKTFRQCSNGRCVSNMLWCNGADDCGDGSDEIPC

NKTACGVGEFRCRDGTCIGNSSRCNQFVDCEDASDEMNCSATDCSSYFRL

GVKGVLFQPCERTSLCYAPSWVCDGANDCGDYSDERDCPGVKRPRCPLNY

FACPSGRCIPMSWTCDKEDDCEHGEDETHCNKFCSEAQFECQNHRCISKQ

WLCDGSDDCGDGSDEAAHCEGKTCGPSSFSCPGTHVCVPERWLCDGDKDC

ADGADESIAAGCLYNSTCDDREFMCQNRQCIPKHFVCDHDRDCADGSDES

PECEYPTCGPSEFRCANGRCLSSRQWECDGENDCHDQSDEAPKNPHCTSQ

EHKCNASSQFLCSSGRCVAEALLCNGQDDCGDSSDERGCHINECLSRKLS

GCSQDCEDLKIGFKCRCRPGFRLKDDGRTCADVDECSTTFPCSQRCINTH

GSYKCLCVEGYAPRGGDPHSCKAVTDEEPFLIFANRYYLRKLNLDGSNYT

LLKQGLNNAVALDFDYREQMIYWTDVTTQGSMIRRMHLNGSNVQVLHRTG

LSNPDGLAVDWVGGNLYWCDKGRDTIEVSKLNGAYRTVLVSSGLREPRAL

VVDVQNGYLYWTDWGDHSLIGRIGMDGSSRSVIVDTKITWPNGLTLDYVT

ERIYWADAREDYIEFASLDGSNRHVVLSQDIPHIFALTLFEDYVYWTDWE

TKSINRAHKTTGTNKTLLISTLHRPMDLHVFHALRQPDVPNHPCKVNNGG

CSNLCLLSPGGGHKCACPTNFYLGSDGRTCVSNCTASQFVCKNDKCIPFW

WKCDTEDDCGDHSDEPPDCPEFKCRPGQFQCSTGICTNPAFICDGDNDCQ

DNSDEANCDIHVCLPSQFKCTNTNRCIPGIFRCNGQDNCGDGEDERDCPE

VTCAPNQFQCSITKRCIPRVWVCDRDNDCVDGSDEPANCTQMTCGVDEFR

CKDSGRCIPARWKCDGEDDCGDGSDEPKEECDERTCEPYQFRCKNNRCVP

GRWQCDYDNDCGDNSDEESCTPRPCSESEFSCANGRCIAGRWKCDGDHDC

ADGSDEKDCTPRCDMDQFQCKSGHCIPLRWRCDADADCMDGSDEEACGTG

VRTCPLDEFQCNNTLCKPLAWKCDGEDDCGDNSDENPEECARFVCPPNRP

FRCKNDRVCLWIGRQCDGTDNCGDGTDEEDCEPPTAHTTHCKDKKEFLCR

NQRCLSSSLRCNMFDDCGDGSDEEDCSIDPKLTSCATNASICGDEARCVR

TEKAAYCACRSGFHTVPGQPGCQDINECLRFGTCSQLCNNTKGGHLCSCA

RNFMKTHNTCKAEGSEYQVLYIADDNEIRSLFPGHPHSAYEQAFQGDESV

RIDAMDVHVKAGRVYWTNWHTGTISYRSLPPAAPPTTSNRHRRQIDRGVT

HLNISGLKMPRGIAIDWVAGNVYWTDSGRDVIEVAQMKGENRKTLISGMI

DEPHAIVVDPLRGTMYWSDWGNHPKIETAAMDGTLRETLVQDNIQWPTGL

AVDYHNERLYWADAKLSVIGSIRLNGTDPIVAADSKRGLSHPFSIDVFED

YIYGVTYINNRVFKIHKFGHSPLVNLTGGLSHASDVVLYHQHKQPEVTNP

CDRKKCEWLCLLSPSGPVCTCPNGKRLDNGTCVPVPSPTPPPDAPRPGTC

NLQCFNGGSCFLNARRQPKCRCQPRYTGDKCELDQCWEHCRNGGTCAASP

SGMPTCRCPTGFTGPKCTQQVCAGYCANNSTCTVNQGNQPQCRCLPGFLG

DRCQYRQCSGYCENFGTCQMAADGSRQCRCTAYFEGSRCEVNKCSRCLEG

ACVVNKQSGDVTCNCTDGRVAPSCLTCVGHCSNGGSCTMNSKMMPECQCP

PHMTGPRCEEHVFSQQQPGHIASILIPLLLLLLLVLVAGVVFWYKRRVQG

AKGFQHQRMTNGAMNVEIGNPTYKMYEGGEPDDVGGLLDADFALDPDKPT

NFTNPVYATLYMGGHGSRHSLASTDEKRELLGRGPEDEIGDPLA

RAP

Receptor associated protein (RAP) or low density lipoprotein receptor-related protein associated protein 1 (LRPAP1) is a chaperone protein that is encoded in humans by the LRPAP1 gene. LRPAP1 is involved with trafficking of certain members of the LDL receptor family including LRP and LRP2. It is a glycoprotein that binds to LRP, as well as to other members of the LDLR family. It acts to inhibit binding of all known ligands for these receptors, and may prevent receptor aggregation and degradation in the endoplasmic reticulum, thereby acting as a molecular chaperone. It may be under the regulatory control of calmodulin, since it is able to bind calmodulin and be phosphorylated by calmodulin-dependent kinase II. Several examples of RAP are highlighted below in Table 3.

TABLE 3

The RAP orthologs from three different species along with their GenBank RefSeq Accession Numbers.

| Species | Nucleic Acid | Amino Acid | GeneID |
| --- | --- | --- | --- |
| Homo sapiens | NM_002337.3 | NP_002328.1 | 4043 |
| Mus musculus | NM_013587.2 | NP_038615.2 | 16976 |
| Rattus norvegicus | NM_001169113.1 | NP_001162584.1 | 116565 |

In one example, RAP can be encoded by a 1074 base pair sequence found on chromosome 4 of the human genome (SEQ ID NO:5). The protein, as shown below, is 357 residues long (SEQ ID NO:6).

RAP Nucleic Acid Sequence (SEQ ID NO: 5)
ATGGCGCCGCGGAGGGTCAGGTCGTTTCTGCGCGGGCTCCCGGCGCTGCT

ACTGCTGCTGCTCTTCCTCGGGCCCTGGCCCGCTGCGAGCCACGGCGGCA

AGTACTCGCGGGAGAAGAACCAGCCCAAGCCGTCCCCGAAACGCGAGTCC

GGAGAGGAGTTCCGCATGGAGAAGTTGAACCAGCTGTGGGAGAAGGCCCA

GCGACTGCATCTTCCTCCCGTGAGGCTGGCCGAGCTCCACGCTGATCTGA

AGATACAGGAGAGGGACGAACTCGCCTGGAAGAAACTAAAGCTTGACGGC

TTGGACGAAGATGGGGAGAAGGAAGCGAGACTCATACGCAACCTCAATGT

CATCTTGGCCAAGTATGGTCTGGACGGAAAGAAGGACGCTCGGCAGGTGA

CCAGCAACTCCCTCAGTGGCACCCAGGAAGACGGGCTGGATGACCCCAGG

CTGGAAAAGCTGTGGCACAAGGCGAAGACCTCTGGGAAATTCTCCGGCGA

AGAACTGGACAAGCTCTGGCGGGAGTTCCTGCATCACAAAGAGAAAGTTC

ACGAGTACAACGTCCTGCTGGAGACCCTGAGCAGGACCGAAGAAATCCAC

GAGAACGTCATTAGCCCCTCGGACCTGAGCGACATCAAGGGCAGCGTCCT

GCACAGCAGGCACACGGAGCTGAAGGAGAAGCTGCGCAGCATCAACCAGG

GCCTGGACCGCCTGCGCAGGGTCAGCCACCAGGGCTACAGCACTGAGGCT

GAGTTCGAGGAGCCCAGGGTGATTGACCTGTGGGACCTGGCGCAGTCCGC

CAACCTCACGGACAAGGAGCTGGAGGCGTTCCGGGAGGAGCTCAAGCACT

TCGAAGCCAAAATCGAGAAGCACAACCACTACCAGAAGCAGCTGGAGATT

GCGCACGAGAAGCTGAGGCACGCAGAGAGCGTGGGCGACGGCGAGCGTGT

GAGCCGCAGCCGCGAGAAGCACGCCCTGCTGGAGGGGCGGACCAAGGAGC

TGGGCTACACGGTGAAGAAGCATCTGCAGGACCTGTCCGGCAGGATCTCC

AGAGCTCGGCACAACGAACTCTGA

RAP Protein Sequence (SEQ ID NO: 6)
MAPRRVRSFLRGLPALLLLLLFLGPWPAASHGGKYSREKNQPKPSPKRES

GEEFRMEKLNQLWEKAQRLHLPPVRLAELHADLKIQERDELAWKKLKLDG

LDEDGEKEARLIRNLNVILAKYGLDGKKDARQVTSNSLSGTQEDGLDDPR

LEKLWHKAKTSGKFSGEELDKLWREFLHHKEKVHEYNVLLETLSRTEEIH

ENVISPSDLSDIKGSVLHSRHTELKEKLRSINQGLDRLRRVSHQGYSTEA

EFEEPRVIDLWDLAQSANLTDKELEAFREELKHFEAKIEKHNHYQKQLEI

AHEKLRHAESVGDGERVSRSREKHALLEGRTKELGYTVKKHLQDLSGRIS

RARHNEL

FXa

Factor Xa (thrombokinase, known eponymously as Stuart-Prower factor) is the activated form of the coagulation factor X (FX). Factor Xa (FXa) is an enzyme, a serine endopeptidase, which plays a key role at several stages of the coagulation system. Factor X is synthesized in the liver. The most commonly used anticoagulants in clinical practice, warfarin and the heparin series of anticoagulants and fondaparinux, act to inhibit the action of FXa in various degrees. Several examples of FX are highlighted below in Table 4.

TABLE 4

The FXa orthologs from three different species along with their GenBank RefSeq Accession Numbers.

| Species | Nucleic Acid | Amino Acid | GeneID |
|---|---|---|---|
| Homo sapiens | NM_000504.3 | NP_000495.1 | 2159 |
| Mus musculus | NM_001242368.1 | NP_001229297.1 | 14058 |
| Rattus norvegicus | BC088151.1 | AAH88151.1 | 29243 |

FXa can cleave the L envelope protein present on the surface of HBV. Moreover, a 7-aa antistasin-related peptide (Tuszynski et al., J Biol Chem 262:9718-23, 1987; Nutt et al., J Biol Chem 263:10162-7, 1988), a direct FXa inhihbitor, can block HBV infection of HepaRG cells, demonstrating that L protein cleavage by FXa is critical for HBV infectivity. Cleavage of the L protein switches HBV binding from HSPG, the low-affinity HBV receptor, to a high-affinity HBV receptor, e.g., LDLR or LRP.

Accordingly, FXa inhibitors can be used to treat HBV infection or to reduce a risk of a HBV infection. In some aspects of the methods described herein, the 7-aa antistasin related peptide (or antistasin itself) can be used to inhibit or reduce HBV infection. Since FXa is a key enzyme in the blood coagulation cascade, many small molecular inhibitors exist that can be utilized in the present methods. For example, tick anticoagulant peptide (TAP), fondaparinux, draparinux, rivaroxaban, apixaban, betrixaban, edoxaban, otamixaban, or any combination thereof can be used in the methods described herein.

Therapeutic Proteins, Nucleic Acids, Vectors, and Host Cells

In one aspect, the invention includes nucleic acids encoding LDLR, LRP, and RAP polypeptides, fragments, and variants thereof. A nucleic acid sequence encoding an exemplary LDLR polypeptide is provided in SEQ ID NO:1. The amino acid sequence encoded by SEQ ID NO:1 is provided in SEQ ID NO:2. A nucleic acid sequence encoding an exemplary LRP is provided in SEQ ID NO:3. The amino acid sequence encoded by SEQ ID NO:3 is provided in SEQ ID NO:4. A nucleic acid sequence encoding an exemplary RAP is provided in SEQ ID NO:5. The amino acid sequence encoded by SEQ ID NO:5 is provided in SEQ ID NO:6.

LDLR, LRP, and RAP nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "isolated nucleic acid" means a nucleic acid, e.g., DNA or RNA, that is not immediately contiguous with both of the coding sequences with which it is immediately contiguous (one on the 5' end and one on the 3' end) in the naturally occurring genome of the organism from which it is derived. Thus, in one embodiment, an isolated LDLR, LRP, or RAP nucleic acid includes some or all of the 5' non-coding (e.g., promoter) sequences that are immediately contiguous to the LDLR, LRP, or RAP nucleic acid coding sequence, respectively. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment)

independent of other sequences. It also includes a recombinant DNA that is part of a hybrid gene encoding an additional polypeptide sequence.

The invention includes vectors, preferably expression vectors, containing a nucleic acid that encodes the proteins described herein. As used herein, the term "vector" refers to a nucleic acid molecule capable of transporting another nucleic acid to which it has been linked and can include, e.g., a plasmid, cosmid, or viral vector. The vector can autonomously replicate or it can integrate into a host cell's DNA. Viral vectors include, e.g., replication-defective retroviruses, adenoviruses, and adeno-associated viruses.

A vector can include a LDLR, LRP, or RAP nucleic acid in a form suitable for expression of the nucleic acid in a host cell. Preferably a recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce LDLR, LRP, or RAP polypeptides encoded by nucleic acids as described herein.

The recombinant expression vectors of the invention can be designed for expression of LDLR, LRP, or RAP polypeptides in prokaryotic or eukaryotic cells. For example, polypeptides of the invention can be expressed in *E. coli*, insect cells (e.g., using baculovirus expression vectors), yeast cells, or mammalian cells (e.g., CHO or COS cells). Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, Gene 67:31-40, 1988), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

One can maximize recombinant protein expression in *E. coli* by expressing the protein in host bacteria with an impaired capacity to proteolytically cleave the recombinant protein (Gottesman (1990) Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in *E. coli* (Wada et al., Nucleic Acids Res 20:2111-2118, 1992). Such alteration of nucleic acid sequences of the invention can be carried out by standard DNA synthesis techniques.

Modified versions of peptides disclosed herein are referred to as "peptide derivatives," and they can also be used in the new methods. For example, peptide derivatives of a peptide can be used instead of that peptide in therapeutic methods described herein. Peptides disclosed herein can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., J. Biol. Chem. 278:45746, 2003. In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β$^3$-amino acids"), phosphorous analogs of amino acids, such as α-amino phosphonic acids and α-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

The term "purified" refers to a LDLR, LRP, or RAP nucleic acid (or LDLR, LRP, or RAP polypeptide) that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

In some embodiments, the invention includes nucleic acid sequences that are substantially identical to a LDLR, LRP, or RAP nucleic acid. A nucleic acid sequence that is "substantially identical" to a LDLR nucleic acid has at least 90% identity (e.g., at least about 92%, 95%, 96%, 97%, 98%, 99%, or identical) to the LDLR nucleic acid sequence represented by SEQ ID NO:1. A nucleic acid sequence that is "substantially identical" to a LRP nucleic acid has at least 90% identity (e.g., at least about 92%, 95%, 96%, 97%, 98%, 99%, or identical) to the LRP nucleic acid sequence represented by SEQ ID NO:3. A nucleic acid sequence that is "substantially identical" to a RAP nucleic acid has at least 90% identity (e.g., at least about 92%, 95%, 96%, 97%, 98%, 99%, or identical) to the RAP nucleic acid sequence represented by SEQ ID NO:5. For purposes of comparison of nucleic acids, the length of the reference nucleic acid sequence will be at least 50 nucleotides, but can be longer, e.g., at least 60 or more nucleotides.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). The two sequences may be of the same length.

The percent identity or homology between two sequences can be determined using a mathematical algorithm. A non-limiting example of a mathematical algorithm utilized for the comparison of two sequences is the algorithm of Karlin and Altschul, Proc. Natl. Acad. Sci. USA 87:2264-2268, 1990, modified as in Karlin and Altschul, Proc. Natl. Acad. Sci. USA 90:5873-5877, 1993. Such an algorithm is incorporated into the NBLAST and XBLAST programs of Altschul et al., J Mol Biol 215:403-410, 1990. BLAST nucleotide searches can be performed with the NBLAST program, score=100, wordlength=12 to obtain nucleotide sequences homologous to LDLR, LRP, or RAP nucleic acid molecules of the invention. BLAST protein searches can be performed with the XBLAST program, score=50, wordlength=3 to obtain amino acid sequences homologous to LDLR, LRP, and RAP protein molecules of the invention. To obtain gapped alignments for comparison purposes, Gapped BLAST can be utilized as described in Altschul et al., Nucleic Acids Res. 25:3389-3402, 1997. When utilizing BLAST and Gapped BLAST programs, the default parameters of the respective programs (e.g., XBLAST and NBLAST) can be used. See online at ncbi.nlm.nih.gov.

In other embodiments, the invention includes variants, homologs, and/or fragments of certain LDLR, LRP, or RAP nucleic acids, e.g., variants, homologs, and/or fragments of the LDLR, LRP, or RAP nucleic acid sequences represented by SEQ ID NOs:1, 3, and 5, respectively. The terms "variant" or "homolog" in relation to LDLR, LRP, or RAP nucleic acids include any substitution, variation, modification, replacement, deletion, or addition of one (or more) nucleotides from or to the sequence of a LDLR, LRP, or RAP nucleic acid. The resultant nucleotide sequence may encode an LDLR, LRP, or RAP polypeptide that has at least 50% of a biological activity (e.g., binding to histone mRNAs) of the referenced LDLR, LRP, or RAP polypeptides, respectively (e.g., SEQ ID NOs:2, 4, and 6, respectively). In particular, the term "homolog" covers homology with respect to structure and/or function as long as the resultant nucleotide sequence encodes or is capable of encoding a LDLR, LRP, or RAP polypeptide that has at least 50% of the biological activity of LDLR, LRP, or RAP encoded by a sequence shown herein as SEQ ID NO:1, 3, and 5, respectively. With respect to sequence homology, there is at least about 90% (e.g., at least about 92%, 95%, 96%, 97%, 98%, 99%, or 100%) homology to the sequence shown as SEQ ID NO:1, 3, and 5, respectively. The term "homology" as used herein can be equated with the term "identity."

"Substantial homology" or "substantially homologous," where homology indicates sequence identity, means at least 90% identical (e.g., at least about 92%, 95%, 96%, 97%, 98%, or 99%) sequence identity, as judged by direct sequence alignment and comparison. "Substantial homology" when assessed by the BLAST algorithm equates to sequences which match with an EXPECT value of at least about 7, e.g., at least about 9, 10, or more. The default threshold for EXPECT in BLAST searching is usually 10.

Also included within the scope of the present invention are certain alleles of certain LDLR, LRP, or RAP genes. As used herein, an "allele" or "allelic sequence" is an alternative form of LDLR, LRP, or RAP. Alleles can result from changes in the nucleotide sequence, and generally produce altered mRNAs or polypeptides whose structure or function may or may not be altered. Any given gene can have none, one, or more than one allelic form. Common changes that give rise to alleles are generally ascribed to deletions, additions, or substitutions of amino acids. Each of these types of changes can occur alone, or in combination with the others, one or more times in a given sequence.

The invention also includes nucleic acids that hybridize, e.g., under stringent hybridization conditions (as defined herein) to all or a portion of the nucleotide sequences represented by SEQ ID NOs:1, 3, and 5, or complements thereof. The hybridizing portion of the hybridizing nucleic acids is typically at least 15 (e.g., 20, 30, or 50) nucleotides in length. The hybridizing portion of the hybridizing nucleic acid is at least about 90%, e.g., at least about 92%, 95%, 96%, 97%, 98%, 99%, or 100%, identical to the sequence of a portion or all of a nucleic acid encoding a LDLR, LRP, or RAP polypeptide, or to its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO:1, 3, or 5, are considered "antisense oligonucleotides."

High stringency conditions are hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Also included in the invention are genetic constructs (e.g., vectors and plasmids) that include a LDLR, LRP, or RAP nucleic acid described herein, operably linked to a transcription and/or translation sequence to enable expression, e.g., expression vectors. A selected nucleic acid, e.g., a DNA molecule encoding a LDLR, LRP, or RAP polypeptide, is "operably linked" to another nucleic acid molecule, e.g., a promoter, when it is positioned either adjacent to the other molecule or in the same or other location such that the other molecule can control transcription and/or translation of the selected nucleic acid. Such constructs are useful for, for example, gene therapy to treat a subject against HBV infection, e.g., reduce a risk of a HBV infection in a subject and treat a subject infected with HBV. Skilled practitioners will understand that soluble forms of LDLR, LRP, and RAP can be expressed and secreted from cells to interact with HBV.

Also included in the invention are various engineered cells, e.g., transformed host cells, which contain a LDLR, LRP, or RAP nucleic acid described herein. A transformed cell is a cell into which (or into an ancestor of which) has been introduced, by means of recombinant DNA techniques, a nucleic acid encoding a LDLR, LRP, or RAP polypeptide. Both prokaryotic and eukaryotic cells are included. Mammalian cells transformed with a LDLR, LRP, or RAP nucleic acid can include host cells for an attaching enteric organism, e.g., intestinal cells, HeLa cells, and mouse embryonic fibroblasts. Prokaryotic cells can include bacteria, e.g., *Escherichia coli*. An engineered cell exemplary of the type included in the invention is an *E. coli* strain that expresses LDLR, LRP, or RAP.

Certain LDLR, LRP, and RAP polypeptides are also included within the present invention. Examples of such polypeptides are LDLR, LRP, and RAP polypeptides and fragments, such as the one shown as SEQ ID NOs:2, 4, and 6. Also included within the present invention are certain fragments of LDLR, LRP, and RAP polypeptides, e.g., fragments of LDLR, LRP, and RAP polypeptides may include at least one mRNA binding domain, or other useful portion of a full-length LDLR, LRP, or RAP polypeptide. For example, useful fragments of LDLR, LRP, or RAP polypeptides include, but are not limited to, fragments having mRNA binding activity, and portions of such fragments.

The terms "protein" and "polypeptide" both refer to any chain of amino acids, regardless of length or post-translational modification (e.g., glycosylation or phosphorylation). Thus, the terms "protein" and "polypeptide" include full-length naturally occurring isolated proteins, as well as recombinantly or synthetically produced polypeptides that correspond to the full-length naturally occurring proteins, or to a fragment of the full-length naturally occurring or synthetic polypeptide.

Fragments of a protein can be produced by any of a variety of methods known to those skilled in the art, e.g., recombinantly, by proteolytic digestion, and/or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

A purified or isolated compound is a composition that is at least 80% by weight the compound of interest, e.g., a LDLR, LRP, or RAP polypeptide. In general, the preparation is at least 90% (e.g., at least about 92%, 95%, 96%, 97%, 98%, 99%, or 100%) by weight the compound of interest. Purity can be measured by any appropriate standard method, e.g., column chromatography, polyacrylamide gel electrophoresis, or HPLC analysis.

In certain embodiments, LDLR, LRP, and RAP polypeptides include sequences substantially identical to all or portions of naturally occurring LDLR, LRP, and RAP polypeptides. Polypeptides "substantially identical" to the LDLR, LRP, and RAP polypeptide sequences described herein have an amino acid sequence that is at least 90% (e.g., at least about 92%, 95%, 96%, 97%, 98%, 99%, or 100%), identical to the amino acid sequences of the LDLR, LRP, and RAP polypeptides represented by SEQ ID NOs:2, 4, and 6, respectively (measured as described herein). For purposes of comparison, the length of the reference LDLR, LRP, and RAP polypeptide sequence is at least 50 amino acids, e.g., at least 60 or 80 amino acids, or the entire length of the wild-type sequence.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide that is 50% identical to the reference polypeptide over its entire length.

LDLR, LRP, and RAP polypeptides of the invention include, but are not limited to, recombinant polypeptides and natural polypeptides. Also included are nucleic acid sequences that encode forms of LDLR, LRP, or RAP polypeptides in which naturally occurring amino acid sequences are altered or deleted. Certain nucleic acids of the present invention may encode polypeptides that are soluble under normal physiological conditions.

Antibodies to LDLR, LRP, and FXa

Antibodies can be produced that bind to LDLR, LRP, or FXa. For example, an antibody can bind to LDLR, LRP, or FXa and reduce or inhibit LDLR, LRP, and FXa activity. The term "antibody" as used herein refers to an immunoglobulin molecule or immunologically active portion thereof, i.e., an antigen-binding fragment. Examples of immunologically active portions of immunoglobulin molecules include F(ab') and F(ab')$_2$ fragments, which retain the ability to bind antigen. Such fragments can be obtained commercially, or using methods known in the art. For example, F(ab')$_2$ fragments can be generated by treating the antibody with an enzyme such as pepsin, a non-specific endopeptidase that normally produces one F(ab')$_2$ fragment and numerous small peptides of the Fc portion. The resulting F(ab')$_2$ fragment is composed of two disulfide-connected Fab units. The Fc fragment is extensively degraded and can be separated from the F(ab')$_2$ by dialysis, gel filtration or ion exchange chromatography. F(ab') fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,000 Dalton Fc fragment; to isolate the F(ab') fragments, the Fc fragments can be removed, e.g., by affinity purification using protein A/G. A number of kits are available commercially for generating F(ab') fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to a Fc receptor, e.g., it has a mutagenized or deleted Fc receptor binding region. The antibody can be coupled to a toxin or imaging agent.

Methods for making suitable antibodies are known in the art. A full-length protein or antigenic peptide fragment thereof can be used as an immunogen, or can be used to identify antibodies made with other immunogens, e.g., cells, membrane preparations, and the like, e.g., E rosette positive purified normal human peripheral T cells, as described in U.S. Pat. Nos. 4,361,549 and 4,654,210.

Methods for making monoclonal antibodies are known in the art. Basically, the process involves obtaining antibody-secreting immune cells (lymphocytes) from the spleen of a mammal (e.g., mouse) that has been previously immunized with the antigen of interest (e.g., a cancer-related antigen) either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein (Nature 256:495, 1975), which is hereby incorporated by reference.

Mammalian lymphocytes are immunized by in vivo immunization of the animal (e.g., a mouse) with a cancer-related antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by known techniques, for example, using polyethylene glycol ("PEG") or other fusing agents (See, Milstein and Kohler, Eur J Immunol 6:511, 1976, which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. Typically, such antibodies can be raised by administering the protein or polypeptide of the present invention subcutaneously to New Zealand white rabbits that have first been bled to obtain pre-immune serum. The antigens can be injected at a total volume of 100:1 per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/kg IV. This and other procedures for raising polyclonal antibodies are disclosed in E. Harlow, et. al., editors, Antibodies: A Laboratory Manual (1988).

In addition to utilizing whole antibodies, the invention encompasses the use of binding portions of such antibodies. Such binding portions include Fab fragments, F(ab')$_2$ fragments, and Fv fragments. These antibody fragments can be made by conventional procedures, such as proteolytic fragmentation procedures, as described in J. Goding, Monoclonal Antibodies: Principles and Practice, pp. 98-118 (N.Y. Academic Press 1983).

Chimeric, humanized, de-immunized, or completely human antibodies are desirable for applications which include repeated administration, e.g., therapeutic treatment of human subjects.

Chimeric antibodies generally contain portions of two different antibodies, typically of two different species. Generally, such antibodies contain human constant regions and variable regions from another species, e.g., murine variable regions. For example, mouse/human chimeric antibodies have been reported which exhibit binding characteristics of the parental mouse antibody, and effector functions associated with the human constant region. See, e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al., Cancer Research, 47:999, 1987). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line. Such chimeric antibodies have been used in human therapy.

Humanized antibodies are known in the art. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al., Proc Natl Acad Sci USA 81:6801, 1984; Morrison and Oi, Adv Immunol 44:65, 1988) (which preserves the ligand-binding properties, but which also retains the immunogenicity of the nonhuman variable domains); (b) by grafting only the nonhuman CDRs onto human framework and constant regions with or without retention of critical framework residues (Jones et al., Nature 321:522, 1986; Verhoeyen et al., Science 239:1539, 1988); or (c) by transplanting the entire nonhuman variable domains (to preserve ligand-binding properties) but also "cloaking" them with a human-like surface through judicious replacement of exposed residues (to reduce antigenicity) (Padlan, Molec Immunol 28:489, 1991).

Humanization by CDR grafting typically involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al., Nature 332:323, 1988; Queen et al., Proc Natl Acad Sci USA 86:10,029, 1989). The framework residues which need to be preserved can be identified by computer modeling. Alternatively, critical framework residues may potentially be identified by comparing known antibody combining site structures (Padlan, Mol Immun 31(3):169-217, 1994). The invention also includes partially humanized antibodies, in which the 6 CDRs of the heavy and light chains and a limited number of structural amino acids of the murine monoclonal antibody are grafted by recombinant technology to the CDR-depleted human IgG scaffold (Jones et al., Nature 321:522-525, 1986).

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody (Biovation, Aberdeen, Scotland).

The antibody can also be a single chain antibody. A single-chain antibody (scFV) can be engineered (see, for example, Colcher et al., Ann NY Acad Sci 880:263-80, 1999; and Reiter, Clin Cancer Res 2:245-52, 1996). The single chain antibody can be dimerized or multimerized to generate multivalent antibodies having specificities for different epitopes of the same target protein. In some embodiments, the antibody is monovalent, e.g., as described in Abbs et al., Ther Immunol 1(6):325-31, 1994, incorporated herein by reference.

Antibodies to LDLR, LRP, and FXa are also commercially available. For example, antibodies to LDLR are available from Santa Cruz Biotechnology (sc-20744). Anti-LRP antibodies are available from EMD Millipore (438192, 438190); and R&D (AF2369). Antibodies to FXa are available from R&D (MAB1063). These antibodies can be modified as known in the art and disclosed herein, e.g., humanized or deimmunized.

Inhibitory Nucleic Acids

Nucleic acid molecules (e.g., RNA molecules) can be used to inhibit (i.e., reduce) LDLR and/or LRP expression or activity. A LDLR inhibitor or LRP inhibitor can be a siRNA, antisense RNA, a ribozyme, or aptamer that can specifically reduce the expression of LDLR or LRP, respectively. In some aspects, a cell or subject can be treated with a compound that reduces the expression of LDLR and/or LRP. Such approaches include oligonucleotide-based therapies such as RNA interference, antisense, ribozymes, and aptamers. Exemplary inhibitory nucleic acids to LDLR and LRP are described below.

LDLR shRNA: Sigma NM_000527

```
TRCN0000056517:
                                          (SEQ ID NO: 7)
CCGGACAGAGGATGAGGTCCACATTCTCGAGAATGTGGACCTCATCCTCT

GTTTTTTG

TRCN0000262146:
                                          (SEQ ID NO: 8)
CCGGGGGCGACAGATGCGAAAGAAACTCGAGTTTCTTTCGCATCTGTCGC

CCTTTTTG

TRCN0000262148:
                                          (SEQ ID NO: 9)
CCGGACATCAACAGCATCAACTTTGCTCGAGCAAAGTTGATGCTGTTGAT

GTTTTTTG

TRCN0000262149:
                                         (SEQ ID NO: 10)
CCGGATGGAAGAACTGGCGGCTTAACTCGAGTTAAGCCGCCAGTTCTTCC

ATTTTTTG

TRCN0000282124:
                                         (SEQ ID NO: 11)
CCGGGATGAAGTTGGCTGCGTTAATCTCGAGATTAACGCAGCCAACTTCA

TCTTTTTG
```

LRP1 shRNA: Sigma NM_002332

```
TRCN0000053255:
                                         (SEQ ID NO: 12)
CCGGCGGAGTGGTATTCTGGTATAACTCGAGTTATACCAGAATACCACTC

CGTTTTTG

TRCN0000053257:
                                         (SEQ ID NO: 13)
CCGGCCGCGAGGACTACATTGAATTCTCGAGAATTCAATGTAGTCCTCGC

GGTTTTTG
```

-continued

TRCN0000219021:
(SEQ ID NO: 14)
GTACCGGACATCGATGATAGGATCTTTGCTCGAGCAAAGATCCTATCATC
GATGTTTTTTG

TRCN0000230615
(SEQ ID NO: 15)
CCGGGATGCCTATCTGGACTATATTCTCGAGAATATAGTCCAGATAGGCA
TCTTTTTG

TRCN0000257134:
(SEQ ID NO: 16)
CCGGACAGCTTCCTGAGGGCTAATTCTCGAGAATTAGCCCTCAGGAAGCT
GTTTTTTG i. siRNA Molecules RNA interference (RNAi) is a process whereby double-stranded RNA (dsRNA, also referred to herein as siRNAs or ds siRNAs, for double-stranded small interfering RNAs) induces the sequence-specific degradation of homologous mRNA in animals and plant cells (Hutvagner and Zamore, Curr Opin Genet Dev 12:225-232, 2002; Sharp, Genes Dev 15:485-490, 2001). In mammalian cells, RNAi can be triggered by 21-nucleotide (nt) duplexes of small interfering RNA (siRNA) (Chiu et al., Mol Cell 10:549-561, 2002; Elbashir et al., Nature 411:494-498, 2001), or by micro-RNAs (miRNA), functional small-hairpin RNA (shRNA), or other dsRNAs which are expressed in vivo using DNA templates with RNA polymerase III promoters (Zeng et al., Mol Cell 9:1327-1333, 2002; Paddison et al., Genes Dev 16:948-958, 2002; Lee et al., Nature Biotechnol 20:500-505, 2002; Paul et al., Nature Biotechnol 20:505-508, 2002; Tuschl, Nature Biotechnol 20:440-448, 2002; Yu et al., Proc Natl Acad Sci USA 99:6047-6052, 2002; McManus et al., RNA 8:842-850, 2002; Sui et al., Proc Natl Acad Sci USA 99:5515-5520, 2002).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 92%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl 2002, supra) capable of expressing functional double-stranded siRNAs; (Bagella et al., J Cell Physiol 177:206-213, 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Miyagishi et al., 2002, supra; Paul et al., 2002, supra; Yu et al., 2002, supra; Sui et al., 2002, supra). Constructs containing siRNA sequence under the control of T7 promoter also make functional siRNAs when cotransfected into the cells with a vector expression T7 RNA polymerase (Jacque, 2002, supra).

ii. Antisense Nucleic Acids

An "antisense" nucleic acid can include a nucleotide sequence that is complementary to a "sense" nucleic acid encoding a protein, e.g., complementary to the coding strand of a double-stranded cDNA molecule or complementary to a LDLR or LRP mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids Res 15:6625-6641, 1987). The antisense nucleic acid molecule can also comprise a 2'-o-methylribonucleotide (Inoue et al., Nucleic Acids Res 15:6131-6148, 1987) or a chimeric RNA-DNA analogue (Inoue et al., FEBS Lett 215:327-330, 1987).

In some embodiments, the antisense nucleic acid is a morpholino oligonucleotide (see, e.g., Heasman, Dev Biol 243:209-14, 2002; Iversen, Curr Opin Mol Ther 3:235-8, 2001; Summerton, Biochim Biophys Acta 1489:141-58, 1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des 6:569-84, 1991; Helene, Ann NY Acad Sci 660:27-36, 1992; and Maher, Bioassays 14:807-15, 1992. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

iii. Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to a nucleotide sequence of a cDNA described herein, and a sequence having known catalytic sequence responsible for mRNA cleavage (see U.S. Pat. No. 5,093,246 or Haselhoff and Gerlach, Nature 334:585-591, 1988). For example, a derivative of a Tetrahymena L-19 IVS RNA can be constructed in which the nucleotide sequence of the active site is complementary to the nucleotide sequence to be cleaved in a target mRNA. See, e.g., Cech et al., U.S. Pat. Nos. 4,987,071 and 5,116,742. Alternatively, a target mRNA can be used to select a catalytic RNA having a specific ribonuclease activity from a pool of RNA molecules. See, e.g., Bartel and Szostak, Science 261:1411-1418, 1993.

iv. Aptamers

Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al., Nature 355:564-566, 1992; and U.S. Pat. No. 5,582,981, Toole et al., 1996). Methods for selection and preparation of such RNA aptamers are known in the art (see, e.g., Famulok, Curr Opin Struct Biol 9:324, 1999; Herman and Patel, J Sci 287:820-825, 2000; Kelly et al., J Mol Biol 256:417, 1996; and Feigon et al., Chem Biol 3:611, 1996).

Administration of Inhibitory Nucleic Acid Molecules

The inhibitory nucleic acid molecules described herein can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid molecules to peptides or antibodies that bind to cell surface receptors or antigens. The inhibitory nucleic acid molecules can also be delivered to cells using the vectors described herein. To achieve sufficient intracellular concentrations of the inhibitory nucleic acid molecules, vector constructs in which the inhibitory nucleic acid molecule is placed under the control of a strong promoter can be used.

A "therapeutically effective amount" is an amount sufficient to effect beneficial or desired results. For example, a therapeutically effective amount is one that achieves the desired therapeutic effect. This amount can be the same or different from a prophylactically effective amount, which is an amount necessary to reduce or inhibit a HBV infection. An effective amount can be administered in one or more administrations, applications, or dosages. A therapeutically effective amount of a composition depends on the composition selected. The compositions can be administered from one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Methods for Identifying Compounds Capable of Treating a HBV Infection

The invention provides methods for screening test compounds for an ability to treat a HBV infection or reduce a risk of a HBV infection. A "test compound" as described herein is any compound that can be screened using the methods described herein. For example, a test compound can be, e.g., a small organic or inorganic molecule (M.W. less than 1,000 Da). Alternatively or in addition, the test compound can be a polypeptide (e.g., a polypeptide having a random or predetermined amino acid sequence or a naturally-occurring or synthetic polypeptide) or a nucleic acid, such as a DNA or RNA molecule. A test compound can be naturally occurring (e.g., an herb or a natural product), or synthetic, or can include both natural and synthetic components. A test compound can have a formula weight of less than about 10,000 grams per mole, less than 5,000 grams per mole, less than 1,000 grams per mole, or less than about 500 grams per mole. The test compound can be, for example, any organic or inorganic compound (e.g., heteroorganic or organometallic compound), an amino acid, amino acid analog, polypeptide, peptidomimetic (e.g., peptoid), oligopeptide (e.g., from about 5 to about 25 amino acids in length, preferably from about 10 to 20 or 12 to 18 amino acids in length, preferably 12, 15, or 18 amino acids in length), nucleotide, nucleotide analog, polynucleotide, polynucleotide analog, ribonucleic acid, deoxyribonucleic acid, antisense oligonucleotide, ribozyme, saccharide, lipid (e.g., a sphingolipid), and/or a fatty acid, or any combination thereof.

The terms "antagonist" or "inhibitor" of HBV refer to compounds that, e.g., bind to HBV and/or LDLR, LRP, and/or FXa (e.g., a component of a HBV receptor complex)

and/or partially or totally block or inhibit HBV interaction with LDLR, LRP, and/or FXa (e.g., a component of a HBV receptor complex) as measured in known assays. Inhibitors include, e.g., antibodies directed against LDLR, LRP, or FXa, modified versions of LDLR or LRP, naturally occurring and synthetic ligands, antagonists, agonists, antibodies, small chemical molecules, and the like. Assays for detecting inhibitors or antagonists are described in more detail below.

Libraries of Test Compounds

In certain embodiments, screens of the present invention utilize libraries of test compounds. A "library" is a collection of compounds (e.g., as a mixture or as physically separated individual compounds) synthesized from various combinations of one or more starting components. At least some of the compounds must differ from at least some of the other compounds in the library. A library can include, e.g., 5, 10, 50, 100, 1000, or even 10,000, 50,000, or 100,000, or more different compounds (i.e., not simply multiple copies of the same compounds, although some compounds in the library may be duplicated or represented more than once). Each of the different compounds will be present in an amount such that its presence can be determined by some means, e.g., can be isolated, analyzed, and/or detected with a receptor or suitable probe. The actual quantity of each different compound needed so that its presence can be determined will vary due to the actual procedures used and may change as the technologies for isolation, detection, and analysis advance. When the compounds are present in a mixture in substantially equimolar amounts, for example, an amount of 100 picomoles of each compound can often be detected. Libraries can include both libraries of individual compounds (e.g., present substantially as a single type of compound-per-well, made via parallel synthesis or the pool and split pool method) and mixtures containing substantially equimolar amounts of each desired compound (i.e., wherein no single compound dominates). Either library format can allow identification of an active compound discovered in an assay.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116: 2661; U.S. Pat. Nos. 5,359,115, 5,362,899, and 5,288,514; PCT Publication Nos. WO92/10092, WO93/09668, WO91/07087, WO93/20242, and WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky, "Principles of Peptide Synthesis," 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J. Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described above.

Screening Methods

The invention provides methods for identifying compounds capable of treating a HBV infection or reducing a risk of a HBV infection. Although applicants do not intend to be bound by any particular theory as to the biological mechanism involved, such compounds are thought to modulate specifically HBV interaction with a component of the HBV receptor complex (e.g., by inhibiting or reducing binding of HBV to LDLR, LRP, and/or FXa).

In one aspect, the invention includes methods for screening test compounds to identify a compound that modulates (i.e., increases or decreases) HBsAg secretion from a cell, e.g., a hepatocyte. For example, a cell, e.g., a hepatocyte, expressing a polypeptide comprising an amino acid sequence that has at least 90% identity to SEQ ID NO:2 or 4 can be contacted with a HBV in the presence of a test compound. A level of HBsAg secretion can be determined by any art-recognized method. Exemplary assays for determining a level of HBsAg secretion are described in the Examples section, below. The level of HBsAg secretion in the presence of the test compound can be compared with the level of HBsAg secretion in the absence of the test compound, and if there is a reduced level of HBsAg secretion in the presence of the test compound than in its absence, the test compound is a candidate anti-HBV agent.

In certain aspects of the present invention, screening for such compounds is accomplished by (i) identifying from a group of test compounds those that bind to LDLR or LRP and/or modulate (i.e., increase or decrease) an interaction between LDLR and/or LRP and HBV; and, optionally, (ii) further testing such compounds for their ability to treat HBV in vitro or in vivo. Test compounds that decrease an interaction between LDLR and/or LRP with HBV are referred to herein as "candidate anti-HBV agents." Candidate anti-HBV agents further tested and found to be capable of treating or reducing a risk of a HBV infection are considered "anti-HBV agents." In the screening methods of the present invention, candidate anti-HBV agents can be, but do not necessarily have to be, tested to determine whether they are anti-HBV agents. Assays of the present invention may be carried out in biological samples, whole cell preparations, and/or ex vivo cell-free systems.

In one aspect, the invention includes methods for screening test compounds to identify compounds that bind to LDLR and/or LRP, e.g., a polypeptide comprising an amino acid sequence that has at least about 90%, e.g., at least about 92%, 95%, 96%, 97%, 98%, 99%, or 100% identity to SEQ ID NO:2 or 4. Binding of a test compound to LDLR and/or LRP can be detected, for example, in vitro, by reversibly or irreversibly immobilizing the test compound(s) or LDLR and/or LRP on a substrate, e.g., the surface of a well of a 96-well polystyrene microtiter plate. Methods for immobilizing polypeptides and other small molecules are well known in the art. For example, microtiter plates can be coated with LDLR and/or LRP by adding the polypeptide in a solution (typically, at a concentration of 0.05 to 1 mg/ml in a volume of 1-100 µl) to each well, and incubating the plates at room temperature to 37° C. for a given amount of time, e.g., for 0.1 to 36 hours. Polypeptides not bound to the plate can be removed by shaking excess solution from the plate, and then washing the plate (once or repeatedly) with water or a buffer. Typically, the polypeptide is in water or a buffer. The plate can then be washed with a buffer that lacks the bound polypeptide. To block the free protein-binding sites on the plates, plates can be blocked with a protein that is unrelated to the bound polypeptide. For example, 300 µl of bovine serum albumin (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a particle, e.g., beaded agarose or beaded sepharose, can be used as the substrate. Test compounds can then be added to the coated plate and allowed to bind to LDLR and/or LRP (e.g., at 37° C. for 0.5 to 12 hours). The plate can then be rinsed as described above. Skilled practitioners will appreciate that many variations of this method are possible. For example, the method can include coating a substrate with a test compound and adding LDLR and/or LRP to the substrate-bound compound.

Binding of LDLR and/or LRP to a test compound can be detected by any of a variety of art-known methods. For example, an antibody that specifically binds to LDLR and/or LRP (i.e., an anti-LDLR antibody or an anti-LRP antibody) can be used in an immunoassay. Antibodies useful in the methods and treatments described herein can be raised using art known methods or obtained from commercial sources. The antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of the anti-LDLR or anti-LRP antibody). In an alternative detection method, LDLR and/or LRP is labeled (e.g., with a radioisotope, fluorophore, chromophore, or the like), and the label is detected. In still another method, LDLR and/or LRP is produced as a fusion protein with a protein that can be detected optically, e.g., green fluorescent protein (which can be detected under a light source, e.g., a blue light (e.g., a 488 nm light) source or UV light source). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen or epitope that can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides (e.g., test polypeptides) that bind to LDLR and/or LRP, conventional two-hybrid assays of protein/protein interactions can be used (see e.g., Chien et al., *Proc. Natl. Acad. Sci. USA,* 88:9578, 1991; Fields et al., U.S. Pat. No. 5,283,173; Fields and Song, *Nature,* 340:245, 1989; Le Douarin et al., *Nucleic Acids Research,* 23:876, 1995; Vidal et al., *Proc. Natl. Acad. Sci. USA,* 93:10315-10320, 1996; and White, *Proc. Natl. Acad. Sci. USA,* 93:10001-10003, 1996). Generally, two-hybrid methods involve reconstitution of two separable domains of a transcription factor. One fusion protein includes LDLR or LRP fused to either a transactivator domain or DNA binding domain of a transcription factor (e.g., of Gal4). The other fusion protein contains a test polypeptide or a binding partner for the polypeptide included in the first fusion protein, fused to either the DNA binding domain or a transactivator domain of a transcription factor. Binding of LDLR or LRP to the test polypeptide or binding partner reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In still another aspect, the invention provides methods of identifying test compounds that modulate (e.g., increase or decrease) expression of LDLR or LRP. The method includes contacting a LDLR and/or LRP nucleic acid with a test compound and then measuring expression of the encoded LDLR and/or LRP polypeptide. Since the LDLR and LRP nucleic acids described herein have been identified, they can be cloned into various host cells (e.g., mammalian cells, insect cells, bacteria or fungi) for carrying out such assays in whole cells.

In certain embodiments, an isolated nucleic acid molecule encoding LDLR or LRP is used to identify a compound that modulates (e.g., increases or decreases) the expression of LDLR or LRP in vivo (e.g., in a LDLR- or LRP-producing cell). In such embodiments, cells that express LDLR or LRP are cultured, exposed to a test compound (or a mixture of test compounds), and the level of LDLR and/or LRP expression is compared with the level of LDLR and/or LRP expression or activity in cells that are otherwise identical, but have not been exposed to the test compound(s). Standard quantitative assays of gene expression can be used.

Expression of LDLR and LRP can be measured using art-known methods, for example, by Northern blot, PCR analysis, or RNAse protection analyses using a nucleic acid molecule of the invention as a probe. Other examples include enzyme-linked immunosorbent assay (ELISA), radioimmunoassay (RIA) and fluorescent activated cell sorting (FACS). The level of expression in the presence of the test molecule, compared with the level of expression in its absence, will indicate whether or not the test compound modulates the expression of LDLR or LRP.

In certain embodiments, the methods include identifying candidate compounds that interfere with steps in LDLR or LRP translational accuracy, such as maintaining a proper reading frame during translation and terminating translation at a stop codon. This method involves constructing cells in which a detectable reporter polypeptide can only be produced if the normal process of staying in one reading frame or of terminating translation at a stop codon has been disrupted. This method further involves contacting the cell with a test compound to examine whether it increases or decreases the production of the reporter polypeptide.

In other embodiments, the cell system is a cell-free extract and the method involves measuring transcription or translation in vitro. Conditions are selected so that transcription or translation of the reporter is increased or decreased by the addition of a transcription modifier or a translation modifier to the cell extract.

One method for identifying candidate compounds relies upon a transcription-responsive gene product. This method involves constructing a cell in which the production of a reporter molecule changes (i.e., increases or decreases) under conditions in which cell transcription of LDLR and/or LRP nucleic acid changes (i.e., increases or decreases). Specifically, the reporter molecule is encoded by a nucleic acid transcriptionally linked to a sequence constructed and arranged to cause a relative change in the production of the reporter molecule when transcription of LDLR or LRP nucleic acid changes. A gene sequence encoding the reporter may, for example, be fused to part or all of the gene encoding the transcription-responsive gene product and/or to part or all of the genetic elements that control the production of the gene product. Alternatively, the transcription-responsive gene product may stimulate transcription of the gene encoding the reporter, either directly or indirectly. The method further involves contacting the cell with a test compound, and determining whether the test compound increases or decreases the production of the reporter molecule in the cell.

Alternatively, the method for identifying candidate compounds can rely upon a translation-responsive gene product. This method involves constructing a cell in which cell translation of LDLR or LRP changes (i.e., increases or decreases). Specifically, the reporter molecule is encoded by a nucleic acid translationally linked to a sequence constructed and arranged to cause a relative increase or decrease in the production of the reporter molecule when transcription of LDLR or LRP nucleic acid changes. A gene sequence encoding the reporter may, for example, be fused to part or all of the gene encoding the translation-responsive gene product and/or to part or all of the genetic elements that control the production of the gene product. Alternatively, the translation-responsive gene product may stimulate translation of the gene encoding the reporter, either directly or indirectly. The method further involves contacting the cell with a test compound, and determining whether the test compound increases or decreases the production of the first reporter molecule in the cell.

For these and any method described herein, a wide variety of reporters may be used, with typical reporters providing conveniently detectable signals (e.g., by spectroscopy). By way of example, a reporter gene may encode an enzyme that catalyzes a reaction that alters light absorption properties. Examples of reporter molecules include but are not limited to β-galactosidase, invertase, green fluorescent protein, luciferase, chloramphenicol acetyltransferase, beta-glucuronidase, exo-glucanase, glucoamylase and radiolabeled reporters. For example, the production of the reporter molecule can be measured by the enzymatic activity of the reporter gene product, such as β-galactosidase.

Any of the methods described herein can be used for high throughput screening of numerous test compounds to identify candidate anti-HBV agents. By high-throughput screening is meant that the method can be used to screen a large number of candidate compounds relatively easily and quickly.

Having identified a test compound as a candidate anti-HBV agent, the compound can be further tested in vivo or in vitro using techniques known in the art to confirm whether it is an anti-HBV agent, i.e., to determine whether it can modulate HBsAg levels in vitro (e.g., using isolated cells or cell-free systems) or in vivo (e.g., using an animal, e.g., rodent, model system) if desired.

In vitro testing of a candidate compound can be accomplished by means known to those in the art, such as assays involving the use of cells, e.g., primary human hepatocytes. Exemplary assays for monitoring HBV infection as well as useful cells that can be used in such assays are described in the Examples section, below.

Alternatively or in addition, in vivo testing of candidate compounds can be performed by means known to those in the art. For example, the candidate compound(s) can be administered to a mammal, such as a rodent (e.g., mouse) or rabbit. Such animal model systems are art-accepted for testing potential pharmaceutical agents to determine their therapeutic efficacy in patients, e.g., human patients. Animals that are particularly useful for in vivo testing are immunodeficient animals (e.g., mice) with a human liver.

In a typical in vivo assay, an animal (e.g., a wild type or transgenic mouse) is administered, by any route deemed appropriate (e.g., by injection), a dose of a candidate compound. Conventional methods and criteria can then be used to monitor animals for the desired activity. If needed, the results obtained in the presence of the candidate compound can be compared with results in control animals that are not treated with the test compound.

Medicinal Chemistry

Once a compound (or agent) of interest has been identified, standard principles of medicinal chemistry can be used to produce derivatives of the compound for further rounds of testing. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

Pharmaceutical Compositions

Also described herein are pharmaceutical compositions, which include, e.g., LDLR, LRP, or RAP, e.g., where the LDLR, LRP, or RAP comprises a polypeptide that has at least 90, 92, 95, 96, 97, 98, or 99% identity to the amino acid sequence of SEQ ID NO:2, 4, or 6, respectively. The pharmaceutical compositions can include a combination of two or more of a LDLR, LRP, and RAP. Further, the pharmaceutical compositions can include a FXa inhibitor, a pegylated interferon, a nucleoside or nucleotide analogue, and/or a HBV vaccine.

The compounds and agents, e.g., small molecules, nucleic acids, polypeptides, and antibodies (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions. The pharmaceutical compositions can be included in a container, pack, or dispenser together with instructions for administration.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), or a suitable mixture thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Typically, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution, or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil.

Oral compositions typically include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Alternatively, the pharmaceutical composition can be formulated as a chewing gum, lollipop, or the like.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

In all of the methods described herein, appropriate dosages of LDLR, LRP, and RAP can readily be determined by those of ordinary skill in the art of medicine, e.g., by monitoring the patient for signs of disease amelioration or inhibition, and increasing or decreasing the dosage and/or frequency of treatment as desired. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount, e.g., of a protein or polypeptide (i.e., an effective dosage), ranges from about 0.001 to 30 mg/kg body weight, e.g., about 0.01 to 25 mg/kg body weight, e.g., about 0.1 to 20 mg/kg body weight. The protein or polypeptide can be administered one time per day, twice per day, one time per week, twice per week, for between about 1 to 52 weeks per year, e.g., between 2 to 50 weeks, about 6 to 40 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, nucleic acid, or other compound can include a single treatment or, preferably, can include a series of treatments.

For antibodies, a useful dosage is 5 mg/kg of body weight (typically 3 mg/kg to 20 mg/kg). Typically, partially human antibodies and fully human antibodies have a longer half-life within the human body than other antibodies. Accordingly, lower dosages and less frequent administration are possible. Modifications such as lipidation can be used to stabilize antibodies or other therapeutic proteins and to enhance uptake and tissue penetration. A method for lipidation of antibodies is described by Cruikshank et al. (J. Acquir. Immune Defic. Syndr. Hum. Retrovirol. 14:193, 1997). Alternatively, an antibody or a fragment thereof may be joined to a protein transduction domain, e.g., an HIV Tat-1 activator domain or the homeodomain of Antennapedia transcription factor (for review, see Heng and Cao, Medical Hypotheses 64:1105-8, 2005). Fusion proteins thus generated have been found to transduce into the cells of tissues in a mouse model system (Schwarze et al., Science 285:1569-1572, 1999).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

EXAMPLES

The invention is further described in the following examples, which do not limit the scope of the invention described in the claims.

Example 1

RAP Inhibits HBV Infection of HepaRG Cells

Differentiated HepaRG cells ($4 \times 10^4$), which are susceptible to HBV infection (Gripon et al., Proc Natl Acad Sci USA 99:15655-60, 2002), were incubated overnight with HBV inoculum in the presence or absence of increasing concentrations of RAP or GST-RAP, and washed extensively to remove unbound HBV virions and HBsAg. Medium was changed every 2-3 days. HBsAg level in culture supernatant was measured 10 days later (at this point there was no more residual HBsAg from the inoculum, and signals detected reflect newly synthesized and secreted proteins). The level of HBsAg secreted into the culture supernatant was determined by an ELISA assay using a commercially available kit (e.g., Novus Biologicals, NEO BioLab, Cusabio Biotech Co., Ltd.). Briefly, culture medium was added to wells containing capture antibody (anti-HBsAg), followed by incubation at 37° C. for 30 min. After washing with provided washing buffer, conjugate (anti-HBsAg conjugated with HRP) was added followed by incubation at 37° C. for 30 min. After washing, signals were revealed by addition of HRP substrate and optical density measured at 450 nm. A dose-dependent reduction of HBsAg secretion to culture supernatant was observed (FIG. 1), demonstrating a reduction of HBV infectivity. Since RAP is a universal inhibitor of the LDLR protein family, which in the liver includes LDLR and LRP, this demonstrates that LDLR and LRP can serve as components of a HBV receptor complex.

Example 2

LRP Expression is Upregulated in Differentiated HepaRG Cells

Figure 2:
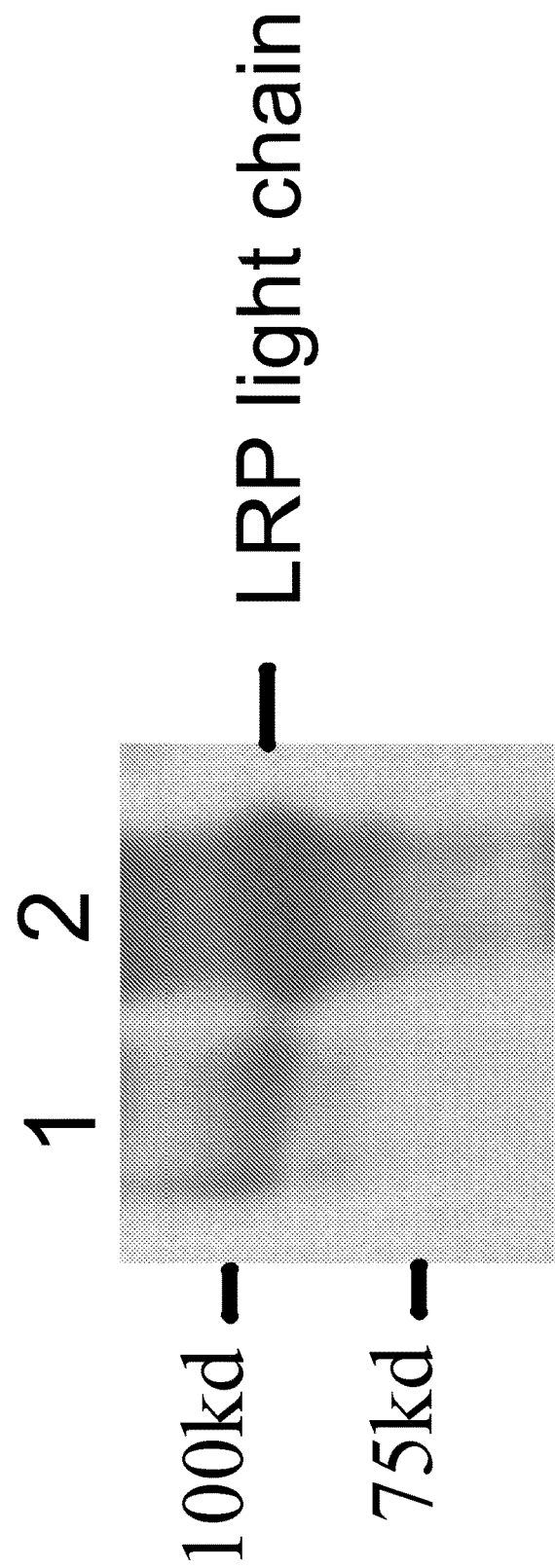
FIG. 2 is a photomicrograph showing upregulation of LRP expression in differentiated HepaRG cells. Confluent HepaRG cells were harvested before (lane 1) or two weeks following treatment with 2% DMSO (lane 2), and LRP was detected by IP-Western blot analysis.

HepaRG is a human liver progenitor cell line. It is undifferentiated during its growth phase. Treatment of confluent HepaRG cells with 2% DMSO for two weeks induces its differentiation into islands of hepatocytes surrounded by bile duct cells (Parent et al., Gastroenterology 126:1147-56, 2004). LRP was immunoprecipitated from cell lysate using a monoclonal antibody against its heavy chain, followed by Western blot analysis with an antibody against its light chain. Only a fraction of hepatocytes, but not bile duct cells, in differentiated HepaRG cells are susceptible to HBV infection. LRP expression was greatly enhanced in differentiated HepaRG cells relative to undifferentiated counterparts (FIG. 2). Therefore, LRP expression is dependent on differentiated status of hepatocytes. Primary human hepatocytes rapidly lose differentiation status during in vitro culture and also the susceptibility to HBV infection. The correlation of LRP expression with hepatocyte differentiation status is consistent with a role as a component of a HBV receptor complex.

Example 3

Figure 3:
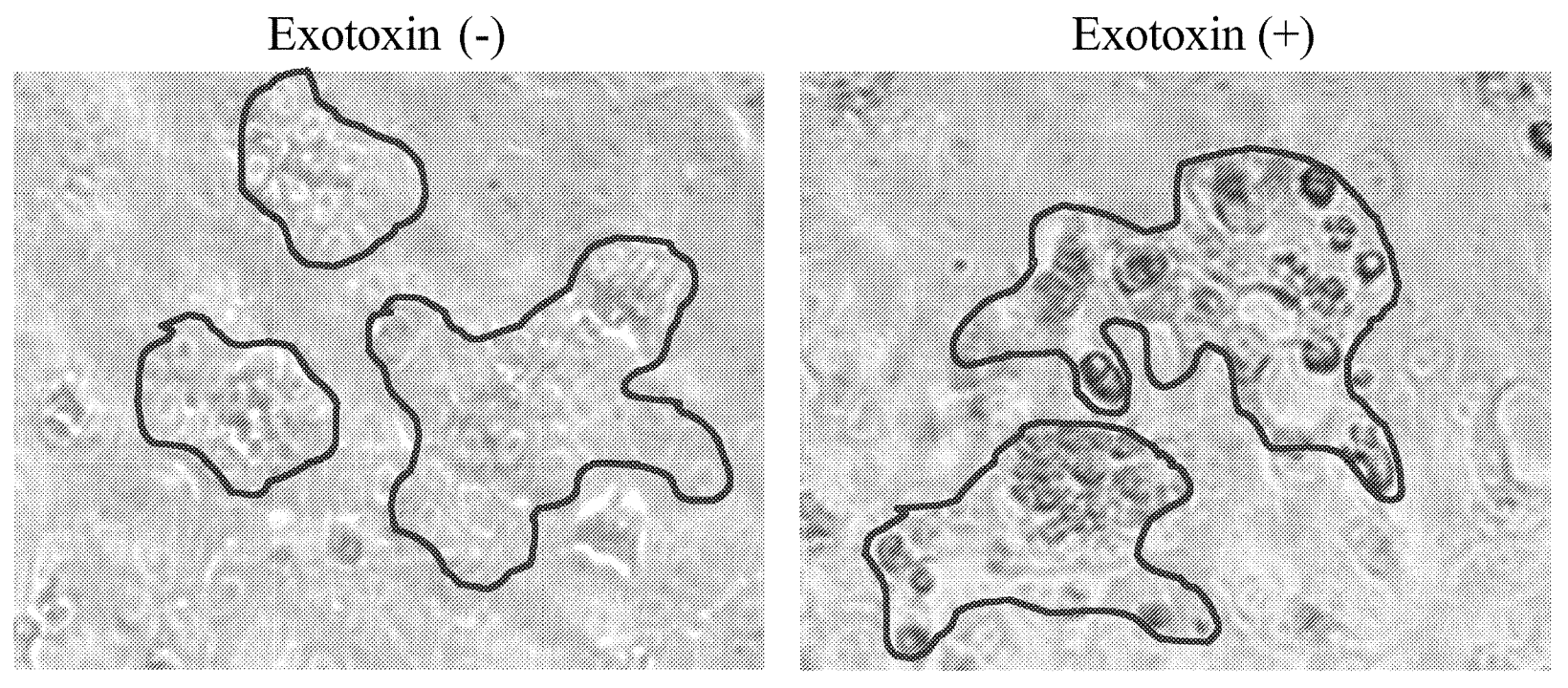

Pattern of LRP Expression Correlates with that of HBV Infection in Differentiated HepaRG Cells Hepatocytes are polarized. LRP is distributed at the basolateral side rather than apical side of hepatocytes (Marzolo et al., Traffic 4:273-88, 2003) consistent with HBV infection from the bloodstream. It was recently reported that HBV preferentially infects hepatocytes near the edge of hepatocyte islands (Schulze et al., Hepatology 55:373-83, 2012). *Pseudomonas* exotoxin, which uses LRP as its receptor (Kounnas et al., J Biol Chem 267:12420-3, 1992), selectively killed cells in the periphery of hepatocyte islands of HepaRG cells when used at a low dose (FIG. 3). Differentiated HepaRG cells were untreated (left panel) or incubated with *pseudomonas* exotoxin A (500 ng/ml) at 37° C. overnight (right panel), and stained with 0.04% trypan blue to reveal dead (blue) cells under microscopy. The dead cells were mainly located at the periphery of hepatocyte islands, which are also most susceptible to HBV infection.

Example 4

LRP Silencing Diminishes HBV Infection of HepaRG Cells

Figure 4:
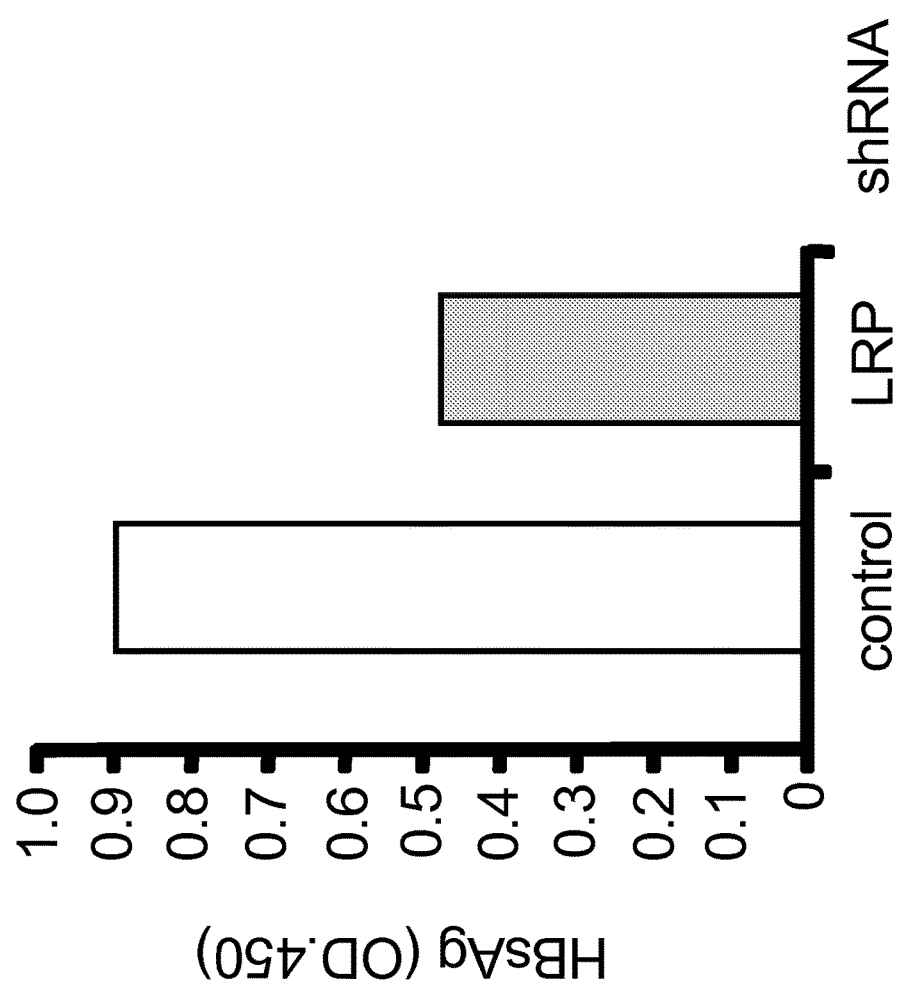
FIG. 4 is a bar graph showing the effect of LRP silencing on HBV infectivity in HepaRG cells, using HBsAg as an indicator.

To specifically test the role of LRP in mediating HBV infection, LRP expression was knocked down by shRNA. Proliferating HepaRG cells cultured in a 12-well plate were infected overnight with lentivirus carrying LRP shRNA or control shRNA. LRP shRNA was obtained from Santa Cruz Biotechnology, sc-40101-V, with lentiviral particles containing three to five expression constructs that each encode target-specific 19 to 25 nucleotides (plus hairpin) shRNA designed to knockdown gene expression. Control shRNA was obtained from Santa Cruz Biotechnology, sc-108080. Stably transduced cells were selected by puromycin (5 µg/ml). Cells were then differentiated for two weeks and infected with purified HBV particles. Measurement of HBsAg level at day 12 post-infection revealed about 50% reduction in infectivity with LRP shRNA when compared to cells transduced with control shRNA (FIG. 4).

Example 5

Figure 5:
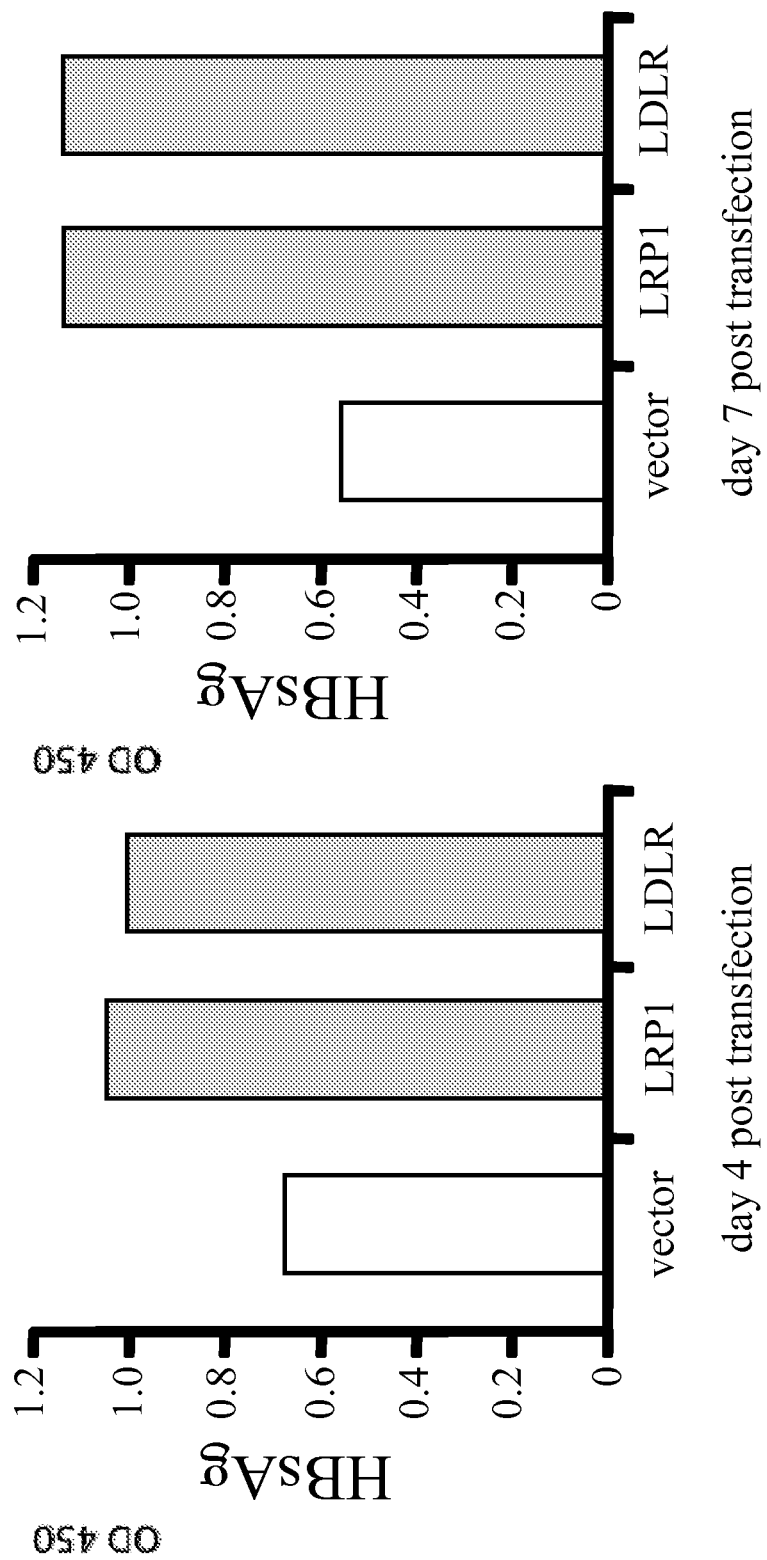
FIG. 5 is a panel of two bar graphs showing the impact of LRP and LDLR cDNAs on levels of secreted HBsAg at 4 days (left panel) and 7 days (right panel) posttransfection with a full-length HBV construct in Huh7 cell line.
Figure 6:
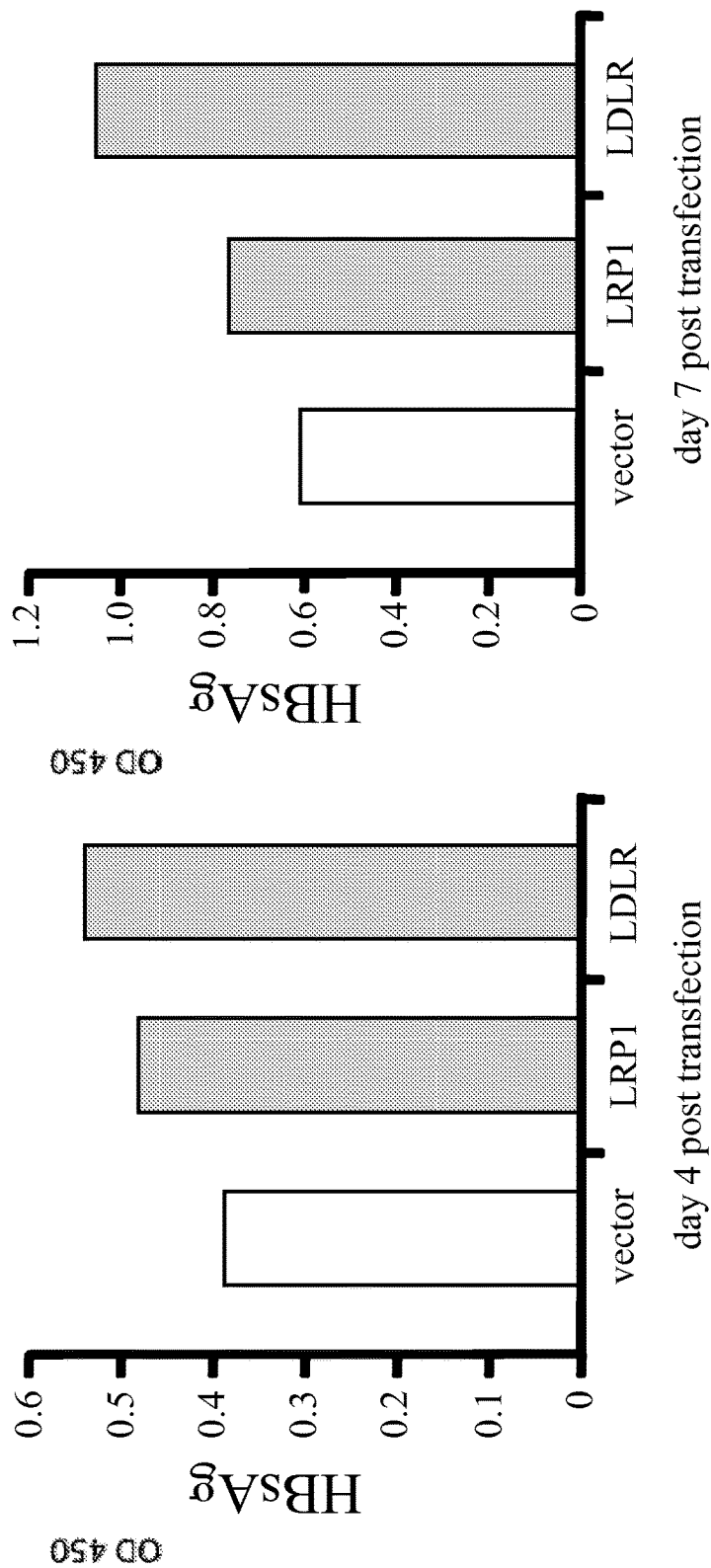
FIG. 6 is a panel of two bar graphs showing the impact of LRP and LDLR cDNAs on levels of secreted HBsAg at 4 days (left panel) and 7 days (right panel) posttransfection with a subgenomic HBV DNA construct in Huh7 cells.

Overexpression of Either LRP or LDLR Increases HBsAg Secretion from a Human Hepatoma Cell Line Besides testing the effect of LRP on HBV infectivity, LRP's impact on HBsAg and virion secretion was also evaluated. This experiment was performed on Huh7 cells, a human hepatoma cell line. Although Huh7 cells are resistant to HBV infection, the cells support viral gene expression, genome replication, as well as release of HBsAg and virions if transfected with full-length HBV DNA constructs. Huh7 cells were transfected with full-length HBV construct K85, together with vector DNA, LRP, or LDLR cDNA. Secreted HBsAg was measured at day 4 and 7 post-transfection, respectively. The amount of HBsAg secreted was markedly increased if the full-length HBV construct was co-transfected with LRP cDNA or LDLR cDNA instead of vector DNA (FIG. 5). When a subgenomic HBV fragment capable of HBsAg expression but not genome replication was used for a separate co-transfection experiment, similar results were obtained (FIG. 6). In that case, Huh7 cells were transfected with subgenomic HBV construct (N51) encoding HBsAg only, together with vector DNA, LRP, or LDLR cDNA. Secreted HBsAg was measured at day 4 and 7 post-transfection, respectively. Therefore, overexpression of LRP or LDLR enhances HBsAg secretion. The impact of LRP and LDLR cDNAs on virion secretion are also tested by co-transfecting cells with LRP cDNA or LDLR cDNA. In the reverse approach, the effect of LRP and LDLR shRNAs on HBsAg and virion secretion are tested.

Example 6

Inhibition of FXa Inhibits HBV Infection

Figure 7:
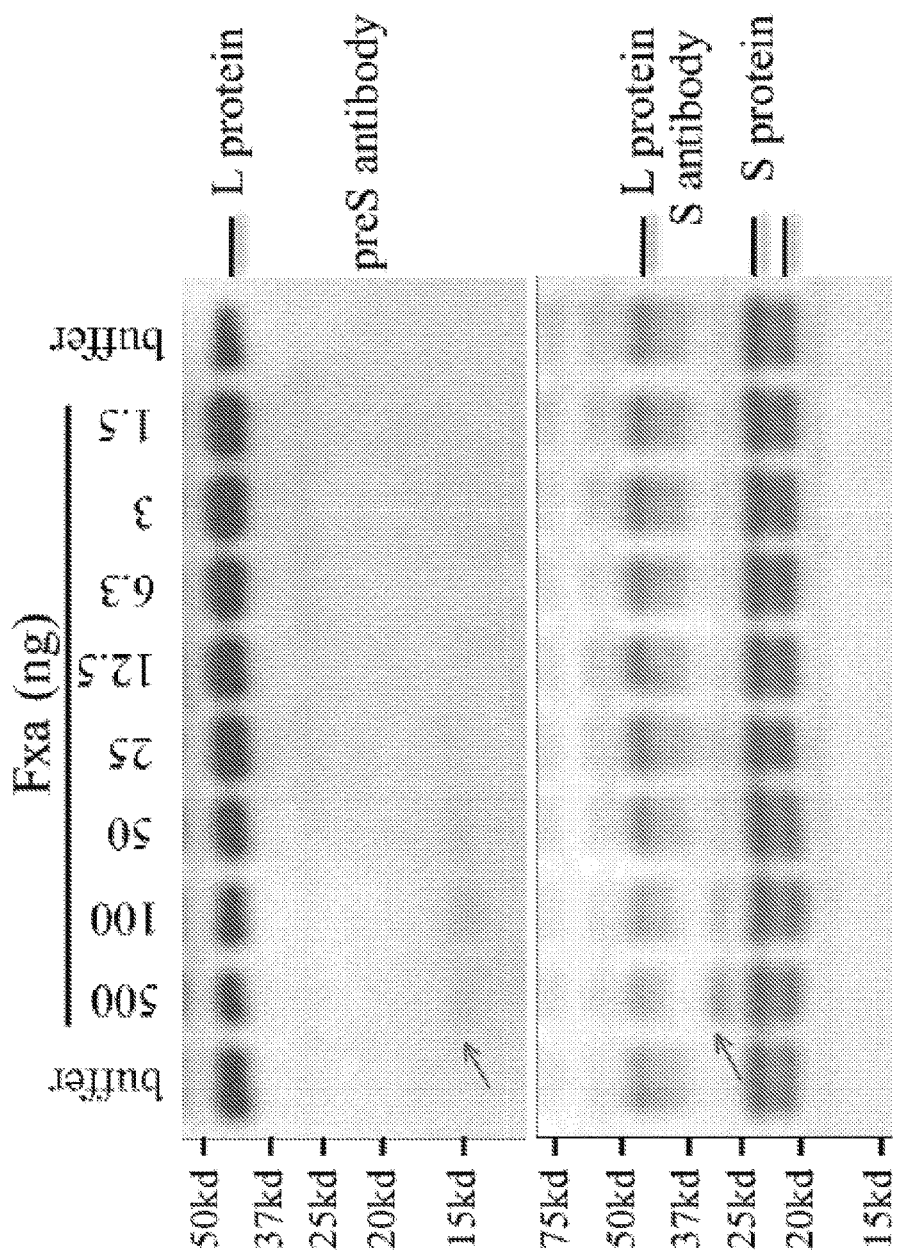
FIG. 7 is a series of two photomicrographs showing that FXa cleaves HBV L protein. The L protein was detected by Western blot analysis, with the cleavage product indicated by an arrowhead. The same blot was revealed by preS antibody (upper panel) and S antibody (lower panel), respectively.
Figure 8:
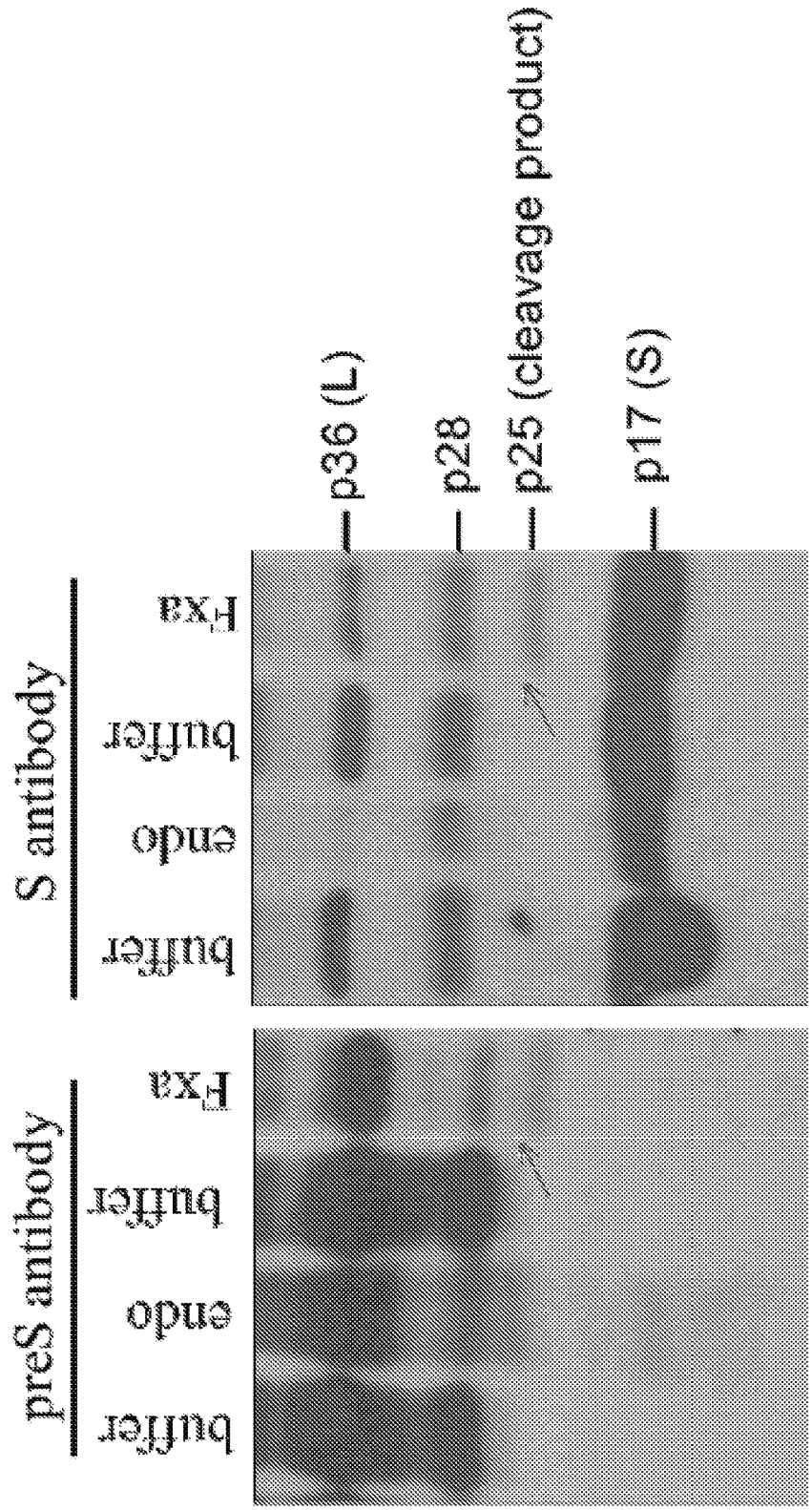
FIG. 8 is a series of two photomicrographs showing that FXa cleaves DHBV L protein. The cleavage product was revealed by Western blot analysis with a preS antibody (left panel) and an S antibody (right panel).
Figure 9:
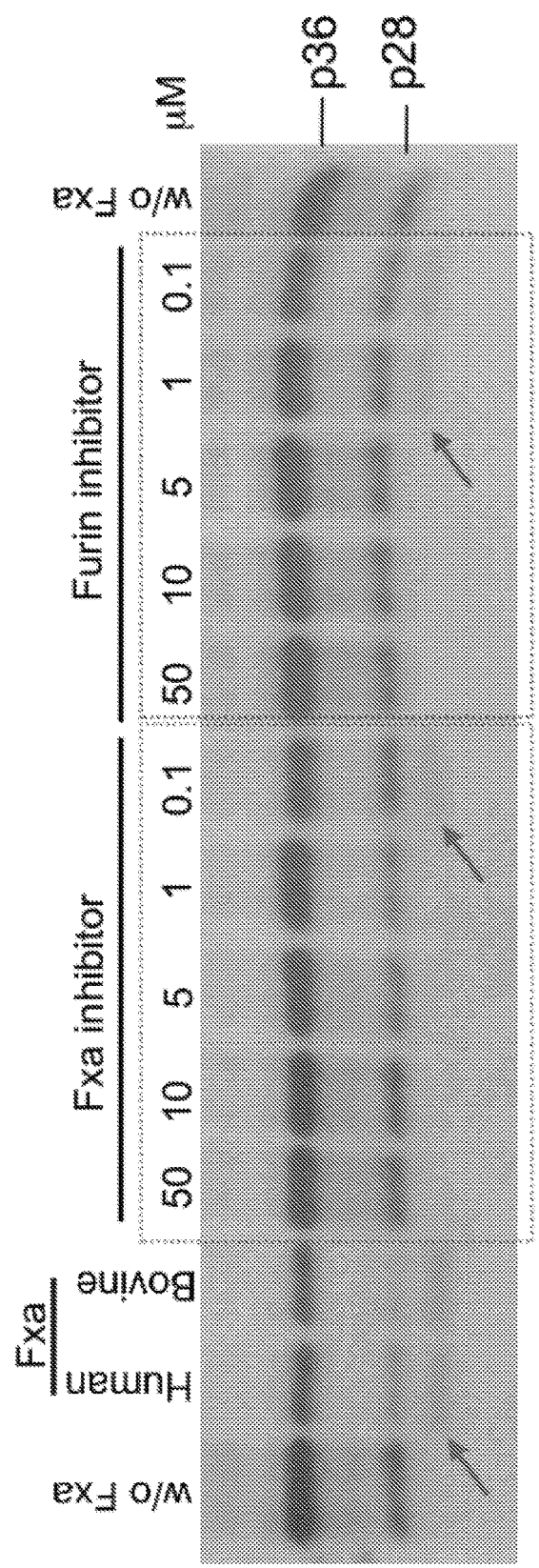
FIG. 9 is a photomicrograph of a Western blot showing that FXa cleavage of DHBV envelope protein is blocked by both FXa and furin inhibitors.

FXa could cleave envelope proteins on both HBV (FIG. 7) and DHBV (FIG. 8), which was blocked by a specific FXa inhibitor (FIG. 9). HBV particles were purified from patient serum by ultracentrifugation through 10-20% sucrose gradient. The purified virus particles were incubated, at 37° C. for three hours with various concentrations of FXa in a buffer containing 20 mM HEPES, pH 7.4, 0.15 M NaCl, 2 mM $CaCl_2$. The cleavage products (shown by arrows) were revealed by Western blot with anti-preS and anti-S antibodies, respectively (FIG. 7). Note that cleavage was most pronounced at 50-500 ng of FXa. DHBV particles were purified from viremic duck sera, and incubated at 37° C. for three hours with 100 ng of FXa. The cleavage product (shown by arrows) was revealed by Western blot using polyclonal preS antibody (FIG. 8, left panel) and monoclonal S antibody (FIG. 8, right panel). Incubation with buffer or duck liver endosome (endo) served as controls. The full-length DHBV L protein binds to duck carboxypeptidase D, whereas several truncated versions have affinity for p120, the p protein of glycine decarboxylase with high level expression in the liver and critical for DHBV infectivity. Therefore, FXa cleavage is a unifying theme in the entry process of HBV and DHBV, even though they use different molecules as cell surface receptors. Remarkably, a furin inhibitor, which blocked DHBV infection of primary duck hepatocytes, could inhibit FXa cleavage of DHBV envelope proteins. Purified DHBV particles were incubated at 37° C. for three hours with 100 ng of human or bovine FXa in the presence of various concentrations of FXa inhibitor or furin inhibitor. The cleavage product (shown by arrows) was revealed by Western blot analysis with a preS antibody (FIG. 9).

Figure 10:
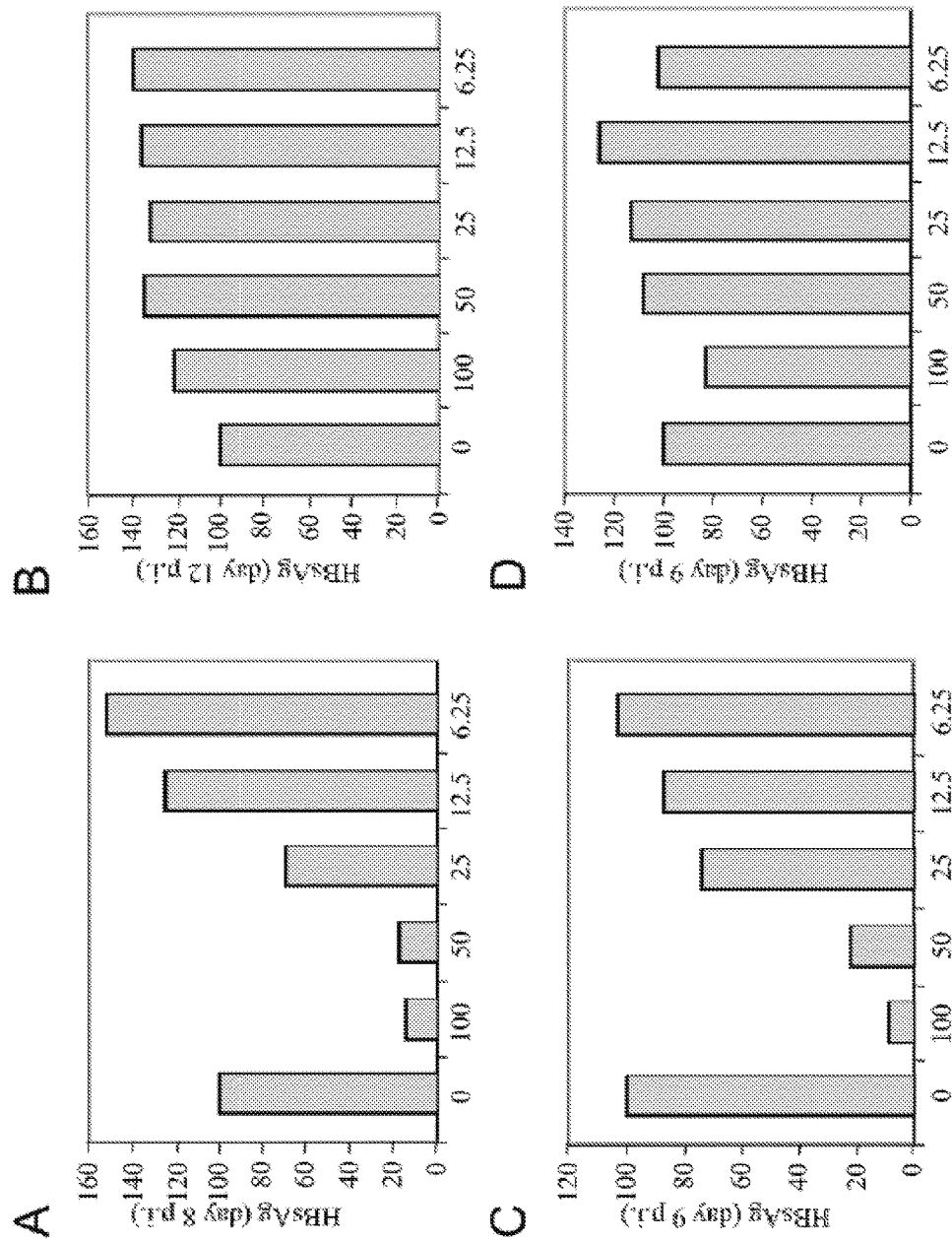
FIG. 10 is a series of four bar graphs showing that the 7-aa antistasin-related peptide inhibits HBV infection of HepaRG cells when added during the step of virus inoculation. (A) the peptide present during virus incubation. (B) the peptide present during the two days prior to infection. (C) the peptide present both during virus inoculation and in the first two days post-infection. (D) the peptide present during the first two days post-infection.

A seven amino acid antistasin-related peptide, a direct FXa inhibitor (Tuszynski et al., J Biol Chem 262:9718-23, 1987; Nutt et al., J Biol Chem 263:10162-7, 1988), efficiently blocked HBV infection of HepaRG cells in a dose-dependent manner (FIG. 10). HepaRG cells were incubated with HBV particles purified from a serum sample with different concentrations of the peptide (0-100 μM) added before, during, or post-infection. HBsAg was measured at indicated days post-infection with the value of non-treated cells set at 100%. The FXa inhibitory effect of the peptide is dependent on an intramolecular disulfide bond (Ohta et al., Thromb Haemost 72:825-30, 1994). In this regard, the same peptide without such disulfide bond failed to inhibit HBV infection.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject against hepatitis B virus (HBV) infection, the method comprising
identifying the subject in need of being treated against HBV infection; and
administering to the subject a therapeutically effective amount of purified receptor associated protein (RAP) that binds to low density lipoprotein receptor related protein (LRP) and a HBV vaccine,
wherein the subject is not diagnosed of having liver cancer, and the RAP comprises an amino acid sequence that has at least 90% identity to SEQ ID NO:6,
thereby treating the subject against HBV infection.

2. The method of claim 1, wherein the RAP comprises an amino acid sequence that has at least 95% identity to SEQ ID NO:6.

3. A method of treating a subject against HBV infection, the method comprising administering to the subject a therapeutically effective amount of an anti-HBV agent consisting of receptor associated protein (RAP), thereby treating the subject against HBV infection, wherein the RAP comprises an amino acid sequence that has at least 90% identity to SEQ ID NO:6 and the RAP binds to low density lipoprotein receptor related protein (LRP).

4. The method of claim 3, wherein the RAP comprises an amino acid sequence that has at least 95% identity to SEQ ID NO:6.

5. The method of claim 3, wherein the RAP comprises the amino acid sequence set forth in SEQ ID NO:6.

6. The method of claim 3, wherein the method consists of administering to the subject a therapeutically effective amount of the anti-HBV agent consisting of RAP.

7. The method of claim 6, wherein the RAP consists of an amino acid sequence that has at least 90% identity to SEQ ID NO: 6.

8. The method of claim 6, wherein the RAP consists of an amino acid sequence that has at least 95% identity to SEQ ID NO:6.

9. The method of claim 6, wherein the RAP consists of the amino acid sequence set forth in SEQ ID NO:6.

10. The method of claim 3, wherein the RAP consists of an amino acid sequence that has at least 90% identity to SEQ ID NO: 6.

11. The method of claim 3, wherein the RAP consists of an amino acid sequence that has at least 95% identity to SEQ ID NO:6.

12. The method of claim 3, wherein the RAP consists of the amino acid sequence set forth in SEQ ID NO:6.

13. The method of claim 3, wherein the method further comprises administering to the subject a HBV vaccine.

14. The method of claim 3, wherein the method further comprises administering to the subject a pegylated interferon, or a nucleoside or nucleotide analogue.

15. The method of claim 3, wherein the subject is a human.

16. The method of claim 3, wherein the method further comprises administering to the subject a therapeutically effective amount of soluble LDLR, and the soluble LDLR comprises an amino acid sequence that has at least 90% identity to SEQ ID NO:2.

17. The method of claim 3, wherein the method further comprises administering to the subject a therapeutically effective amount of soluble LRP, and the soluble LRP comprises an amino acid sequence that has at least 90% identity to SEQ ID NO:4.

18. A method of inhibiting HBV infection of a liver cell, the method comprising contacting the liver cell with an effective amount of an anti-HBV agent consisting of receptor associated protein (RAP), wherein the RAP comprises an amino acid sequence that has at least 90% identity to SEQ ID NO:6 and the RAP binds to low density lipoprotein receptor related protein (LRP), thereby inhibiting HBV infection of the liver cell.

19. The method of claim 18, wherein the liver cell is in a subject who is in need of being treated against HBV infection.

20. The method of claim 18, wherein the liver cell is a cultured cell.

21. The method of claim 18, wherein the RAP comprises an amino acid sequence that has at least 95% identity to SEQ ID NO:6.

22. The method of claim 18, wherein the RAP comprises the amino acid sequence set forth in SEQ ID NO:6.

* * * * *

SEQUENCE LISTING

```
<160> NUMBER OF SEQ ID NOS: 16

<210> SEQ ID NO 1
<211> LENGTH: 2583
<212> TYPE: DNA
<213> ORGANISM: Artificial Sequence
<220> FEATURE:
<223> OTHER INFORMATION: human low density lipoprotein receptor (LDLR)

<400> SEQUENCE: 1
atggggccct ggggctggaa attgcgctgg accgtcgcct tgctcctcgc cgcggcgggg      60
actgcagtgg gcgacagatg cgaaagaaac gagttccagt gccaagacgg gaaatgcatc     120
tcctacaagt gggtctgcga tggcagcgct gagtgccagg atggctctga tgagtcccag     180
gagacgtgct tgtctgtcac ctgcaaatcc ggggacttca gctgtggggg ccgtgtcaac     240
cgctgcattc ctcagttctg gaggtgcgat ggccaagtgg actgcgacaa cggctcagac     300
gagcaaggct gtccccccaa gacgtgctcc caggacgagt ttcgctgcca cgatgggaag     360
tgcatctctc ggcagttcgt ctgtgactca gaccgggact gcttggacgg ctcagacgag     420
gcctcctgcc cggtgctcac ctgtggtccc gccagcttcc agtgcaacag ctccacctgc     480 atccccagc tgtgggcctg cgacaacgac cccgactgcg aagatggctc ggatgagtgg     540
ccgcagcgct gtagggtct ttacgtgttc aaggggaca gtagccctg ctcggccttc     600 gagttccact gcctaagtgg cgagtgcatc cactccagct ggcgctgtga tggtggcccc     660
```

```
gactgcaagg acaaatctga cgaggaaaac tgcgctgtgg ccacctgtcg ccctgacgaa      720
ttccagtgct ctgatggaaa ctgcatccat ggcagccggc agtgtgaccg ggaatatgac      780
tgcaaggaca tgagcgatga agttggctgc gttaatgtga cactctgcga gggacccaac      840
aagttcaagt gtcacagcgg cgaatgcatc accctggaca agtctgcaa catggctaga       900 gactgccggg actggtcaga tgaacccatc aaagagtgcg ggaccaacga atgcttggac      960
aacaacggcg gctgttccca cgtctgcaat gaccttaaga tcggctacga gtgcctgtgc     1020
cccgacggct tccagctggt ggcccagcga agatgcgaag atatcgatga gtgtcaggat     1080
cccgacacct gcagccagct ctgcgtgaac ctggagggtg gctacaagtg ccagtgtgag     1140
gaaggcttcc agctggaccc ccacacgaag gcctgcaagg ctgtgggctc catcgcctac     1200
ctcttcttca ccaaccggca cgaggtcagg aagatgacgc tggaccggag cgagtacacc     1260
agcctcatcc ccaacctgag gaacgtggtc gctctggaca cggaggtggc agcaataga      1320 atctactggt ctgacctgtc ccagagaatg atctgcagca cccagcttga cagagcccac     1380
ggcgtctctt cctatgacac cgtcatcagc agagacatcc aggccccga cgggctggct      1440 gtggactgga tccacagcaa catctactgg accgactctg tcctgggcac tgtctctgtt     1500
gcggatacca agggcgtgaa gaggaaaacg ttattcaggg agaacggctc caagccaagg     1560
gccatcgtgg tggatcctgt tcatggcttc atgtactgga ctgactgggg aactcccgcc     1620
aagatcaaga agggggcct gaatggtgtg acatctact cgctggtgac tgaaaacatt       1680
cagtggccca atgcatcac cctagatctc ctcagtggcc gcctctactg ggttgactcc      1740
aaacttcact ccatctcaag catcgatgtc aacggggca accggaagac catcttggag      1800
gatgaaaaga ggctggccca ccccttctcc ttggccgtct ttgaggacaa agtatttggg     1860
acagatatca tcaacgaagc cattttcagt gccaaccgcc tcacaggttc cgatgtcaac     1920
ttgttggctg aaaacctact gtccccagag gatatggttc tcttccacaa cctcacccag     1980
ccaagaggag tgaactggtg tgagaggacc acctgagca atggcggctg ccagtatctg      2040
tgcctccctg ccccgcagat caaccccac tcgcccaagt ttacctgcgc ctgcccggac      2100
ggcatgctgc tggccaggga catgaggagc tgcctcacag aggctgaggc tgcagtggcc     2160
acccaggaga catccaccgt caggctaaag gtcagctcca cagccgtaag gacacagcac     2220
acaaccaccc gacctgttcc cgacacctcc cggctgcctg ggccaccc tgggctcacc       2280 acggtggaga tagtgacaat gtctcaccaa gctctgggcg acgttgctgg cagaggaaat     2340
gagaagaagc ccagtagcgt gagggctctg tccattgtcc tccccatcgt gctcctcgtc     2400
ttcctttgcc tgggggtctt ccttctatgg aagaactggc ggcttaagaa catcaacagc     2460
atcaactttg acaaccccgt ctatcagaag accacagagg atgaggtcca catttgccac     2520
aaccaggacg gctacagcta ccctcgaga cagatggtca gtctggagga tgacgtggcg     2580
tga                                                                   2583
```

<210> SEQ ID NO 2
<211> LENGTH: 860
<212> TYPE: PRT
<213> ORGANISM: Artificial Sequence
<220> FEATURE:
<223> OTHER INFORMATION: human low density lipoprotein receptor (LDLR)

<400> SEQUENCE: 2

Met Gly Pro Trp Gly Trp Lys Leu Arg Trp Thr Val Ala Leu Leu Leu
1               5                   10                  15

```
Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
50                  55                  60

Ser Val Thr Cys Lys Ser Gly Asp Phe Ser Cys Gly Gly Arg Val Asn
65                      70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
            115                 120                 125

Asp Ser Asp Arg Asp Cys Leu Asp Gly Ser Asp Glu Ala Ser Cys Pro
130                 135                 140

Val Leu Thr Cys Gly Pro Ala Ser Phe Gln Cys Asn Ser Ser Thr Cys
145                     150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
        210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
            245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
        290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
            325                 330                 335

Glu Cys Leu Cys Pro Asp Gly Phe Gln Leu Val Ala Gln Arg Arg Cys
        340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
        370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430
```

```
Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
                500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
        530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
                580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
        610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
                820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
```

<210> SEQ ID NO 3
<211> LENGTH: 13635
<212> TYPE: DNA
<213> ORGANISM: Artificial Sequence
<220> FEATURE:
<223> OTHER INFORMATION: human low density lipoprotein receptor related protein (LRP)

<400> SEQUENCE: 3

| | | | | | |
|---|---|---|---|---|---|
| atgctgaccc | cgccgttgct | cctgctgctg | ccctgctct | cagctctggt | cgcggcggct | 60 |
| atcgacgccc | ctaagacttg | cagccccaag | cagtttgcct | gcagagatca | aataaccctgt | 120 |
| atctcaaagg | gctggcggtg | cgacggtgag | agggactgcc | agacggatc | tgacgaggcc | 180 |
| cctgagattt | gtccacagag | taaggcccag | cgatgccagc | caaacgagca | taactgcctg | 240 |
| ggtactgagc | tgtgtgttcc | catgtcccgc | ctctgcaatg | gggtccagga | ctgcatggac | 300 |
| ggctcagatg | aggggcccca | ctgccgagag | ctccaaggca | actgctctcg | cctgggctgc | 360 |
| cagcaccatt | gtgtccccac | actcgatggg | cccacctgct | actgcaacag | cagctttcag | 420 |
| cttcaggcag | atggcaagac | ctgcaaagat | tttgatgagt | gctcagtgta | cggcacctgc | 480 |
| agccagctat | gcaccaacac | agacggctcc | ttcatatgtg | gctgtgttga | aggataccct | 540 |
| ctgcagccgg | ataaccgctc | ctgcaaggcc | aagaacgagc | cagtagaccg | gccccctgtg | 600 |
| ctgttgatag | ccaactccca | gaacatcttg | gccacgtacc | tgagtggggc | ccaggtgtct | 660 |
| accatcacac | ctacgagcac | gcggcagacc | acagccatgg | acttcagcta | tgccaacgag | 720 |
| accgtatgct | gggtgcatgt | tgggacagt | gctgctcaga | cgcagctcaa | gtgtgcccgc | 780 |
| atgcctggcc | taaagggctt | cgtggatgag | cacaccatca | acatctccct | cagtctgcac | 840 |
| cacgtggaac | agatggccat | cgactggctg | acaggcaact | tctactttgt | ggatgacatc | 900 |
| gatgatagga | tctttgtctg | caacagaaat | ggggacacat | gtgtcacatt | gctagacctg | 960 |
| gaactctaca | accccaaggg | cattgccctg | gaccctgcca | tggggaaggt | gttttcact | 1020 |
| gactatggc | agatcccaaa | ggtggaacgc | tgtgacatgg | atgggcagaa | ccgcaccaag | 1080 |
| ctcgtcgaca | gcaagattgt | gtttcctcat | ggcatcacgc | tggacctggt | cagccgcctt | 1140 |
| gtctactggg | cagatgccta | tctggactat | attgaagtgg | tggactatga | gggcaagggc | 1200 |
| cgccagacca | tcatccaggg | catcctgatt | gagcacctgt | acggcctgac | tgtgtttgag | 1260 |
| aattatctct | atgccaccaa | ctcggacaat | gccatgccc | agcagaagac | gagtgtgatc | 1320 |
| cgtgtgaacc | gctttaacag | caccgagtac | caggttgtca | cccggggtgga | caagggtggt | 1380 |
| gccctccaca | tctaccacca | gaggcgtcag | ccccgagtga | ggagccatgc | ctgtgaaaac | 1440 |
| gaccagtatg | ggaagccggg | tggctgctct | gacatctgcc | tgctggccaa | cagccacaag | 1500 |
| gcgcggacct | gccgctgccg | ttccggcttc | agcctgggca | gtgacgggaa | gtcatgcaag | 1560 |
| aagccggagc | atgagctgtt | cctcgtgtat | ggcaagggcc | ggccaggcat | catccggggc | 1620 |
| atggatatgg | gggccaaggt | cccggatgag | cacatgatcc | ccattgaaaa | cctcatgaac | 1680 |
| ccccgagccc | tggacttcca | cgctgagacc | ggcttcatct | actttgccga | caccaccagc | 1740 |
| tacctcattg | gccgcagaa | gattgatggc | actgagcggg | agaccatcct | gaaggacggc | 1800 |
| atccacaatg | tggagggtgt | ggccgtggac | tggatgggag | acaatctgta | ctggacggac | 1860 |
| gatgggccca | aaagacaat | cagcgtggcc | aggctggaga | agctgctca | gacccgcaag | 1920 |
| actttaatcg | agggcaaaat | gacacacccc | agggctattg | tggtggatcc | actcaatggg | 1980 |

```
tggatgtact ggacagactg ggaggaggac cccaaggaca gtcggcgtgg gcggctggag    2040
agggcgtgga tggatggctc acaccgagac atctttgtca cctccaagac agtgctttgg    2100
cccaatgggc taagcctgga catcccggct gggcgcctct actgggtgga tgccttctac    2160
gaccgcatcg agacgatact gctcaatggc acagaccgga agattgtgta tgaaggtcct    2220
gagctgaacc acgcctttgg cctgtgtcac catggcaact acctcttctg gactgagtat    2280
cggagtggca gtgtctaccg cttggaacgg ggtgtaggag gcgcaccccc cactgtgacc    2340
cttctgcgca gtgagcggcc ccccatcttt gagatccgaa tgtatgatgc ccagcagcag    2400
caagttggcc ccaacaaatg ccgggtgaac aatggcggct gcagcagcct gtgcttggcc    2460
acccctggga gccgccagtg cgcctgtgct gaggaccagg tgttggacgc agacggcgtc    2520
acttgcttgg cgaacccatc ctacgtgcct ccaccccagt gccagccagg cgagtttgcc    2580
tgtgccaaca gccgctgcat ccaggagcgc tggaagtgtg acggagacaa cgattgcctg    2640
gacaacagtg atgaggcccc agccctctgc catcagcaca cctgcccctc ggaccgattc    2700
aagtgcgaga caaccggtg catccccaac cgctggctct gcgacgggga caatgactgt    2760
gggaacagtg aagatgagtc caatgccact tgttcagccc gcacctgccc ccccaaccag    2820
ttctcctgtg ccagtggccg ctgcatcccc atctcctgga cgtgtgatct ggatgacgac    2880 tgtgggacc gctctgatga gtctgcttcg tgtgcctatc ccacctgctt ccccctgact    2940
cagtttacct gcaacaatgg cagatgtatc aacatcaact ggagatgcga caatgacaat    3000
gactgtgggg acaacagtga cgaagccggc tgcagccact cctgttctag cacccagttc    3060
aagtgcaaca gcgggcgttg catccccgag cactggacct cgatggggga caatgactgc    3120
ggagactaca gtgatgagac acacgccaac tgcaccaacc aggccacgag gccccctggt    3180
ggctgccaca ctgatgagtt ccagtgccgg ctggatggac tatgcatccc cctgcggtgg    3240
cgctgcgatg ggacactga ctgcatggac tccagcgatg agaagagctg tgagggagtg    3300
acccacgtct gcgatcccag tgtcaagttt ggctgcaagg actcagctcg gtgcatcagc    3360
aaagcgtggg tgtgtgatgg cgacaatgac tgtgaggata actcggacga ggagaactgc    3420
gagtccctgg cctgcaggcc accctcgcac ccttgtgcca acaacacctc agtctgcctg    3480 cccccctgaca agctgtgtga tgcaacgac gactgtggcg acggctcaga tgagggcgag    3540
ctctgcgacc agtgctctct gaataacggt ggctgcagcc acaactgctc agtggcacct    3600
ggcgaaggca ttgtgtgttc ctgccctctg ggcatggagc tggggcccga caaccacacc    3660
tgccagatcc agagctactg tgccaagcat ctcaaatgca gccaaaagtg cgaccagaac    3720
aagttcagcg tgaagtgctc ctgctacgag ggctgggtcc tggaacctga cggcgagagc    3780
tgccgcagcc tggaccccct caagccgttc atcattttct ccaaccgcca tgaaatccgg    3840
cgcatcgatc ttcacaaagg agactacagc gtcctggtgc ccggcctgcg caacaccatc    3900
gccctggact ccaccctcag ccagagcgcc ctctactgga ccgacgtggt ggaggacaag    3960
atctaccgcg ggaagctgct ggacaacgga gccctgacta gtttcgaggt ggtgattcag    4020
tatggcctgg ccacacccga gggcctggct gtagactgga ttgcaggcaa catctactgg    4080
gtggagagta acctggatca gatcgaggtg gccaagctgg atgggaccct ccggaccacc    4140
ctgctggccg gtgacattga gcacccaagg gcaatcgcac tggatccccg ggatgggatc    4200 ctgtttttgga cagactggga tgccagcctg ccccgcattg aggcagcctc catgagtggg    4260
gctgggcgcc gcaccgtgca ccgggagacc ggctctgggg gctggcccaa cgggctcacc    4320
gtggactacc tggagaagcg catcctttgg attgacgcca ggtcagatgc catttactca    4380
```

```
gcccgttacg acggctctgg ccacatggag gtgcttcggg gacacgagtt cctgtcgcac    4440
ccgtttgcag tgacgctgta cgggggggag gtctactgga ctgactggcg aacaaacaca    4500
ctggctaagg ccaacaagtg gaccggccac aatgtcaccg tggtacagag gaccaacacc    4560
cagccctttg acctgcaggt gtaccacccc tcccgccagc ccatggctcc caatccctgt    4620
gaggccaatg ggggccaggg ccctgctcc cacctgtgtc tcatcaacta caaccggacc     4680
gtgtcctgcg cctgccccca cctcatgaag ctccacaagg acaacaccac ctgctatgag    4740
tttaagaagt tcctgctgta cgcacgtcag atggagatcc gaggtgtgga cctggatgct    4800
ccctactaca actacatcat ctccttcacg gtgcccgaca tcgacaacgt cacagtgcta    4860
gactacgatg cccgcgagca gcgtgtgtac tggtctgacg tgcggacaca ggccatcaag    4920
cgggccttca tcaacggcac aggcgtggag acagtcgtct ctgcagactt gccaaatgcc    4980
cacgggctgg ctgtggactg ggtctcccga aacctgttct ggacaagcta tgacaccaat    5040
aagaagcaga tcaatgtggc ccggctggat ggctccttca agaacgcagt ggtgcagggc    5100
ctggagcagc cccatggcct tgtcgtccac cctctgcgtg ggaagctcta ctggaccgat    5160
ggtgacaaca tcagcatggc caacatggat ggcagcaatc gcaccctgct cttcagtggc    5220
cagaagggcc ccgtgggcct ggctattgac ttccctgaaa gcaaactcta ctggatcagc    5280
tccgggaacc ataccatcaa ccgctgcaac ctggatggga gtgggctgga ggtcatcgat    5340
gccatgcgga gccagctggg caaggccacc gccctggcca tcatggggga caagctgtgg    5400
tgggctgatc aggtgtcgga aaagatgggc acatgcagca aggctgacgg ctcgggctcc    5460
gtggtccttc ggaacagcac caccctggtg atgcacatga aggtctatga cgagagcatc    5520
cagctggacc ataagggcac caaccccctgc agtgtcaaca cggtgactg ctcccagctc    5580
tgcctgccca cgtcagagac gacccgctcc tgcatgtgca cagccggcta tagcctccgg    5640
agtggccagc aggcctgcga gggcgtaggt tcctttctcc tgtactctgt gcatgaggga    5700
atcaggggaa ttcccctgga tcccaatgac aagtcagatg ccctggtccc agtgtccggg    5760
acctcgctgg ctgtcggcat cgacttccac gctgaaaatg acaccatcta ctgggtggac    5820
atgggcctga gcacgatcag ccgggccaag cgggaccaga cgtggcgtga agacgtggtg    5880
accaatggca ttggccgtgt ggagggcatt gcagtggact ggatcgcagg caacatctac    5940
tggacagacc agggctttga tgtcatcgag gtcgcccggc tcaatggctc cttccgctac    6000
gtggtgatct cccagggtct agacaagccc cgggccatca ccgtccaccc ggagaaaggg    6060
tacttgttct ggactgagtg gggtcagtat ccgcgtattg agcggtctcg gctagatggc    6120
acggagcgtg tggtgctggt caacgtcagc atcagctggc ccaacggcat ctcagtggac    6180
taccaggatg ggaagctgta ctggtgcgat gcacggacag acaagattga acggatcgac    6240
ctggagacag gtgagaaccg cgaggtggtt ctgtccagca caacatggga catgttttca    6300
gtgtctgtgt ttgaggattt catctactgg agtgacagga ctcatgccaa cggctctatc    6360
aagcgcggga gcaaagacaa tgccacagac tccgtgcccc tgcgaaccgg catcggcgtc    6420
cagcttaaag acatcaaagt cttcaaccgg gaccggcaga aaggcaccaa cgtgtgcgcg    6480
gtggccaatg gcgggtgcca gcagctgtgc ctgtaccggg gccgtgggca gcgggcctgc    6540
gcctgtgccc acgggatgct ggctgaagac ggagcatcgt gccgcgagta tgccggctac    6600
ctgctctact cagagcgcac cattctcaag agtatccacc tgtcggatga gcgcaacctc    6660
aatgcgcccg tgcagcccct cgaggaccct gagcacatga agaacgtcat cgccctggcc    6720
```

```
tttgactacc gggcaggcac ctctccgggc accccccaatc gcatcttctt cagcgacatc    6780
cactttggga acatccaaca gatcaacgac gatggctcca ggaggatcac cattgtggaa    6840
aacgtgggct ccgtggaagg cctggcctat accgtggct gggacactct ctattggaca    6900
agctacacga catccaccat cacgcgccac acagtggacc agacccgccc agggccttc    6960 gagcgtgaga ccgtcatcac tatgtctgga gatgaccacc cacgggcctt cgttttggac    7020
gagtgccaga acctcatgtt ctggaccaac tggaatgagc agcatcccag catcatgcgg    7080
gcggcgctct cgggagccaa tgtcctgacc cttatcgaga aggacatccg tacccccaat    7140
ggcctggcca tcgaccaccg tgccgagaag ctctacttct ctgacgccac cctggacaag    7200
atcgagcggt gcgagtatga cggctcccac cgctatgtga tcctaaagtc agagcctgtc    7260 cacccccttcg ggctggccgt gtatgggag cacattttct ggactgactg ggtgcggcgg    7320
gcagtgcagc gggccaacaa gcacgtgggc agcaacatga agctgctgcg cgtggacatc    7380
ccccagcagc ccatgggcat catcgccgtg ccaacgaca ccaacagctg tgaactctct    7440
ccatgccgaa tcaacaacgg tggctgccag gacctgtgtc tgctcactca ccagggccat    7500
gtcaactgct catgccgagg gggccgaatc ctccaggatg acctcacctg ccgagcggtg    7560
aattcctctt gccgagcaca agatgagttt gagtgtgcca atggcgagtg catcaacttc    7620
agcctgacct gcgacggcgt ccccactgc aaggacaagt ccgatgagaa gccatcctac    7680
tgcaactccc gccgctgcaa gaagactttc cggcagtgca gcaatgggcg ctgtgtgtcc    7740
aacatgctgt ggtgcaacgg ggccgacgac tgtggggatg gctctgacga gatcccttgc    7800
aacaagacag cctgtggtgt gggcgagttc cgctgccggg acgggacctg catcgggaac    7860
tccagccgct gcaaccagtt tgtggattgt gaggacgcct cagatgagat gaactgcagt    7920
gccaccgact gcagcagcta cttccgcctg ggcgtgaagg gcgtgctctt ccagccctgc    7980
gagcggacct cactctgcta cgcacccagc tgggtgtgtg atggcgccaa tgactgtggg    8040
gactacagtg atgagcgcga ctgcccaggt gtgaaacgcc ccagatgccc tctgaattac    8100
ttcgcctgcc ctagtgggcg ctgcatcccc atgagctgga cgtgtgacaa agaggatgac    8160
tgtgaacatg gcgaggacga gacccactgc aacaagttct gctcagaggc ccagtttgag    8220
tgccagaacc atcgctgcat ctccaagcag tggctgtgtg acggcagcga tgactgtggg    8280
gatggctcag acgaggctgc tcactgtgaa ggcaagacgt gcggccctc ctccttctcc    8340 tgccctggca cccacgtgtg cgtccccgag cgctggctct gtgacggtga caaagactgt    8400
gctgatggtg cagacgagag catcgcagct ggttgcttgt acaacagcac ttgtgacgac    8460
cgtgagttca tgtgccagaa ccgccagtgc atccccaagc acttcgtgtg tgaccacgac    8520
cgtgactgtg cagatggctc tgatgagtcc ccgagtgtg agtacccgac ctgcggcccc    8580
agtgagttcc gctgtgccaa tgggcgctgt ctgagctccc gccagtggga gtgtgatggc    8640
gagaatgact gccacgacca gagtgacgag gctcccaaga acccacactg caccagccaa    8700
gagcacaagt gcaatgcctc gtcacagttc ctgtgcagca gtgggcgctg tgtggctgag    8760
gcactgctct gcaacggcca ggatgactgt ggcgacagct cggacgagcg tggctgccac    8820
atcaatgagt gtctcagccg caagctcagt ggctgcagcc aggactgtga ggacctcaag    8880
atcggcttca gtgccgctg tcgccctggc ttccggctga aggacgacgg ccggacgtgt    8940
gctgatgtgg acgagtgcag caccaccttc cctgcagcc agcgctgcat caacactcat    9000
ggcagctata agtgtctgtg tgtggagggc tatgcacccc gcggcggcga cccccacagc    9060
tgcaaggctg tgactgacga ggaaccgttt ctgatcttcg ccaaccggta ctacctgcgc    9120
```

```
aagctcaacc tggacgggtc caactacacg ttacttaagc agggcctgaa caacgccgtt    9180
gccttggatt ttgactaccg agagcagatg atctactgga cagatgtgac cacccagggc    9240
agcatgatcc gaaggatgca ccttaacggg agcaatgtgc aggtcctaca ccgtacaggc    9300
ctcagcaacc ccgatgggct ggctgtggac tgggtgggtg caacctgta ctggtgcgac     9360 aaaggccggg acaccatcga ggtgtccaag ctcaatgggg cctatcggac ggtgctggtc    9420
agctctggcc tccgtgagcc cagggctctg gtggtggatg tgcagaatgg gtacctgtac    9480
tggacagact ggggtgacca ttcactgatc ggccgcatcg gcatggatgg gtccagccgc    9540
agcgtcatcg tggacaccaa gatcacatgg cccaatggcc tgacgctgga ctatgtcact    9600
gagcgcatct actgggccga cgcccgcgag gactacattg aatttgccag cctggatggc    9660
tccaatcgcc acgttgtgct gagccaggac atcccgcaca tctttgcact gaccctgttt    9720
gaggactacg tctactggac cgactgggaa acaaagtcca ttaaccgagc ccacaagacc    9780
acgggcacca caaaaacgct cctcatcagc acgctgcacc ggcccatgga cctgcatgtc    9840
ttccatgccc tgcgccagcc agacgtgccc aatcacccct gcaaggtcaa caatggtggc    9900
tgcagcaacc tgtgcctgct gtcccccggg ggagggcaca aatgtgcctg ccccaccaac    9960
ttctacctgg gcagcgatgg gcgcacctgt gtgtccaact gcacggctag ccagtttgta    10020
tgcaagaacg acaagtgcat cccccttctgg tggaagtgtg acaccgagga cgactgcggg    10080
gaccactcag acgagccccc ggactgccct gagttcaagt gccggcccgg acagttccag    10140
tgctccacag gtatctgcac aaaccctgcc ttcatctgcg atggcgacaa tgactgccag    10200
gacaacagtg acgaggccaa ctgtgacatc cacgtctgct tgcccagtca gttcaaatgc    10260
accaacacca accgctgtat tcccggcatc ttccgctgca atgggcagga caactgcgga    10320
gatggggagg atgagaggga ctgccccgag gtgacctgcg cccccaacca gttccagtgc    10380
tccattacca acggtgcat cccccggtc tgggtctgcg accggacaa tgactgtgtg         10440 gatggcagtg atgagcccgc caactgcacc cagatgacct gtggtgtgga cgagttccgc    10500
tgcaaggatt cgggccgctg catcccagcg cgttggaagt gtgacggaga ggatgactgt    10560
ggggatggct cggatgagcc caaggaagag tgtgatgaac gcacctgtga gccataccag    10620
ttccgctgca agaacaaccg ctgcgtgccc ggccgctggc agtgcgacta cgacaacgat    10680
tgcggtgaca actccgatga agagagctgc acccctcggc cctgctccga gagtgagttc    10740
tcctgtgcca acggccgctg catcgcgggg cgctggaaat gcgatggaga ccacgactgc    10800
gcggacggct cggacgagaa agactgcacc ccccgctgtg acatggacca gttccagtgc    10860
aagagcggcc actgcatccc cctgcgctgg cgctgtgacg cagacgccga ctgcatggac    10920
ggcagcgacg aggaggcctg cggcactggc gtgcggacct gccccctgga cgagttccag    10980
tgcaacaaca ccttgtgcaa gccgctggcc tggaagtgcg atggcgagga tgactgtggg    11040
gacaactcag atgagaaccc cgaggagtgt gccggttcg tgtgccctcc caaccggccc    11100
ttccgttgca agaatgaccg cgtctgtctg tggatcgggc gccaatgcga tggcacggac    11160
aactgtgggg atgggactga tgaagaggac tgtgagcccc ccacagccca caccaccac     11220 tgcaaagaca agaaggagtt tctgtgccgg aaccagcgct gcctctcctc ctccctgcgc    11280
tgcaacatgt tcgatgactg cggggacggc tctgacgagg aggactgcag catcgacccc    11340
aagctgacca gctgcgccac caatgccagc atctgtgggg acgaggcacg ctgcgtgcgc    11400
accgagaaag cggcctactg tgcctgccgc tcgggcttcc acaccgtgcc cggccagccc    11460
```

```
ggatgccaag acatcaacga gtgcctgcgc ttcggcacct gctcccagct ctgcaacaac   11520
accaagggcg ccaccctctg cagctgcgct cggaacttca tgaagacgca caacacctgc   11580
aaggccgaag ctctgagta ccaggtcctg tacatcgctg atgacaatga gatccgcagc   11640
ctgttccccg ccaccccca ttcggcttac gagcaggcat ccagggtga cgagagtgtc   11700 cgcattgatg ctatggatgt ccatgtcaag gctggccgtg tctattggac caactggcac   11760
acgggcacca tctcctaccg cagcctgcca cctgctgcgc ctcctaccac ttccaaccgc   11820
caccggcgac agattgaccg gggtgtcacc cacctcaaca tttcagggct gaagatgccc   11880
agaggcatcg ccatcgactg ggtggccgga acgtgtact ggaccgactc gggccgagat   11940
gtgattgagg tggcgcagat gaagggcgag aaccgcaaga cgctcatctc gggcatgatt   12000
gacgagcccc acgccattgt ggtggaccca ctgaggggga ccatgtactg gtcagactgg   12060
ggcaaccacc ccaagattga cggcagcg atggatggga cgcttcggga gacactggtg   12120
caggacaaca ttcagtggcc cacaggcctg gccgtggatt atcacaatga gcggctgtac   12180
tgggcagacc ccaagctttc agtcatcggc agcatccggc tcaatggcac ggaccccatt   12240
gtggctgctg acagcaaacg aggcctaagt cacccttca gcatcgacgt ctttgaggat   12300
tacatctatg tgtcaccta catcaataat cgtgtcttca agatccataa gtttggccac   12360 agcccttgg tcaacctgac agggggcctg agccacgcct ctgacgtggt cctttaccat   12420
cagcacaagc agcccgaagt gaccaaccca tgtgaccgca gaaatgcga gtggctctgc   12480 ctgctgagcc ccagtgggcc tgtctgcacc tgtcccaatg ggaagcggct ggacaacggc   12540
acatgcgtgc ctgtgccctc tccaacgccc ccccagatg ctccccggcc tggaacctgt   12600
aacctgcagt gcttcaacgg tggcagctgt ttcctcaatg cacggaggca gcccaagtgc   12660
cgctgccaac cccgctacac gggtgacaag tgtgaactgg accagtgctg ggagcactgt   12720
cgcaatgggg gcacctgtgc tgcctcccc tctggcatgc ccacgtgccg gtgccccacg   12780
ggcttcacgg gccccaaatg cacccagcag gtgtgtgcgg ctactgtgc caacaacagc   12840 acctgcactg tcaaccaggg caaccagccc cagtgccgat gcctacccgg cttcctgggc   12900
gaccgctgcc agtaccggca gtgctctggc tactgtgaga ctttggcac atgccagatg   12960 gctgctgatg gctcccgaca atgccgctgc actgcctact ttgagggatc gaggtgtgag   13020
gtgaacaagt gcagccgctg tctcgaaggg gcctgtgtgg tcaacaagca gagtggggat   13080
gtcacctgca actgcacgga tggccgggtg ccccccagct gtctgacctg cgtcggccac   13140
tgcagcaatg gcggctcctg taccatgaac agcaaaatga tgcctgagtg ccagtgccca   13200
ccccacatga cagggccccg gtgtgaggag cacgtcttca gccagcagca gccaggacat   13260
atagcctcca tcctaatccc tctgctgttg ctgctgctgc tggttctggt ggccggagtg   13320
gtattctggt ataagcggcg agtccaaggg gctaagggct tccagcacca acggatgacc   13380
aacggggcca tgaacgtgga gattggaaac cccacctaca agatgtacga aggcggagag   13440
cctgatgatg tgggaggcct actggacgct gactttgccc tggaccctga caagcccacc   13500
aacttcacca accccgtgta tgccacactc tacatggggg gccatggcag tcgccactcc   13560
ctggccagca cggacgagaa gcgagaactc ctgggccggg gccctgagga cgagataggg   13620
gaccccttgg catag                                                   13635
```

<210> SEQ ID NO 4
<211> LENGTH: 4544
<212> TYPE: PRT
<213> ORGANISM: Artificial Sequence
<220> FEATURE:
<223> OTHER INFORMATION: human low density lipoprotein receptor related
      protein (LRP)

<400> SEQUENCE: 4

```
Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
        50                  55                  60

Pro Gln Ser Lys Ala Gln Arg Cys Gln Pro Asn Glu His Asn Cys Leu
65              70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
130             135                 140

Gly Lys Thr Cys Lys Asp Phe Asp Glu Cys Ser Val Tyr Gly Thr Cys
145             150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
210             215                 220

Thr Ser Thr Arg Gln Thr Thr Ala Met Asp Phe Ser Tyr Ala Asn Glu
225             230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
290             295                 300

Phe Val Cys Asn Arg Asn Gly Asp Thr Cys Val Thr Leu Leu Asp Leu
305             310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
370             375                 380

Asp Ala Tyr Leu Asp Tyr Ile Glu Val Val Asp Tyr Glu Gly Lys Gly
```

```
            385                 390                 395                 400
Arg Gln Thr Ile Ile Gln Gly Ile Leu Ile Glu His Leu Tyr Gly Leu
                    405                 410                 415

Thr Val Phe Glu Asn Tyr Leu Tyr Ala Thr Asn Ser Asp Asn Ala Asn
                420                 425                 430

Ala Gln Lys Thr Ser Val Ile Arg Val Asn Arg Phe Asn Ser Thr
            435                 440                 445

Glu Tyr Gln Val Val Thr Arg Val Asp Lys Gly Gly Ala Leu His Ile
        450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
                500                 505                 510

Gly Ser Asp Gly Lys Ser Cys Lys Lys Pro Glu His Glu Leu Phe Leu
            515                 520                 525

Val Tyr Gly Lys Gly Arg Pro Gly Ile Ile Arg Gly Met Asp Met Gly
        530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
                580                 585                 590

Arg Glu Thr Ile Leu Lys Asp Gly Ile His Asn Val Glu Gly Val Ala
            595                 600                 605

Val Asp Trp Met Gly Asp Asn Leu Tyr Trp Thr Asp Asp Gly Pro Lys
        610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
                660                 665                 670

Asp Ser Arg Arg Gly Arg Leu Glu Arg Ala Trp Met Asp Gly Ser His
            675                 680                 685

Arg Asp Ile Phe Val Thr Ser Lys Thr Val Leu Trp Pro Asn Gly Leu
        690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
                740                 745                 750

Asn Tyr Leu Phe Trp Thr Glu Tyr Arg Ser Gly Ser Val Tyr Arg Leu
            755                 760                 765

Glu Arg Gly Val Gly Gly Ala Pro Pro Thr Val Thr Leu Leu Arg Ser
        770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815
```

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
            835                 840                 845

Val Pro Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
            885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
            915                 920                 925

Ala Thr Cys Ser Ala Arg Thr Cys Pro Pro Asn Gln Phe Ser Cys Ala
            930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
            965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn Asp Cys Gly Asp Asn Ser Asp Glu
            995                 1000                1005

Ala Gly Cys Ser His Ser Cys Ser Ser Thr Gln Phe Lys Cys Asn Ser
            1010                1015                1020

Gly Arg Cys Ile Pro Glu His Trp Thr Cys Asp Gly Asp Asn Asp Cys
1025                1030                1035                1040

Gly Asp Tyr Ser Asp Glu Thr His Ala Asn Cys Thr Asn Gln Ala Thr
            1045                1050                1055

Arg Pro Pro Gly Gly Cys His Thr Asp Glu Phe Gln Cys Arg Leu Asp
            1060                1065                1070

Gly Leu Cys Ile Pro Leu Arg Trp Arg Cys Asp Gly Asp Thr Asp Cys
            1075                1080                1085

Met Asp Ser Ser Asp Glu Lys Ser Cys Glu Gly Val Thr His Val Cys
            1090                1095                1100

Asp Pro Ser Val Lys Phe Gly Cys Lys Asp Ser Ala Arg Cys Ile Ser
1105                1110                1115                1120

Lys Ala Trp Val Cys Asp Gly Asp Asn Asp Cys Glu Asp Asn Ser Asp
            1125                1130                1135

Glu Glu Asn Cys Glu Ser Leu Ala Cys Arg Pro Pro Ser His Pro Cys
            1140                1145                1150

Ala Asn Asn Thr Ser Val Cys Leu Pro Pro Asp Lys Leu Cys Asp Gly
            1155                1160                1165

Asn Asp Asp Cys Gly Asp Gly Ser Asp Glu Gly Glu Leu Cys Asp Gln
            1170                1175                1180

Cys Ser Leu Asn Asn Gly Gly Cys Ser His Asn Cys Ser Val Ala Pro
1185                1190                1195                1200

Gly Glu Gly Ile Val Cys Ser Cys Pro Leu Gly Met Glu Leu Gly Pro
            1205                1210                1215

Asp Asn His Thr Cys Gln Ile Gln Ser Tyr Cys Ala Lys His Leu Lys
            1220                1225                1230

-continued

```
Cys Ser Gln Lys Cys Asp Gln Asn Lys Phe Ser Val Lys Cys Ser Cys
            1235                1240                1245

Tyr Glu Gly Trp Val Leu Glu Pro Asp Gly Glu Ser Cys Arg Ser Leu
        1250                1255                1260

Asp Pro Phe Lys Pro Phe Ile Ile Phe Ser Asn Arg His Glu Ile Arg
1265                1270                1275                1280

Arg Ile Asp Leu His Lys Gly Asp Tyr Ser Val Leu Pro Gly Leu
            1285                1290                1295

Arg Asn Thr Ile Ala Leu Asp Phe His Leu Ser Gln Ser Ala Leu Tyr
        1300                1305                1310

Trp Thr Asp Val Val Glu Asp Lys Ile Tyr Arg Gly Lys Leu Leu Asp
            1315                1320                1325

Asn Gly Ala Leu Thr Ser Phe Glu Val Val Ile Gln Tyr Gly Leu Ala
        1330                1335                1340

Thr Pro Glu Gly Leu Ala Val Asp Trp Ile Ala Gly Asn Ile Tyr Trp
1345                1350                1355                1360

Val Glu Ser Asn Leu Asp Gln Ile Glu Val Ala Lys Leu Asp Gly Thr
            1365                1370                1375

Leu Arg Thr Thr Leu Leu Ala Gly Asp Ile Glu His Pro Arg Ala Ile
        1380                1385                1390

Ala Leu Asp Pro Arg Asp Gly Ile Leu Phe Trp Thr Asp Trp Asp Ala
        1395                1400                1405

Ser Leu Pro Arg Ile Glu Ala Ala Ser Met Ser Gly Ala Gly Arg Arg
        1410                1415                1420

Thr Val His Arg Glu Thr Gly Ser Gly Gly Trp Pro Asn Gly Leu Thr
1425                1430                1435                1440

Val Asp Tyr Leu Glu Lys Arg Ile Leu Trp Ile Asp Ala Arg Ser Asp
            1445                1450                1455

Ala Ile Tyr Ser Ala Arg Tyr Asp Gly Ser Gly His Met Glu Val Leu
            1460                1465                1470

Arg Gly His Glu Phe Leu Ser His Pro Phe Ala Val Thr Leu Tyr Gly
            1475                1480                1485

Gly Glu Val Tyr Trp Thr Asp Trp Arg Thr Asn Thr Leu Ala Lys Ala
        1490                1495                1500

Asn Lys Trp Thr Gly His Asn Val Thr Val Val Gln Arg Thr Asn Thr
1505                1510                1515                1520

Gln Pro Phe Asp Leu Gln Val Tyr His Pro Ser Arg Gln Pro Met Ala
            1525                1530                1535

Pro Asn Pro Cys Glu Ala Asn Gly Gly Gln Gly Pro Cys Ser His Leu
        1540                1545                1550

Cys Leu Ile Asn Tyr Asn Arg Thr Val Ser Cys Ala Cys Pro His Leu
        1555                1560                1565

Met Lys Leu His Lys Asp Asn Thr Thr Cys Tyr Glu Phe Lys Lys Phe
        1570                1575                1580

Leu Leu Tyr Ala Arg Gln Met Glu Ile Arg Gly Val Asp Leu Asp Ala
1585                1590                1595                1600

Pro Tyr Tyr Asn Tyr Ile Ile Ser Phe Thr Val Pro Asp Ile Asp Asn
            1605                1610                1615

Val Thr Val Leu Asp Tyr Asp Ala Arg Glu Gln Arg Val Tyr Trp Ser
        1620                1625                1630

Asp Val Arg Thr Gln Ala Ile Lys Arg Ala Phe Ile Asn Gly Thr Gly
        1635                1640                1645

Val Glu Thr Val Val Ser Ala Asp Leu Pro Asn Ala His Gly Leu Ala
```

-continued

```
         1650              1655              1660

Val Asp Trp Val Ser Arg Asn Leu Phe Trp Thr Ser Tyr Asp Thr Asn
1665              1670              1675              1680

Lys Lys Gln Ile Asn Val Ala Arg Leu Asp Gly Ser Phe Lys Asn Ala
              1685              1690              1695

Val Val Gln Gly Leu Glu Gln Pro His Gly Leu Val Val His Pro Leu
              1700              1705              1710

Arg Gly Lys Leu Tyr Trp Thr Asp Gly Asp Asn Ile Ser Met Ala Asn
              1715              1720              1725

Met Asp Gly Ser Asn Arg Thr Leu Leu Phe Ser Gly Gln Lys Gly Pro
              1730              1735              1740

Val Gly Leu Ala Ile Asp Phe Pro Glu Ser Lys Leu Tyr Trp Ile Ser
1745              1750              1755              1760

Ser Gly Asn His Thr Ile Asn Arg Cys Asn Leu Asp Gly Ser Gly Leu
              1765              1770              1775

Glu Val Ile Asp Ala Met Arg Ser Gln Leu Gly Lys Ala Thr Ala Leu
              1780              1785              1790

Ala Ile Met Gly Asp Lys Leu Trp Trp Ala Asp Gln Val Ser Glu Lys
              1795              1800              1805

Met Gly Thr Cys Ser Lys Ala Asp Gly Ser Gly Ser Val Val Leu Arg
              1810              1815              1820

Asn Ser Thr Thr Leu Val Met His Met Lys Val Tyr Asp Glu Ser Ile
1825              1830              1835              1840

Gln Leu Asp His Lys Gly Thr Asn Pro Cys Ser Val Asn Asn Gly Asp
              1845              1850              1855

Cys Ser Gln Leu Cys Leu Pro Thr Ser Glu Thr Thr Arg Ser Cys Met
              1860              1865              1870

Cys Thr Ala Gly Tyr Ser Leu Arg Ser Gly Gln Gln Ala Cys Glu Gly
              1875              1880              1885

Val Gly Ser Phe Leu Leu Tyr Ser Val His Glu Gly Ile Arg Gly Ile
              1890              1895              1900

Pro Leu Asp Pro Asn Asp Lys Ser Asp Ala Leu Val Pro Val Ser Gly
1905              1910              1915              1920

Thr Ser Leu Ala Val Gly Ile Asp Phe His Ala Glu Asn Asp Thr Ile
              1925              1930              1935

Tyr Trp Val Asp Met Gly Leu Ser Thr Ile Ser Arg Ala Lys Arg Asp
              1940              1945              1950

Gln Thr Trp Arg Glu Asp Val Val Thr Asn Gly Ile Gly Arg Val Glu
              1955              1960              1965

Gly Ile Ala Val Asp Trp Ile Ala Gly Asn Ile Tyr Trp Thr Asp Gln
              1970              1975              1980

Gly Phe Asp Val Ile Glu Val Ala Arg Leu Asn Gly Ser Phe Arg Tyr
1985              1990              1995              2000

Val Val Ile Ser Gln Gly Leu Asp Lys Pro Arg Ala Ile Thr Val His
              2005              2010              2015

Pro Glu Lys Gly Tyr Leu Phe Trp Thr Glu Trp Gly Gln Tyr Pro Arg
              2020              2025              2030

Ile Glu Arg Ser Arg Leu Asp Gly Thr Glu Arg Val Val Leu Val Asn
              2035              2040              2045

Val Ser Ile Ser Trp Pro Asn Gly Ile Ser Val Asp Tyr Gln Asp Gly
              2050              2055              2060

Lys Leu Tyr Trp Cys Asp Ala Arg Thr Asp Lys Ile Glu Arg Ile Asp
2065              2070              2075              2080
```

```
Leu Glu Thr Gly Glu Asn Arg Glu Val Val Leu Ser Ser Asn Asn Met
                2085                2090                2095

Asp Met Phe Ser Val Ser Val Phe Glu Asp Phe Ile Tyr Trp Ser Asp
                2100                2105                2110

Arg Thr His Ala Asn Gly Ser Ile Lys Arg Gly Ser Lys Asp Asn Ala
                2115                2120                2125

Thr Asp Ser Val Pro Leu Arg Thr Gly Ile Gly Val Gln Leu Lys Asp
                2130                2135                2140

Ile Lys Val Phe Asn Arg Asp Arg Gln Lys Gly Thr Asn Val Cys Ala
2145                2150                2155                2160

Val Ala Asn Gly Gly Cys Gln Gln Leu Cys Leu Tyr Arg Gly Arg Gly
                2165                2170                2175

Gln Arg Ala Cys Ala Cys Ala His Gly Met Leu Ala Glu Asp Gly Ala
                2180                2185                2190

Ser Cys Arg Glu Tyr Ala Gly Tyr Leu Leu Tyr Ser Glu Arg Thr Ile
                2195                2200                2205

Leu Lys Ser Ile His Leu Ser Asp Glu Arg Asn Leu Asn Ala Pro Val
                2210                2215                2220

Gln Pro Phe Glu Asp Pro Glu His Met Lys Asn Val Ile Ala Leu Ala
2225                2230                2235                2240

Phe Asp Tyr Arg Ala Gly Thr Ser Pro Gly Thr Pro Asn Arg Ile Phe
                2245                2250                2255

Phe Ser Asp Ile His Phe Gly Asn Ile Gln Gln Ile Asn Asp Asp Gly
                2260                2265                2270

Ser Arg Arg Ile Thr Ile Val Glu Asn Val Gly Ser Val Glu Gly Leu
                2275                2280                2285

Ala Tyr His Arg Gly Trp Asp Thr Leu Tyr Trp Thr Ser Tyr Thr Thr
                2290                2295                2300

Ser Thr Ile Thr Arg His Thr Val Asp Gln Thr Arg Pro Gly Ala Phe
2305                2310                2315                2320

Glu Arg Glu Thr Val Ile Thr Met Ser Gly Asp Asp His Pro Arg Ala
                2325                2330                2335

Phe Val Leu Asp Glu Cys Gln Asn Leu Met Phe Trp Thr Asn Trp Asn
                2340                2345                2350

Glu Gln His Pro Ser Ile Met Arg Ala Ala Leu Ser Gly Ala Asn Val
                2355                2360                2365

Leu Thr Leu Ile Glu Lys Asp Ile Arg Thr Pro Asn Gly Leu Ala Ile
                2370                2375                2380

Asp His Arg Ala Glu Lys Leu Tyr Phe Ser Asp Ala Thr Leu Asp Lys
2385                2390                2395                2400

Ile Glu Arg Cys Glu Tyr Asp Gly Ser His Arg Tyr Val Ile Leu Lys
                2405                2410                2415

Ser Glu Pro Val His Pro Phe Gly Leu Ala Val Tyr Gly Glu His Ile
                2420                2425                2430

Phe Trp Thr Asp Trp Val Arg Arg Ala Val Gln Arg Ala Asn Lys His
                2435                2440                2445

Val Gly Ser Asn Met Lys Leu Leu Arg Val Asp Ile Pro Gln Gln Pro
2450                2455                2460

Met Gly Ile Ile Ala Val Ala Asn Asp Thr Asn Ser Cys Glu Leu Ser
2465                2470                2475                2480

Pro Cys Arg Ile Asn Asn Gly Gly Cys Gln Asp Leu Cys Leu Leu Thr
                2485                2490                2495
```

His Gln Gly His Val Asn Cys Ser Cys Arg Gly Gly Arg Ile Leu Gln
            2500            2505                2510

Asp Asp Leu Thr Cys Arg Ala Val Asn Ser Ser Cys Arg Ala Gln Asp
        2515            2520                2525

Glu Phe Glu Cys Ala Asn Gly Glu Cys Ile Asn Phe Ser Leu Thr Cys
            2530            2535                2540

Asp Gly Val Pro His Cys Lys Asp Lys Ser Asp Glu Lys Pro Ser Tyr
2545            2550                2555                2560

Cys Asn Ser Arg Arg Cys Lys Lys Thr Phe Arg Gln Cys Ser Asn Gly
            2565                2570                2575

Arg Cys Val Ser Asn Met Leu Trp Cys Asn Gly Ala Asp Asp Cys Gly
            2580            2585                2590

Asp Gly Ser Asp Glu Ile Pro Cys Asn Lys Thr Ala Cys Gly Val Gly
        2595                2600                2605

Glu Phe Arg Cys Arg Asp Gly Thr Cys Ile Gly Asn Ser Ser Arg Cys
            2610            2615                2620

Asn Gln Phe Val Asp Cys Glu Asp Ala Ser Asp Glu Met Asn Cys Ser
2625                2630                2635                2640

Ala Thr Asp Cys Ser Ser Tyr Phe Arg Leu Gly Val Lys Gly Val Leu
            2645                2650                2655

Phe Gln Pro Cys Glu Arg Thr Ser Leu Cys Tyr Ala Pro Ser Trp Val
            2660                2665                2670

Cys Asp Gly Ala Asn Asp Cys Gly Asp Tyr Ser Asp Glu Arg Asp Cys
            2675            2680                2685

Pro Gly Val Lys Arg Pro Arg Cys Pro Leu Asn Tyr Phe Ala Cys Pro
        2690            2695                2700

Ser Gly Arg Cys Ile Pro Met Ser Trp Thr Cys Asp Lys Glu Asp Asp
2705            2710            2715                2720

Cys Glu His Gly Glu Asp Glu Thr His Cys Asn Lys Phe Cys Ser Glu
            2725                2730                2735

Ala Gln Phe Glu Cys Gln Asn His Arg Cys Ile Ser Lys Gln Trp Leu
            2740            2745                2750

Cys Asp Gly Ser Asp Asp Cys Gly Asp Gly Ser Asp Glu Ala Ala His
            2755            2760                2765

Cys Glu Gly Lys Thr Cys Gly Pro Ser Ser Phe Ser Cys Pro Gly Thr
            2770            2775                2780

His Val Cys Val Pro Glu Arg Trp Leu Cys Asp Gly Asp Lys Asp Cys
2785            2790                2795                2800

Ala Asp Gly Ala Asp Glu Ser Ile Ala Ala Gly Cys Leu Tyr Asn Ser
            2805            2810                2815

Thr Cys Asp Asp Arg Glu Phe Met Cys Gln Asn Arg Gln Cys Ile Pro
        2820            2825                2830

Lys His Phe Val Cys Asp His Asp Arg Asp Cys Ala Asp Gly Ser Asp
        2835            2840                2845

Glu Ser Pro Glu Cys Glu Tyr Pro Thr Cys Gly Pro Ser Glu Phe Arg
        2850            2855                2860

Cys Ala Asn Gly Arg Cys Leu Ser Ser Arg Gln Trp Glu Cys Asp Gly
2865            2870            2875                2880

Glu Asn Asp Cys His Asp Gln Ser Asp Glu Ala Pro Lys Asn Pro His
            2885                2890                2895

Cys Thr Ser Gln Glu His Lys Cys Asn Ala Ser Ser Gln Phe Leu Cys
            2900            2905                2910

Ser Ser Gly Arg Cys Val Ala Glu Ala Leu Leu Cys Asn Gly Gln Asp

```
            2915                2920                2925
Asp Cys Gly Asp Ser Ser Asp Glu Arg Gly Cys His Ile Asn Glu Cys
        2930                2935                2940

Leu Ser Arg Lys Leu Ser Gly Cys Ser Gln Asp Cys Glu Asp Leu Lys
2945                2950                2955                2960

Ile Gly Phe Lys Cys Arg Cys Arg Pro Gly Phe Arg Leu Lys Asp Asp
                2965                2970                2975

Gly Arg Thr Cys Ala Asp Val Asp Glu Cys Ser Thr Thr Phe Pro Cys
                2980                2985                2990

Ser Gln Arg Cys Ile Asn Thr His Gly Ser Tyr Lys Cys Leu Cys Val
                2995                3000                3005

Glu Gly Tyr Ala Pro Arg Gly Gly Asp Pro His Ser Cys Lys Ala Val
                3010                3015                3020

Thr Asp Glu Glu Pro Phe Leu Ile Phe Ala Asn Arg Tyr Tyr Leu Arg
3025                3030                3035                3040

Lys Leu Asn Leu Asp Gly Ser Asn Tyr Thr Leu Leu Lys Gln Gly Leu
                3045                3050                3055

Asn Asn Ala Val Ala Leu Asp Phe Asp Tyr Arg Glu Gln Met Ile Tyr
                3060                3065                3070

Trp Thr Asp Val Thr Thr Gln Gly Ser Met Ile Arg Arg Met His Leu
                3075                3080                3085

Asn Gly Ser Asn Val Gln Val Leu His Arg Thr Gly Leu Ser Asn Pro
                3090                3095                3100

Asp Gly Leu Ala Val Asp Trp Val Gly Gly Asn Leu Tyr Trp Cys Asp
3105                3110                3115                3120

Lys Gly Arg Asp Thr Ile Glu Val Ser Lys Leu Asn Gly Ala Tyr Arg
                3125                3130                3135

Thr Val Leu Val Ser Ser Gly Leu Arg Glu Pro Arg Ala Leu Val Val
                3140                3145                3150

Asp Val Gln Asn Gly Tyr Leu Tyr Trp Thr Asp Trp Gly Asp His Ser
                3155                3160                3165

Leu Ile Gly Arg Ile Gly Met Asp Gly Ser Ser Arg Ser Val Ile Val
                3170                3175                3180

Asp Thr Lys Ile Thr Trp Pro Asn Gly Leu Thr Leu Asp Tyr Val Thr
3185                3190                3195                3200

Glu Arg Ile Tyr Trp Ala Asp Ala Arg Glu Asp Tyr Ile Glu Phe Ala
                3205                3210                3215

Ser Leu Asp Gly Ser Asn Arg His Val Val Leu Ser Gln Asp Ile Pro
                3220                3225                3230

His Ile Phe Ala Leu Thr Leu Phe Glu Asp Tyr Val Tyr Trp Thr Asp
                3235                3240                3245

Trp Glu Thr Lys Ser Ile Asn Arg Ala His Lys Thr Thr Gly Thr Asn
                3250                3255                3260

Lys Thr Leu Leu Ile Ser Thr Leu His Arg Pro Met Asp Leu His Val
3265                3270                3275                3280

Phe His Ala Leu Arg Gln Pro Asp Val Pro Asn His Pro Cys Lys Val
                3285                3290                3295

Asn Asn Gly Gly Cys Ser Asn Leu Cys Leu Leu Ser Pro Gly Gly Gly
                3300                3305                3310

His Lys Cys Ala Cys Pro Thr Asn Phe Tyr Leu Gly Ser Asp Gly Arg
                3315                3320                3325

Thr Cys Val Ser Asn Cys Thr Ala Ser Gln Phe Val Cys Lys Asn Asp
                3330                3335                3340
```

```
Lys Cys Ile Pro Phe Trp Trp Lys Cys Asp Thr Glu Asp Cys Gly
3345                3350                3355                3360

Asp His Ser Asp Glu Pro Pro Asp Cys Pro Glu Phe Lys Cys Arg Pro
                3365                3370                3375

Gly Gln Phe Gln Cys Ser Thr Gly Ile Cys Thr Asn Pro Ala Phe Ile
            3380                3385                3390

Cys Asp Gly Asp Asn Asp Cys Gln Asp Asn Ser Asp Glu Ala Asn Cys
        3395                3400                3405

Asp Ile His Val Cys Leu Pro Ser Gln Phe Lys Cys Thr Asn Thr Asn
    3410                3415                3420

Arg Cys Ile Pro Gly Ile Phe Arg Cys Asn Gly Gln Asp Asn Cys Gly
3425                3430                3435                3440

Asp Gly Glu Asp Glu Arg Asp Cys Pro Glu Val Thr Cys Ala Pro Asn
                3445                3450                3455

Gln Phe Gln Cys Ser Ile Thr Lys Arg Cys Ile Pro Arg Val Trp Val
            3460                3465                3470

Cys Asp Arg Asp Asn Asp Cys Val Asp Gly Ser Asp Glu Pro Ala Asn
        3475                3480                3485

Cys Thr Gln Met Thr Cys Gly Val Asp Glu Phe Arg Cys Lys Asp Ser
    3490                3495                3500

Gly Arg Cys Ile Pro Ala Arg Trp Lys Cys Asp Gly Glu Asp Asp Cys
3505                3510                3515                3520

Gly Asp Gly Ser Asp Glu Pro Lys Glu Glu Cys Asp Glu Arg Thr Cys
                3525                3530                3535

Glu Pro Tyr Gln Phe Arg Cys Lys Asn Asn Arg Cys Val Pro Gly Arg
            3540                3545                3550

Trp Gln Cys Asp Tyr Asp Asn Asp Cys Gly Asp Asn Ser Asp Glu Glu
        3555                3560                3565

Ser Cys Thr Pro Arg Pro Cys Ser Glu Ser Glu Phe Ser Cys Ala Asn
    3570                3575                3580

Gly Arg Cys Ile Ala Gly Arg Trp Lys Cys Asp Gly Asp His Asp Cys
3585                3590                3595                3600

Ala Asp Gly Ser Asp Glu Lys Asp Cys Thr Pro Arg Cys Asp Met Asp
                3605                3610                3615

Gln Phe Gln Cys Lys Ser Gly His Cys Ile Pro Leu Arg Trp Arg Cys
            3620                3625                3630

Asp Ala Asp Ala Asp Cys Met Asp Gly Ser Asp Glu Glu Ala Cys Gly
        3635                3640                3645

Thr Gly Val Arg Thr Cys Pro Leu Asp Glu Phe Gln Cys Asn Asn Thr
    3650                3655                3660

Leu Cys Lys Pro Leu Ala Trp Lys Cys Asp Gly Glu Asp Asp Cys Gly
3665                3670                3675                3680

Asp Asn Ser Asp Glu Asn Pro Glu Glu Cys Ala Arg Phe Val Cys Pro
                3685                3690                3695

Pro Asn Arg Pro Phe Arg Cys Lys Asn Asp Arg Val Cys Leu Trp Ile
            3700                3705                3710

Gly Arg Gln Cys Asp Gly Thr Asp Asn Cys Gly Asp Gly Thr Asp Glu
        3715                3720                3725

Glu Asp Cys Glu Pro Pro Thr Ala His Thr Thr His Cys Lys Asp Lys
    3730                3735                3740

Lys Glu Phe Leu Cys Arg Asn Gln Arg Cys Leu Ser Ser Ser Leu Arg
3745                3750                3755                3760
```

-continued

```
Cys Asn Met Phe Asp Asp Cys Gly Asp Gly Ser Asp Glu Glu Asp Cys
                3765                3770                3775
Ser Ile Asp Pro Lys Leu Thr Ser Cys Ala Thr Asn Ala Ser Ile Cys
                3780                3785                3790
Gly Asp Glu Ala Arg Cys Val Arg Thr Glu Lys Ala Ala Tyr Cys Ala
            3795                3800                3805
Cys Arg Ser Gly Phe His Thr Val Pro Gly Gln Pro Gly Cys Gln Asp
            3810                3815                3820
Ile Asn Glu Cys Leu Arg Phe Gly Thr Cys Ser Gln Leu Cys Asn Asn
3825                3830                3835                3840
Thr Lys Gly Gly His Leu Cys Ser Cys Ala Arg Asn Phe Met Lys Thr
                3845                3850                3855
His Asn Thr Cys Lys Ala Glu Gly Ser Glu Tyr Gln Val Leu Tyr Ile
                3860                3865                3870
Ala Asp Asp Asn Glu Ile Arg Ser Leu Phe Pro Gly His Pro His Ser
                3875                3880                3885
Ala Tyr Glu Gln Ala Phe Gln Gly Asp Glu Ser Val Arg Ile Asp Ala
            3890                3895                3900
Met Asp Val His Val Lys Ala Gly Arg Val Tyr Trp Thr Asn Trp His
3905                3910                3915                3920
Thr Gly Thr Ile Ser Tyr Arg Ser Leu Pro Pro Ala Ala Pro Pro Thr
                3925                3930                3935
Thr Ser Asn Arg His Arg Arg Gln Ile Asp Arg Gly Val Thr His Leu
                3940                3945                3950
Asn Ile Ser Gly Leu Lys Met Pro Arg Gly Ile Ala Ile Asp Trp Val
                3955                3960                3965
Ala Gly Asn Val Tyr Trp Thr Asp Ser Gly Arg Asp Val Ile Glu Val
            3970                3975                3980
Ala Gln Met Lys Gly Glu Asn Arg Lys Thr Leu Ile Ser Gly Met Ile
3985                3990                3995                4000
Asp Glu Pro His Ala Ile Val Val Asp Pro Leu Arg Gly Thr Met Tyr
                4005                4010                4015
Trp Ser Asp Trp Gly Asn His Pro Lys Ile Glu Thr Ala Ala Met Asp
                4020                4025                4030
Gly Thr Leu Arg Glu Thr Leu Val Gln Asp Asn Ile Gln Trp Pro Thr
                4035                4040                4045
Gly Leu Ala Val Asp Tyr His Asn Glu Arg Leu Tyr Trp Ala Asp Ala
            4050                4055                4060
Lys Leu Ser Val Ile Gly Ser Ile Arg Leu Asn Gly Thr Asp Pro Ile
4065                4070                4075                4080
Val Ala Ala Asp Ser Lys Arg Gly Leu Ser His Pro Phe Ser Ile Asp
                4085                4090                4095
Val Phe Glu Asp Tyr Ile Tyr Gly Val Thr Tyr Ile Asn Asn Arg Val
                4100                4105                4110
Phe Lys Ile His Lys Phe Gly His Ser Pro Leu Val Asn Leu Thr Gly
                4115                4120                4125
Gly Leu Ser His Ala Ser Asp Val Val Leu Tyr His Gln His Lys Gln
            4130                4135                4140
Pro Glu Val Thr Asn Pro Cys Asp Arg Lys Lys Cys Glu Trp Leu Cys
4145                4150                4155                4160
Leu Leu Ser Pro Ser Gly Pro Val Cys Thr Cys Pro Asn Gly Lys Arg
                4165                4170                4175
Leu Asp Asn Gly Thr Cys Val Pro Val Pro Ser Pro Thr Pro Pro Pro
```

-continued

```
                4180                4185                    4190
Asp Ala Pro Arg Pro Gly Thr Cys Asn Leu Gln Cys Phe Asn Gly Gly
            4195                4200                4205
Ser Cys Phe Leu Asn Ala Arg Arg Gln Pro Lys Cys Arg Cys Gln Pro
        4210                4215                4220
Arg Tyr Thr Gly Asp Lys Cys Glu Leu Asp Gln Cys Trp Glu His Cys
4225                4230                4235                4240
Arg Asn Gly Gly Thr Cys Ala Ala Ser Pro Ser Gly Met Pro Thr Cys
                4245                4250                4255
Arg Cys Pro Thr Gly Phe Thr Gly Pro Lys Cys Thr Gln Gln Val Cys
            4260                4265                4270
Ala Gly Tyr Cys Ala Asn Asn Ser Thr Cys Thr Val Asn Gln Gly Asn
        4275                4280                4285
Gln Pro Gln Cys Arg Cys Leu Pro Gly Phe Leu Gly Asp Arg Cys Gln
            4290                4295                4300
Tyr Arg Gln Cys Ser Gly Tyr Cys Glu Asn Phe Gly Thr Cys Gln Met
4305                4310                4315                4320
Ala Ala Asp Gly Ser Arg Gln Cys Arg Cys Thr Ala Tyr Phe Glu Gly
                4325                4330                4335
Ser Arg Cys Glu Val Asn Lys Cys Ser Arg Cys Leu Glu Gly Ala Cys
            4340                4345                4350
Val Val Asn Lys Gln Ser Gly Asp Val Thr Cys Asn Cys Thr Asp Gly
        4355                4360                4365
Arg Val Ala Pro Ser Cys Leu Thr Cys Val Gly His Cys Ser Asn Gly
        4370                4375                4380
Gly Ser Cys Thr Met Asn Ser Lys Met Met Pro Glu Cys Gln Cys Pro
4385                4390                4395                4400
Pro His Met Thr Gly Pro Arg Cys Glu Glu His Val Phe Ser Gln Gln
                4405                4410                4415
Gln Pro Gly His Ile Ala Ser Ile Leu Ile Pro Leu Leu Leu Leu Leu
            4420                4425                4430
Leu Leu Val Leu Val Ala Gly Val Val Phe Trp Tyr Lys Arg Arg Val
        4435                4440                4445
Gln Gly Ala Lys Gly Phe Gln His Gln Arg Met Thr Asn Gly Ala Met
    4450                4455                4460
Asn Val Glu Ile Gly Asn Pro Thr Tyr Lys Met Tyr Glu Gly Gly Glu
4465                4470                4475                4480
Pro Asp Asp Val Gly Gly Leu Leu Asp Ala Asp Phe Ala Leu Asp Pro
                4485                4490                4495
Asp Lys Pro Thr Asn Phe Thr Asn Pro Val Tyr Ala Thr Leu Tyr Met
            4500                4505                4510
Gly Gly His Gly Ser Arg His Ser Leu Ala Ser Thr Asp Glu Lys Arg
            4515                4520                4525
Glu Leu Leu Gly Arg Gly Pro Glu Asp Glu Ile Gly Asp Pro Leu Ala
        4530                4535                4540

<210> SEQ ID NO 5
<211> LENGTH: 1074
<212> TYPE: DNA
<213> ORGANISM: Artificial Sequence
<220> FEATURE:
<223> OTHER INFORMATION: human receptor associated protein (RAP)

<400> SEQUENCE: 5
atggcgccgc ggagggtcag gtcgtttctg cgcgggctcc cggcgctgct actgctgctg    60
```

-continued

```
ctcttcctcg ggccctggcc cgctgcgagc cacggcggca agtactcgcg ggagaagaac    120
cagcccaagc cgtccccgaa acgcgagtcc ggagaggagt tccgcatgga aagttgaac    180 cagctgtggg agaaggccca gcgactgcat cttcctcccg tgaggctggc cgagctccac    240
gctgatctga agatacagga gagggacgaa ctcgcctgga agaaactaaa gcttgacggc    300
ttggacgaag atggggagaa ggaagcgaga ctcatacgca acctcaatgt catcttggcc    360
aagtatggtc tggacggaaa gaaggacgct cggcaggtga ccagcaactc cctcagtggc    420
acccaggaag acgggctgga tgaccccagg ctggaaaagc tgtggcacaa ggcgaagacc    480
tctgggaaat tctccggcga agaactggac aagctctggc gggagttcct gcatcacaaa    540
gagaaagttc acgagtacaa cgtcctgctg agaccctga gcaggaccga agaaatccac    600
gagaacgtca ttagcccctc ggacctgagc gacatcaagg gcagcgtcct gcacagcagg    660
cacacggagc tgaaggagaa gctgcgcagc atcaaccagg gcctggaccg cctgcgcagg    720
gtcagccacc agggctacag cactgaggct gagttcgagg agcccagggt gattgacctg    780
tgggacctgg cgcagtccgc caacctcacg gacaaggagc tggaggcgtt ccgggaggag    840
ctcaagcact tcgaagccaa aatcgagaag cacaaccact accagaagca gctggagatt    900
gcgcacgaga agctgaggca cgcagagagc gtgggcgacg gcgagcgtgt gagccgcagc    960
cgcgagaagc acgccctgct ggaggggcgg accaaggagc tgggctacac ggtgaagaag    1020
catctgcagg acctgtccgg caggatctcc agagctcggc acaacgaact ctga    1074
```

<210> SEQ ID NO 6
<211> LENGTH: 357
<212> TYPE: PRT
<213> ORGANISM: Artificial Sequence
<220> FEATURE:
<223> OTHER INFORMATION: human receptor associated protein (RAP)

<400> SEQUENCE: 6

```
Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
```

```
              180                 185                 190
Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
    290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
        355

<210> SEQ ID NO 7
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 7
ccggacagag gatgaggtcc acattctcga gaatgtggac ctcatcctct gttttttg      58

<210> SEQ ID NO 8
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 8
ccgggggcga cagatgcgaa agaaactcga gtttctttcg catctgtcgc ccttttttg     58

<210> SEQ ID NO 9
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 9
ccggacatca acagcatcaa ctttgctcga gcaaagttga tgctgttgat gttttttg      58

<210> SEQ ID NO 10
<211> LENGTH: 58
<212> TYPE: DNA
<213> ORGANISM: Artificial Sequence
<220> FEATURE:
<223> OTHER INFORMATION: laboratory-synthesized sequences
```

<400> SEQUENCE: 10
ccggatggaa gaactggcgg cttaactcga gttaagccgc cagttcttcc atttttg         58

<210> SEQ ID NO 11
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 11
ccgggatgaa gttggctgcg ttaatctcga gattaacgca gccaacttca tctttttg        58

<210> SEQ ID NO 12
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 12
ccggcggagt ggtattctgg tataactcga gttataccag aataccactc cgtttttg        58

<210> SEQ ID NO 13
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 13
ccggccgcga ggactacatt gaattctcga gaattcaatg tagtcctcgc ggtttttg        58

<210> SEQ ID NO 14
<211> LENGTH: 62
<212> TYPE: DNA
<213> ORGANISM: Artificial Sequence
<220> FEATURE:
<223> OTHER INFORMATION: laboratory-synthesized sequences

<400> SEQUENCE: 14
gtaccggaca tcgatgatag gatctttgct cgagcaaaga tcctatcatc gatgtttttt     60
tg                                                                    62

<210> SEQ ID NO 15
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 15
ccgggatgcc tatctggact atattctcga gaatatagtc cagataggca tctttttg       58

<210> SEQ ID NO 16
<211> LENGTH: 58
<212> TYPE: DNA
<213> ORGANISM: Artificial Sequence
<220> FEATURE:
<223> OTHER INFORMATION: laboratory-synthesized sequences

<400> SEQUENCE: 16
ccggacagct tcctgagggc taattctcga gaattagccc tcaggaagct gtttttg        58